US010912947B2

(12) United States Patent
Kircher et al.

(10) Patent No.: US 10,912,947 B2
(45) Date of Patent: Feb. 9, 2021

(54) SYSTEMS AND METHODS FOR TREATMENT OF DISEASE VIA APPLICATION OF MECHANICAL FORCE BY CONTROLLED ROTATION OF NANOPARTICLES INSIDE CELLS

(71) Applicant: Memorial Sloan Kettering Cancer Center, New York, NY (US)

(72) Inventors: Moritz F. Kircher, Boston, MA (US); Erik Renström, Landskrona (SE); Martin Koch, Valby (DK); Ernst Stetter, Seeheim-Jugenheim (DE); Thomas Reis, Kleinheubach (DE)

(73) Assignee: Memorial Sloan Kettering Cancer Center, New York, NY (US)

( * ) Notice: Subject to any disclaimer, the term of this patent is extended or adjusted under 35 U.S.C. 154(b) by 150 days.

(21) Appl. No.: 15/255,611

(22) Filed: Sep. 2, 2016

(65) Prior Publication Data

US 2016/0367668 A1     Dec. 22, 2016

Related U.S. Application Data

(63) Continuation-in-part of application No. PCT/US2015/018746, filed on Mar. 4, 2015.
(Continued)

(51) Int. Cl.
*A61N 2/02*     (2006.01)
*A61K 41/00*    (2020.01)
*A61K 47/68*    (2017.01)

(52) U.S. Cl.
CPC ............ *A61N 2/02* (2013.01); *A61K 41/0028* (2013.01); *A61K 47/6849* (2017.08)

(58) Field of Classification Search
CPC ... A61K 41/0028; A61K 47/6849; A61N 2/02
See application file for complete search history.

(56) References Cited

U.S. PATENT DOCUMENTS 4,127,329 A    11/1978  Chang et al.
4,604,992 A     8/1986  Sato
(Continued)

FOREIGN PATENT DOCUMENTS

CN    101679022 A    3/2010
CN    102015020 A    4/2011
(Continued)

OTHER PUBLICATIONS

Akerman, M; Nanocrystal targeting in vivo, 2002, PNAS, vol. 99, p. 12617 (Year: 2002).*
(Continued)

*Primary Examiner* — Chrisine H Matthews
(74) *Attorney, Agent, or Firm* — Wolf, Greenfield & Sacks, P.C.

(57) ABSTRACT

The present disclosure describes systems, apparatus, and methods for application of dynamic magnetic field (DMF) treatment to direct movement, and specifically rotation, of magnetic particles associated with a target structure, so that mechanical force is applied to the target structure. In certain embodiments, the present disclosure demonstrates application of DMF treatment to direct rotation about the axis in individual magnetic particles (e.g., superparamagnetic nanoparticles), effecting permeabilization and/or other disruption of membranes (e.g., cell membranes and/or intracellular membranes). In certain embodiments, the present disclosure describes use of an alternating current superconductor (ACSC) to greatly enhance the magnetic field amplitude so that the field can penetrate deeper into a body with sufficient amplitude to control movement of the nanoparticles within a working volume.

25 Claims, 17 Drawing Sheets

Related U.S. Application Data

(60) Provisional application No. 62/215,001, filed on Sep. 6, 2015, provisional application No. 61/947,830, filed on Mar. 4, 2014.

(56) References Cited

U.S. PATENT DOCUMENTS

| | | |
|---|---|---|
| 4,669,467 A | 6/1987 | Willett et al. |
| 4,938,205 A | 7/1990 | Nudelman |
| 5,275,594 A | 1/1994 | Baker et al. |
| 5,293,872 A | 3/1994 | Alfano et al. |
| 5,300,097 A | 4/1994 | Lerner et al. |
| 5,306,403 A | 4/1994 | Vo-Dinh |
| 5,491,510 A | 2/1996 | Gove |
| 5,594,497 A | 1/1997 | Ahern et al. |
| 5,609,907 A | 3/1997 | Natan |
| 5,713,364 A | 2/1998 | DeBaryshe et al. |
| 5,721,102 A | 2/1998 | Vo-Dinh |
| 5,813,987 A | 9/1998 | Modell et al. |
| 5,949,388 A | 9/1999 | Atsumi et al. |
| 6,002,471 A | 12/1999 | Quake |
| 6,006,126 A | 12/1999 | Cosman |
| 6,008,889 A | 12/1999 | Zeng et al. |
| 6,019,719 A | 2/2000 | Schulz et al. |
| 6,025,202 A | 2/2000 | Natan |
| 6,127,120 A | 10/2000 | Graham et al. |
| 6,174,291 B1 | 1/2001 | McMahon et al. |
| 6,174,677 B1 | 1/2001 | Vo-Dinh |
| 6,219,137 B1 | 4/2001 | Vo-Dinh |
| 6,228,076 B1 | 5/2001 | Winston et al. |
| 6,242,264 B1 | 6/2001 | Natan et al. |
| 6,251,127 B1 | 6/2001 | Biel |
| 6,254,852 B1 | 7/2001 | Glajch et al. |
| 6,514,767 B1 | 2/2003 | Natan |
| 6,579,726 B1 | 6/2003 | Natan et al. |
| 6,624,886 B2 | 9/2003 | Natan et al. |
| 6,640,130 B1 | 10/2003 | Freeman et al. |
| 6,788,860 B1 | 9/2004 | Treado et al. |
| 6,959,024 B2 | 10/2005 | Paldus et al. |
| 7,076,092 B2 | 7/2006 | Hollars et al. |
| 7,192,778 B2 | 3/2007 | Natan |
| 7,443,489 B2 | 10/2008 | Natan |
| 7,538,859 B2 | 5/2009 | Tearney et al. |
| 7,656,525 B2 | 2/2010 | Zhao et al. |
| 7,738,096 B2 | 6/2010 | Zhao et al. |
| 7,760,352 B2 | 7/2010 | Armstrong et al. |
| 7,826,176 B2 | 11/2010 | Shirotori et al. |
| 7,829,140 B1 | 11/2010 | Zhong et al. |
| 8,054,463 B2 | 11/2011 | Morris et al. |
| 8,320,650 B2 | 11/2012 | Demos et al. |
| 8,409,862 B2 | 4/2013 | Caulfield et al. |
| 8,409,863 B2 | 4/2013 | Natan et al. |
| 8,416,405 B2 | 4/2013 | Panza et al. |
| 8,497,131 B2 | 7/2013 | Natan et al. |
| 8,568,878 B2 | 10/2013 | Wilson et al. |
| 8,771,978 B2 | 7/2014 | Ragan |
| 8,795,628 B2 | 8/2014 | Gambhir et al. |
| 8,918,161 B2 | 12/2014 | Natan et al. |
| 9,086,533 B1 | 7/2015 | Wach |
| 9,295,391 B1 | 3/2016 | Tearney et al. |
| 9,561,292 B1 | 2/2017 | Vo-Dinh et al. |
| 9,833,144 B2 | 12/2017 | Kircher et al. |
| 10,105,456 B2 | 10/2018 | Harmsen et al. |
| 10,322,194 B2 | 6/2019 | Kircher et al. |
| 2002/0045266 A1 | 4/2002 | Fenniri |
| 2002/0082498 A1 | 6/2002 | Wendt et al. |
| 2002/0165594 A1 | 11/2002 | Biel |
| 2002/0187082 A1 | 12/2002 | Wu et al. |
| 2003/0055307 A1 | 3/2003 | Elmaleh et al. |
| 2003/0191379 A1 | 10/2003 | Benaron et al. |
| 2003/0201208 A1 | 10/2003 | Koch et al. |
| 2004/0009341 A1 | 1/2004 | Naasani |
| 2004/0010192 A1 | 1/2004 | Benaron et al. |
| 2004/0073120 A1 | 4/2004 | Motz et al. |
| 2004/0225222 A1 | 11/2004 | Zeng et al. |
| 2004/0254419 A1 | 12/2004 | Wang et al. |
| 2004/0254454 A1 | 12/2004 | Kockro |
| 2005/0014851 A1 | 1/2005 | Bringley |
| 2005/0074779 A1 | 4/2005 | Vo-Dinh |
| 2005/0143662 A1 | 6/2005 | Marchitto et al. |
| 2005/0221494 A1 | 10/2005 | Natan |
| 2005/0272160 A1 | 12/2005 | Natan |
| 2005/0277816 A1 | 12/2005 | Maier et al. |
| 2006/0008924 A1 | 1/2006 | Anker et al. |
| 2006/0054506 A1 | 3/2006 | Natan et al. |
| 2006/0098194 A1 | 5/2006 | Tuschel |
| 2006/0173293 A1 | 8/2006 | Marquart et al. |
| 2006/0250613 A1 | 11/2006 | Demuth et al. |
| 2007/0010809 A1 | 1/2007 | Hovda et al. |
| 2007/0134805 A1 | 6/2007 | Gilbert |
| 2007/0167838 A1 | 7/2007 | Hubble et al. |
| 2007/0178067 A1 | 8/2007 | Maier et al. |
| 2007/0196281 A1 | 8/2007 | Jin et al. |
| 2007/0232874 A1 | 10/2007 | Ince |
| 2007/0238953 A1 | 10/2007 | Lucassen et al. |
| 2007/0255356 A1 | 11/2007 | Rose et al. |
| 2007/0260295 A1 | 11/2007 | Chen et al. |
| 2007/0269382 A1 | 11/2007 | Santra et al. |
| 2007/0282190 A1 | 12/2007 | Dekel et al. |
| 2007/0299550 A1 | 12/2007 | Nishijima et al. |
| 2008/0007716 A1 | 1/2008 | Igarashi |
| 2008/0058908 A1 | 3/2008 | Bornstein |
| 2008/0089839 A1 | 4/2008 | Lu et al. |
| 2008/0095852 A1 | 4/2008 | Kong et al. |
| 2008/0118912 A1 | 5/2008 | Dickson et al. |
| 2008/0119832 A1 | 5/2008 | Cronin |
| 2008/0305045 A1 | 12/2008 | Kuniyil et al. |
| 2009/0137666 A1 | 5/2009 | Wang et al. |
| 2009/0171330 A1 | 7/2009 | Taylor et al. |
| 2009/0204111 A1 | 8/2009 | Bissig et al. |
| 2009/0218550 A1 | 9/2009 | Koyakutty et al. |
| 2009/0237648 A1 | 9/2009 | Armstrong et al. |
| 2009/0263485 A1 | 10/2009 | Li et al. |
| 2009/0281536 A1 | 11/2009 | Beckman et al. |
| 2009/0285766 A1 | 11/2009 | Kishen et al. |
| 2009/0294692 A1 | 12/2009 | Bourke, Jr. et al. |
| 2009/0304581 A1 | 12/2009 | Scheinberg et al. |
| 2010/0016783 A1 | 1/2010 | Bourke, Jr. et al. |
| 2010/0045778 A1 | 2/2010 | Yelin |
| 2010/0166650 A1 | 7/2010 | Gambhir |
| 2010/0197937 A1 | 8/2010 | Minami et al. |
| 2010/0211137 A1 | 8/2010 | Kim et al. |
| 2010/0233147 A1 | 9/2010 | Schwartz et al. |
| 2010/0255599 A1 | 10/2010 | Drake et al. |
| 2010/0279272 A1 | 11/2010 | Burrell et al. |
| 2010/0322471 A1 | 12/2010 | Treado et al. |
| 2011/0020239 A1 | 1/2011 | Bulte et al. |
| 2011/0021970 A1 | 1/2011 | Vo-Dinh et al. |
| 2011/0045081 A1 | 2/2011 | Steitz et al. |
| 2011/0123439 A1 | 5/2011 | Cheon et al. |
| 2011/0152692 A1 | 6/2011 | Nie et al. |
| 2011/0165077 A1 | 7/2011 | Qian et al. |
| 2011/0182881 A1 | 7/2011 | Chin et al. |
| 2011/0190760 A1 | 8/2011 | Niver et al. |
| 2011/0207231 A1 | 8/2011 | Natan et al. |
| 2011/0230760 A1 | 9/2011 | Gambhir et al. |
| 2011/0242533 A1 | 10/2011 | Treado et al. |
| 2011/0261351 A1 | 10/2011 | Treado et al. |
| 2011/0262351 A1 | 10/2011 | Chung et al. |
| 2011/0263920 A1 | 10/2011 | Bourke, Jr. et al. |
| 2011/0282181 A1 | 11/2011 | Wang et al. |
| 2012/0123205 A1 | 5/2012 | Nie et al. |
| 2012/0136241 A1 | 5/2012 | Chen et al. |
| 2012/0141380 A1 | 6/2012 | Margel et al. |
| 2012/0141981 A1 | 6/2012 | Pantazis et al. |
| 2012/0164624 A1 | 6/2012 | Natan et al. |
| 2012/0164680 A1 | 6/2012 | McNaughton et al. |
| 2012/0179029 A1 | 7/2012 | Kircher et al. |
| 2012/0212733 A1 | 8/2012 | Kodali et al. |
| 2012/0226139 A1 | 9/2012 | Peyman |
| 2012/0251450 A1 | 10/2012 | Punnoose et al. |
| 2012/0282632 A1 | 11/2012 | Chiu et al. |
| 2012/0283379 A1 | 11/2012 | Auger et al. |
| 2012/0302940 A1 | 11/2012 | Ray |

(56) References Cited

U.S. PATENT DOCUMENTS

| | | |
|---|---|---|
| 2013/0012794 A1 | 1/2013 | Zeng et al. |
| 2013/0023770 A1 | 1/2013 | Courtney et al. |
| 2013/0029360 A1 | 1/2013 | Suh et al. |
| 2013/0040292 A1 | 2/2013 | Lopez et al. |
| 2013/0137944 A1 | 5/2013 | Jeong et al. |
| 2013/0231573 A1 | 9/2013 | Zeng et al. |
| 2013/0309280 A1 | 11/2013 | Choi et al. |
| 2013/0330839 A1 | 12/2013 | Suh et al. |
| 2013/0342683 A1 | 12/2013 | Nelson et al. |
| 2014/0140594 A1 | 5/2014 | Mahadevan-Jansen et al. |
| 2014/0316255 A1 | 10/2014 | Garai et al. |
| 2014/0350534 A1 | 11/2014 | Kircher et al. |
| 2015/0018807 A1 | 1/2015 | Kircher et al. |
| 2015/0125952 A1 | 5/2015 | Kim et al. |
| 2015/0182296 A1 | 7/2015 | Daon et al. |
| 2015/0258218 A1 | 9/2015 | Kircher et al. |
| 2015/0328346 A1 | 11/2015 | Harmsen et al. |
| 2016/0000329 A1 | 1/2016 | Kircher et al. |
| 2016/0000330 A1 | 1/2016 | Huang et al. |
| 2016/0018404 A1 | 1/2016 | Iyer et al. |
| 2016/0166194 A1 | 6/2016 | Gareau et al. |
| 2017/0138860 A1 | 5/2017 | Huang |
| 2017/0266328 A1 | 9/2017 | Wall et al. |
| 2017/0296293 A1 | 10/2017 | Mak et al. |
| 2018/0271502 A1 | 9/2018 | Zarrine-Afsar |

FOREIGN PATENT DOCUMENTS

| | | |
|---|---|---|
| CN | 102175655 A | 9/2011 |
| CN | 102410994 A | 4/2012 |
| CN | 102686181 A | 9/2012 |
| CN | 102770071 A | 11/2012 |
| CN | 102559190 B | 9/2013 |
| DE | 102 49 674 A1 | 5/2004 |
| DE | 10 2005 030 986 A1 | 1/2007 |
| DE | 10 2011 103 950 A1 | 12/2012 |
| EP | 2671613 A2 | 12/2013 |
| JP | H09-005666 A | 1/1997 |
| JP | H11-084307 A | 3/1999 |
| JP | 2002-534199 A | 9/2002 |
| JP | 2003-503135 A | 1/2003 |
| JP | 2004-193545 A | 7/2004 |
| JP | 2005-306827 A | 11/2005 |
| JP | 2009-011546 A | 1/2009 |
| JP | 2009-508571 A | 3/2009 |
| JP | 2009-511891 A | 3/2009 |
| JP | 2009-115546 A | 5/2009 |
| JP | 2009-222713 A | 10/2009 |
| JP | 2010-523983 A | 7/2010 |
| JP | 2011-158334 A | 8/2011 |
| TW | 572748 B | 1/2004 |
| WO | WO 1990/03803 A1 | 4/1990 |
| WO | WO 1993/03672 A1 | 3/1993 |
| WO | WO 2000/41611 A2 | 7/2000 |
| WO | WO 2001/01854 A2 | 1/2001 |
| WO | WO-01/81923 A1 | 11/2001 |
| WO | WO 2002/100285 A1 | 12/2002 |
| WO | WO 2005/107623 A2 | 11/2005 |
| WO | WO 2008/122035 A1 | 10/2008 |
| WO | WO 2010/096828 A1 | 8/2010 |
| WO | WO 2010/111066 A2 | 9/2010 |
| WO | WO 2011/025640 A1 | 3/2011 |
| WO | WO 2011/084528 A1 | 7/2011 |
| WO | WO 2012/065163 A2 | 5/2012 |
| WO | WO 2012/070893 A2 | 5/2012 |
| WO | WO-2012/166796 A1 | 12/2012 |
| WO | WO 2014/036470 A1 | 3/2014 |
| WO | WO 2014/089247 A2 | 6/2014 |
| WO | WO 2014/100380 A2 | 6/2014 |
| WO | WO 2014/130736 A1 | 8/2014 |
| WO | WO-2015/134620 A1 | 9/2015 |
| WO | WO 2016/028749 A1 | 2/2016 |
| WO | WO 2016/149378 A1 | 9/2016 |
| WO | WO 2016/179260 A1 | 11/2016 |
| WO | WO-2017/040915 A1 | 3/2017 |
| WO | WO 2018/213851 A1 | 11/2018 |

OTHER PUBLICATIONS

Ahmed, M.; Brace, C. L.; Lee, F. T., Jr.; Goldberg, S. N. Principles of and Advances in Percutaneous Ablation. Radiology, 258(2):351-369 (2011).

Amstad, E. et al., Triggered Release from Liposomes through Magnetic Actuation of Iron Oxide Nanoparticle Containing Membranes. Nano Letters, 11:1664-1670 (2011).

Asfari, M.; Janjic, D.; Meda, P.; Li, G.; Halban, P. A.; Wollheim, C. B. Establishment of 2-Mercaptoethanol-Dependent Differentiated Insulin-Secreting Cell Lines. Endocrinology, 130(1):167-178 (1992).

Bogart, L. K. et al., Photothermal Microscopy of the Core of Dextran-Coated Iron Oxide Nanoparticles During Cell Uptake, ACS Nano, 6(7):5961-5971 (2012).

Burckhardt, C. J. and Greber, U. F. Virus Movements on the Plasma Membrane Support Infection and Transmission between Cells, PLoS Pathogens, 5(11):e1000621:1-9 (2009).

Cho, M. H. et al., A magnetic switch for the control of cell death signalling in in vitro and in vivo systems, Nature Materials, 11:1038-1043 (2012).

Cirman, T. et al., Selective Disruption of Lysosomes in Hela Cells Triggers Apoptosis Mediated by Cleavage of Bid by Multiple Papain-Like Lysosomal Cathepsins, Journal of Biological Chemistry, 279(5), 3578-3587 (2004).

Corchero, J. and Villaverde, A., Biomedical applications of distally controlled magnetic nanoparticles, Trends Biotechnol, 27(8):468-476 (2009).

Creixell, M. et al., EGFR-Targeted Magnetic Nanoparticle Heaters Kill Cancer Cells without a Perceptible Temperature Rise. ACS Nano, 5(9):7124-7129 (2011).

Daniel, W. A. and Wojcikowski, J., Lysosomal trapping as an important mechanism involved in the cellular distribution of perazine and in pharmacokinetic interaction with antidepressants. European Neuropsychopharmacology, 9:483-491 (1999).

Dobson, J., Remote control of cellular behaviour with magnetic nanoparticles, Nature Nanotechnology, 3:139-143 (2008).

Domenech, M. et al., Lysosomal Membrane Permeabilization by Targeted Magnetic Nanoparticles in Alternating Magnetic Fields, ACS Nano, 7(6):5091-5101 (2013).

El-Dakdouki, M. H. et al., Development of Multifunctional Hyaluronan-Coated Nanoparticles for Imaging and Drug Delivery to Cancer Cells, Biomacromolecules, 13:1144-1151 (2012).

Eto, K. et al., Glucose metabolism and glutamate analog acutely alkalinize pH of insulin secretory vesicles of pancreatic beta-cells, Am. J. Physiol. Endocrinol. Metab., 285:E262-E271 (2003).

Gaster, R. S. et al., Matrix-insensitive protein assays push the limits of biosensors in medicine, Nature Medicine, 15(11):1327-1332 (2009).

Ghosh, D. et al., M13-templated magnetic nanoparticles for targeted in vivo imaging of prostate cancer, Nat. Nanotechnol., 7(10):677-682 (2012).

Grimm, J. et al., Cell Tracking. Principles and Applications. Radiologue, 47:25-33 (2007). Not in English, Machine Translation included.

Grüttner, C. et al., Synthesis and antibody conjugation of magnetic nanoparticles with improved specific power absorption rates for alternating magnetic field cancer therapy, Journal of Magnetism and Magnetic Materials, 311:181-186 (2007).

Guo, M. et al., Multifunctional superparamagnetic nanocarriers with folate-mediated and pH-responsive targeting properties for anticancer drug delivery, Biomaterials, 32:185-194 (2011).

Gupta, A. K. and Gupta, M., Cytotoxicity suppression and cellular uptake enhancement of surface modified magnetic nanoparticles, Biomaterials, 26,:1565-1573 (2005).

Haun, J. B. et al., Magnetic nanoparticle biosensors, Wiley Interdiscip Rev Nanomed Nanobiotechnol, 2:291-304 (2010).

Haun, J. B. et al., Micro-NMR for Rapid Molecular Analysis of Human Tumor Samples, Science Translation Medicine, 3(71):1-13 (2011) with 2 additional pages of Editor's Summary.

(56) References Cited

OTHER PUBLICATIONS

Haun, J. B. et al., Probing Intracellular Biomarkers and Mediators of Cell Activation Using Nanosensors and Bioorthogonal, ACS Nano, 5(4):3204-3213 (2011).
Hofmann-Amtenbrink, M. et al., Superparamagnetic nanoparticles for biomedical applications, in Nanostructured Materials for Biomedical Applications, pp. 119-149 (2009).
Huang, H. et al., Remote control of ion channels and neurons through magnetic-field heating of nanoparticles, Nature Nanotechnology, 5:602-606 (2010).
International Search Report, International Application No. PCT/US2016/050090, 7 pages, Nov. 22, 2016.
International Search Report, PCT/US15/18746, dated May 27, 2015, 4 pages.
Ivkov, R. et al., Application of High Amplitude Alternating Magnetic Fields for Heat Induction of Nanoparticles Localized in Cancer, Clin Cancer Res, 11(19 Suppl):7093s-7103s (2005).
Kircher, M. F. and Willmann, J. K., Molecular Body Imaging: MR Imaging, CT, and US. Part II. Applications, Radiology, 264(2):349-368 (2012).
Kircher, M. F. et al., A Multimodal Nanoparticle for Preoperative Magnetic Resonance Imaging and Intraoperative Optical Brain Tumor Delineation. Cancer Research, 63:8122-8125 (2003).
Kornhuber, J. et al., Lipophilic Cationic Drugs Increase the Permeability of Lysosomal Membranes in a Cell Culture System, Journal of Cellular Physiology, 224:152-164 (2010).
Kozissnik, B. et al., Magnetic fluid hyperthermia: Advances, challenges, and opportunity, International Journal of Hyperthermia, 29(8):706-714 (2013).
Kumar, C. S.S.R. and Mohammad, F., Magnetic nanomaterials for hyperthermia-based therapy and controlled drug delivery, Advanced Drug Delivery Reviews, 63:789-808 (2011).
Laurent, S. et al., Magnetic fluid hyperthermia: Focus on superparamagnetic iron oxide nanoparticles, Advances in Colloid Interface Science, 166:8-23 (2011).
Lee, J. H. et al., Exchange-coupled magnetic nanoparticles for efficient heat induction, Nature Nanotechnology, 6:418-422 (2011).
Mannix, R. J. et al., Nanomagnetic actuation of receptor-mediated signal transduction, Nature Nanotechnology, 3:36-40 (2008).
Martin, A. L. et al., Synthesis of bombesin-functionalized iron oxide nanoparticles and their specific uptake in prostate cancer cells, J. Nanopart. Res., 12:1599-1608 (2010).
Schulze, K. et al., Uptake and Biocompatibility of Functionalized Poly(vinylalcohol) Coated Superparamagnetic Maghemite Nanoparticles by Synoviocytes InVvitro, Journal of Nanoscience and Nanotechnology, 6:2829-2840 (2006).
Therasse, P. et. al., New guidelines to evaluate the response to treatment in solid tumors, J. Natl. Cancer Inst., 92(3):205-216 (2000).
Tomasini, M. D. et al., Molecular dynamics simulations of rupture in lipid bilayers, Experimental Biology Medicine, 235:181-188 (2010).
Tseng, P. et al., Magnetic nanoparticle-mediated massively parallel mechanical modulation of single-cell behavior, Nature Methods, 9(11):1113-1119 (2012).
Vikman, J. et al., Insulin secretion is highly sensitive to desorption of plasma membrane cholesterol, The FASEB Journal, 23(1):58-67 (2009).
Wahajuddin and Arora, S., Superparamagnetic iron oxide nanoparticles: magnetic nanoplatforms as drug carriers, International Journal of Nanomedicine, 7:3445-3471 (2012).
Written Opinion, International Application No. PCT/US2016/050090, 7 pages, Nov. 22, 2016.
Written Opinion, PCT/US15/18746, 11 pages, May 27, 2015.
Wust, P. et al., Hyperthermia in combined treatment of cancer, The Lancet Oncology, 3:487-497 (2002).
Xu, H. F. et al., Differential Internalization of Superparamagnetic Iron Oxide Nanoparticles in Different Types of Cells, J. Nanoscience Nanotechnology, 10:7406-7410 (2010).
Zhang, E. et al., Alternating Magnetic Fields Trigger Apoptosis by Destruction of Lysosomes with LAMP1-Targeted Nanoparticles, Biophysical Journal, 100(3)(1):472 (2011).
Zhang, E. et al., Dynamic magnetic fields remote-control apoptosis via nanoparticle rotation, ACS Nano, 8(4):3192-3201 (2014).
Extended European Search Report for Application No. EP 13832980.0, dated Apr. 20, 2016.
International Search Report and Written Opinion for Application No. PCT/US2013/057636, dated Jan. 3, 2014.
International Preliminary Report on Patentability for Application No. PCT/US2013/057636, dated Aug. 1, 2014.
International Search Report and Written Opinion for Application No. PCT/US2013/076475, dated Jun. 16, 2014.
Supplementary Partial European Search Report for Application No. EP 14753802.9, dated Oct. 20, 2016.
European Search Report for Application No. EP 14753802.9, dated May 27, 2019.
International Search Report and Written Opinion for Application No. PCT/US2014/017508, dated May 12, 2014.
International Search Report and Written Opinion for Application No. PCT/US2015/045646, dated Nov. 27, 2015.
International Search Report and Written Opinion for Application No. PCT/US2015/042441, dated Oct. 19, 2015.
International Preliminary Report on Patentability for Application No. PCT/US2015/042441, dated Feb. 9, 2017.
Adiseshaiah et al., Nanomaterial standards for efficacy and toxicity assessment. Advanced Review. 2009;2:99-112.
Agarwal et al., Targeted gold nanorod contrast agent for prostate cancer detection by photoacoustic imaging. J. App. Phys. 2007;102:064701-4.
Aggarwal et al., What's fueling the biotech engine-2009-2010. Nat. Biotechnol. 2010;28(11):1165-71.
Akbari et al., Cancer detection using infrared hyperspectral imaging. Cancer Sci. Apr. 2011;102(4):852-7. doi: 10.1111/j.1349-7006.2011.01849.x. Epub Feb. 11, 2011.
Bekis et al., A new agent for sentinel lymph node detection: preliminary results. J Radioanal. Nucl. Chem. 2011;290:277-82. doi: 10.1007/s10967-011-1250-4.
Beljebbar et al., Ex vivo and in vivo diagnosis of C6 glioblastoma development by Raman spectroscopy coupled to a microprobe. Anal. Bioanal. Chem. 2010;398:477-87.
Binkley, J. et al., RNA ligands to human nerve growth factor, Nucleic Acids Research, 1995;23(16):3198-3205.
Bucci, M.K. et al., Near Complete Surgical Resection Predicts a Favorable Outcome in Pediatric Patients with Nonbrainstem, Malignant Gliomas, Cancer, 2004;101(4): 817-824.
Chen et al., Chelator-free synthesis of a dual-modality PET/MRI agent. Angew Chem Int Ed Engl. Dec. 9, 2013;52(50):13319-23. doi: 10.1002/anie.201306306. Epub Oct. 24, 2013.
De La Zerda, A. et al., A Comparison Between Time Domain and Spectral Imaging Systems for Imaging Quantum Dots in Small Living Animals, Molecular Imaging and Biology, 2010;12:500-508.
De La Zerda, A. et al., Advanced contrast nanoagents for photoacoustic molecular imaging, cytometry, blood test and photothermal theranostics, Contrast Media Mol. Imaging, 2011;6:346-369.
De La Zerda, A. et al., Carbon nanotubes as photoacoustic molecular imaging agents in living mice, Letters, Nature Nanotechnology, 2008;3:557-562.
De La Zerda, A. et al., Ultrahigh Sensitivity Carbon Nanotube Agents for Photoacoustic Molecular Imaging in Living Mice, Nano Letters, 2010;10:2168-2172.
Debbage et al., Molecular imaging with nanoparticles: giant roles for dwarf actors. Histochem. Cell. Biol. 2008;130(5):845-75.
Declaration of Moritz Kircher for U.S. Appl. No. 14/464,642, 16 pages, executed Dec. 5, 2016.
Eghtedari, M. et al., High Sensitivity of In Vivo Detection of Gold Nanorods Using a Laser Optoacoustic Imaging System, Nano Letters, 2007;7(7):1914-1918.
Ermilov, S.A. et al., Laser optoacoustic imaging system for detection of breast cancer, Journal of Biomedical Optics, 2009;14(2):024007-1-14.

(56) References Cited

OTHER PUBLICATIONS

Esenturk, E. N. and Walker, A. R. H., Surface-enhanced Raman scattering spectroscopy via aold nanostars, Journal of Raman Spectroscopy, 2009;40(1): 86-91.
Fales et al., Silica-coated gold nanostars for combined surface-enhanced Raman scattering (SERS) detection and singlet-oxygen generation: a potential nanoplatform for theranostics. Langmuir. 2011;27(19):12186-90.
Haaland, D.M. and Easterling, R.G., Improved Sensitivity of Infrared Spectroscopy by the APPiication of Least Squares Methods, APPiied SpectroscoPv, 1980;34(5):539-548.
Harmsen et al., Surface-enhanced resonance Raman scattering nanostars for high-precision cancer imaging. Science Translational Medicine. 2015;7(271):1-8.
Harmsen, S. et al., Rational design of a chalcogenopyrylium-based surface-enhanced resonance Raman scattering nanoprobe with attomolar sensitivity, Nature Communications, 6:6570 I DOI: 10.1038/ncomms7570, pp. 1-9, Additional Information added, 8 pages.
Huang, J. et al., Preparation of Silica-Encapsulated Hollow Gold Nanosphere Tags Using Layer-by-Layer Method for Multiplex Surface-Enhanced Raman Scattering Detection, Langmuir, 2011;27:10228-10233.
Huang, R. et al., High Precision Imaging of Microscopic Spread of Blioblastoma with a Targeted Ultrasensitive SER RS Molecular Imaging Probe, Theranostics, 2016;6(8):1075-84.
Huang, X. et al., Gold nanoparticles: interesting optical properties and recent applications in cancer diaanostics and theraov, Nanomedicine, 2007;2(5):681-693.
Jellinek, D.J. et al., Inhibition of Receptor Binding by High-Affinity RNA Ligands to Vascular Endothelial Growth Factor, Biochemistry, 1994;33:10450-10456.
Kaaki et al., Magnetic Nanocarriers of Doxorubicin Coated with Poly(ethylene glycol) and Folic Acid: Relation between Coating Structure, Surface Properties, Colloidal Stability, and Cancer Cell Targeting, Langmuir, 2012;28:1496-1505.
Kantelhardt et al., Multiphoton Excitation Fluorescence Microscopy of 5- Aminolevulinic Acid Induced Fluorescence in Experimental Gliomas, Laser in Surgery and Medicine, 2008;40:273-281.
Keren et al., Noninvasive molecular imaging of small living subjects using Raman spectroscopy, PNAS, 2008;105(15):5844-5849.
Kim et al., Multifunctional nanstructured materials for multimodal imaging, and simultaneous imaging and therapy. Chem. Soc. Rev. 2009;38:372-90.
Kim et al., lndocyanine-green-embedded PEBBLEs as a contrast agent of photoacoustic imaging, Journal of Biomedical Optics, 2007;12(4):044020-1-8.
Kim et al., Golden carbon nanotubes as multimodal photoacoustic and photothermal high-contrast molecular agents, Nature Nanotechnology, 2009;4:688-694.
Kim et al., Silver-Coated Dye-Embedded Silica Beads: A Core Material of Dual Tagging Sensors Based on Fluorescence and Raman Scattering, ACS Applied Materials & Interfaces, 2011;3:324-330.
Kim et al., Silver-particle-based surface-enhanced resonance Raman scattering spectroscopy for biomolecular sensing and recognition, Anal Bioanal Chem., 2007;388:81-8.
Kircher et al., A brain tumor molecular imaging strategy using a new triple-modality MR1-photoacoustic-Raman nanoparticle, Nature Medicine, 2012;18(5):829-834.
Kircher et al., Noninvasive cell-tracking methods, Nature Reviews: Clinical Oncology, 2011;8:677-688.
Knauth et al., Low-field interventional MRI in neurosurgery: finding the right dose of contrast medium, Neuroradiology, 2001;43:254-258.
Knauth, M. et al., Surgically Induced lntracranial Contrast Enhancement: Potential Source of Diagnostic Error in lntraoperative MR imaging, AJNR Am J Neuroradiol, 1999;20:1547-1553.
Kodali, A., et al., Optimally designed nanolayered metal-dielectric particles as probes for massively multiplexed and ultrasensitive molecular assays, PNAS, 2010;107(31):13620-5.
Koljenovic, S. et al., Raman Spectroscopic Characterization of Porcine Brain Tissue Using a Single Fiber-Optic Probe, Anal. Chem., 2007;79:557-564.
Lee, S. B. et al, Mesoporous silica nanoparticle pretargeting for PET imaging based on a rapid bioorthogonal reaction in a living body. Angew Chem Int Ed Engl. Sep. 27, 2013;52(40):10549-52. doi: 10.1002/anie.201304026. Epub Aug. 16, 2013.
Loening, A.M. and Gambhir, S.S., Amide: A Free Software Tool for Multimodality Medical image Analysis, Molecular imaging, 2003;2(3):131-137.
Ludemann. L. et al., Pharmacokinetic analysis of glioma compartments with dynamic Gd-DTPA-enhanced magnetic resonance imaging, Magnetic Resonance Imaging, 2000;18:1201-1214.
Lusic et al., X-ray-computed tomography contrast agents. Chem. Rev. 2013;113(3):1641-66.
Maeda, H. et al., Tumor vascular permeability and the EPR effect in macromolecular therapeutics: a review, Journal of Controlled Release, 2000;65:271-284.
Mansfield, J.R. et al., Autofluorescence removal, multiplexing, and automated analysis methods for in-vivo fluorescence imaging, Journal of Biomedical Optics, 2005;10(4):041207-1-9.
Massoud et al., Molecular imaging in living subjects: seeing fundamental biological processes in a new light. Genes Dev. 2003;17(5):545-80.
McNay, G. et al., Surface-Enhanced Raman Scattering (SERS) and Surface-Enhanced Resonance Raman Scattering (SERRS): A Review of Applications, Applied Spectroscopy, 2011;65(8):825-837.
Ozawa, T. et al., Bromophenol Blue Staining of Tumors in a Rat Glioma Model, Neurosurgery, 57(4):1041-1047 (2005).
Pelletier, M.J., Quantitative Analysis Using Raman Spectrometry, 2003;57(1):20A-42A.
Popp et al., Raman meets Medicine—Raman spectroscopy: a powerful tool in Biophotonics. Proc. of the SPIE. 2009;7503. 6 pages. doi: 10.1117/12.837623.
Qian, X. et al., In vivo tumor targeting and spectroscopic detection with surface-enhanced Raman nanoparticle tags, Nature Biotechnology, 2008;26(1):83-90.
Razansky, D. et al., Multispectral opto-acoustic tomography of deep-seated fluorescent proteins in vivo, Nature Photonics, 2009;3:412-417.
Reinges et al., Course of brain shift during microsurgical resection of supratentorial cerebral lesions: limits of conventional neuronaviqation, Acta Neurochir, 2004;146:369-377.
Robbins, S.L. and Angell, M., Neoplasia and Other Disturbances of Cell Growth, Basic Pathology: Non-Neoplastic Cell Growth, 1976;2(3):68-105.
Sa et al., Development of Nanoaptamers Using a Mesoporous Silica Model Labeled with 99mTc for Cancer Taraetina, Oncoloav, 2012;82:213-217.
Schneider, J.P. et al., Intraoperative MRI to guide the resection of primary supratentorial glioblastoma multiforme-a quantitative radiological analysis, Neuroradiology, 2005;47:489-500.
Shinoda, J. et al., Fluorescence-guided resection of glioblastoma multiforme by using high-dose fluorescein sodium, J Neurosurq, 2003;99:597-603.
Short, M.A. et al., Development and preliminary results of an endoscopic Raman probe for potential in vivo diagnosis of lung cancers, Optics Letters, 2008;33(7):711-713.
Stewart et al., Raman Imaging, Annual Review of Analytical Chemistry, 2012;5:337-360.
Stumm Er, W. et al., Fluorescence-guided surgery with 5-aminolevulinic acid for resection of malignant glioma: a randomised controlled multicentre phase III trial, Oncology: The Lancet, 2006;7:392-401.
Stupp, R. et al., Changing Paradigms—An Update on the Multidisciplinary Management of Malignant Glioma, The Oncoloqist, 2006;11:165-180.
Sun, X. et al, Self-Illuminating 64Cu-Doped CdSe/ZnS Nanocrystals in Vivo Tumor Imaging, Journal of the American Chemical Society, 2014;136:1706-1709.
Thakor, A.S. et al., Oxidative Stress Mediates the Effects of Raman-Active Gold Nanoparticles in Human Cells, Nanoparticle Cytotoxicity, 2011;7(1):126-136.

(56) References Cited

OTHER PUBLICATIONS

Thakor, a.S. et al.. The Fate and Toxicity of Raman-Active Silica-Gold Nanoparticles in Mice, Druq Delivery, Science Translation Medicine, 2011;3(79):1-11.

Tognalli, N. et al., From Single to Multiple Ag-Layer Modification of Au Nanocavity Substrates: A Tunable Probe of the Chemical Surface-Enhanced Raman Scattering Mechanism, ACS Nano, 2011;5(7):5433-5443.

Toms, S.A. et al., lntraoperative Optical Spectroscopy Identifies Infiltrating Glioma Margins with High Sensitivity. Operative Neurosurgery, 2005;57(4):382-391.

Tréhin et al., Fluorescen Nanoparticle Uptake for Brain Tumore Visualization. Neoplasia. 2006;8(4):302-11.

Tuerk et al., In vitro evolution of functional nucleic acids: high-affinity RNA ligands of HIV-1 proteins. Gene. 1993;137:33-9.

Von Maltzahn et al., SERS-Coded Gold Nanorods as a Multifuntional Platform for Densely Multiplexed Near-Infrared Imaging and Photothermal Heating, Advanced Material, 2009;21:3175-3180.

Wang, Multiscale photoacoustic microscopy and computer tomography. Nature Photonics. 2009;3:503-9.

Wieboldt, Understanding Raman Spectroscopy Parameters. Spectrscopy, Special Issue. 2010. 6 pages.

Yi, Z. et al, Facile preparation of Au/Ag bimetallic hollow nanospheres and its application in surface-enhanced Raman scatterina, Applied Surface Science, 2011;258(1):212-217.

Yigit et al., In vivo and ex vivo applications of gold nanoparticls for biomedical SERS imaging. Am. J. Nucl. Med. Mol. Imaging. 2012;2(2):323-341.

Yigit, M. V. et al, Noninvasive MRI-SERS Imaging in Living Mice Using an Innately Bimodal Nanomaterial, ACS Nano, 2011;5(2):1056-1066.

Yuan, H. et al., Quantitative Surface-Enhanced Resonant Raman Scattering Multiplexing of Biocompatible Gold Nanostars for in Vitro and ex Vivo Detection, Analytical Chemistry, 2012;85:208-212.

Zavaleta et al., Multiplexed imaging of surface enhanced Raman scattering nanotags in living mice using noninvasive Rama spectroscopy. PNAS. 2009;106(32):13511-6.

Zavaleta et al., Noninvasive Raman Spectroscopy in Living Mice for Evaluation of Tumor Targeting with Carbon Nanotubes. Nano Letters. 2008;8(9):2800-5.

Zavaleta et al., Preclinical Evaluation of Raman Nanoparticle Biodistribution for their Potential Use in Clinical Edoscopy Imaging. Small. 2011;7(15):2232-40.

Zavaleta et al., Raman's "Effect" on Molecular Imaging. J. Nucl. Med. 2011;52:1839-44.

Zhang et al., Molecular Imaging with SERS-Active Nanoparticles. Small. 2011;7(23):3261-9.

Zong, S. et al., A SERS and fluorescence dual mode cancer cell targeting probe based on silica coated AulmAa core-shell nanorods, Talanta, 2012;97:368-375.

* cited by examiner

SYSTEMS AND METHODS FOR TREATMENT OF DISEASE VIA APPLICATION OF MECHANICAL FORCE BY CONTROLLED ROTATION OF NANOPARTICLES INSIDE CELLS

CROSS REFERENCE TO RELATED APPLICATIONS

This application claims the benefit of U.S. Provisional Application No. 62/215,001, filed Sep. 6, 2015, and International (PCT) Application No. PCT/US15/18746, filed Mar. 4, 2015, which claims the benefit of U.S. Provisional Application No. 61/947,830, filed Mar. 4, 2014, and the contents of all of which are hereby incorporated by reference herein in their entireties.

GOVERNMENT SUPPORT

This invention was made with government support under CA016396 awarded by the National Institutes of Health. The government has certain rights in the invention.

FIELD OF THE INVENTION

This invention relates generally to systems and methods that exert targeted mechanical force. In particular embodiments, the invention relates to systems and methods for external control of the movement of magnetic particles with high precision and at significant depths (e.g., 5 to 10 cm, 10 to 20 cm, or 20 to 30 cm) within a subject's body.

BACKGROUND

Investigations using magnetic nanoparticles have explored the capability of controlling the motion or energy of magnetic nanoparticles within cells and tissues by remote application of magnetic fields. So far, this has been investigated using permanent magnets that set nanoparticles in a longitudinal motion, using alternating magnetic fields, or through rotating permanent magnets outside of the tissues of interest. In the latter scenario, the nanoparticles describe circular motions but do not individually rotate around their own axis.
The combination of alternating magnetic fields and magnetic nanoparticles has been used to transform energy into heat. For example, hyperthermia is used as an adjunctive treatment in cancer therapy; here, high-frequency alternating (but not moving) electromagnetic fields in the kilo- to megahertz (kHz-MHz) range have been used to kill cancer cells loaded with engineered magnetic nanoparticles through thermal induction. However, such treatment is not without risks, particularly near thermally sensitive structures such as the gut or gallbladder if nanoparticles are injected systemically, as the heat induction cannot be controlled spatially with high precision and could cause tissue necrosis. Therefore, in contrast to thermal ablation systems, ambient temperature increases greater than 46° C. are not desirable for purposes of remote controlling apoptosis with magnetic fields.

SUMMARY

It is observed that targeted cell death can be achieved by application of mechanical force through rotational movement of magnetic particles in the body of a subject. The present disclosure describes systems and methods for inducing such mechanical force to achieve directed disruption of lysosomes in certain cells, leading to cell death from apoptosis.

The present disclosure describes systems and methods for external control of the movement of magnetic particles with high precision and at significant depths (e.g., 5 to 10 cm, 10 to 20 cm, or 20 to 30 cm) within a subject's body. In particular, in certain embodiments, the system features an alternating current superconductor (ACSC) to greatly enhance the magnetic field amplitude so that the field can penetrate deeper into a body with sufficient amplitude to control movement of the nanoparticles within a working volume.

Among other things, the present disclosure demonstrates use of a dynamic magnetic field (DMF) generator that can induce rotational movement of certain magnetic particles. Particular surprising and advantageous features of the described technology include that it can be used to rotate individual particles, and moreover can rotate such particles about their own axis. Additional or alternative surprising and advantageous features include that the present disclosure provides for manipulation of magnetic particles in a magnetic field without significant heat generation (e.g., without heating the particles).

The disclosure particularly demonstrates that use of magnetic particles designed and/or constructed to specifically bind to a target structure is surprisingly effective, even as compared with use of otherwise comparable (e.g., otherwise identical) magnetic particles that lack such specific binding, for exertion of mechanical force on the target structure.

Specifically exemplified herein is remote induction of cell death by application of mechanical force through rotational movement of magnetic particles (specifically superparamagnetic iron oxide nanoparticles, "SPIONs") exposed to DMF treatment. As exemplified, particles were specifically targeted to lysosomal membrane structures, and were individually induced through application of DMF treatment to rotate about their axes. The resulting mechanical force disrupted (e.g., permeabilized) the lysosomal membranes, releasing lysosomal enzymes and triggering apoptosis, all without heating the particles (or their surroundings).

The Examples included herein demonstrate, among other things, that shear forces created by the generation of torques (incomplete rotation) of magnetic particles (e.g., superparamagnetic nanoparticles such as SPIONs) specifically bound to lysosomal membranes causes membrane permeabilization, and furthermore leads to extravasation of lysosomal contents into the cytoplasm. Still further, the present exemplification demonstrates that such application of shear forces to lysosomal membranes can induce apoptosis.

Still further, the exemplification provided herein explicitly demonstrates that use of specifically targeted magnetic particles (e.g., superparamagnetic nanoparticles such as SPIONs covalently conjugated to specific binding agents that target lysosomal ligands, in particular to antibodies targeting the lysosomal protein marker LAMP1 (LAMP1-SPION)) shows surprisingly superior effect in application of mechanical force as described herein. The present exemplification specifically demonstrates, for example, that remote activation of slow rotation of LAMP1-SPIONs significantly improved the efficacy of cellular internalization of the nanoparticles. LAMP1-SPIONs then preferentially accumulated along the membrane in lysosomes in both rat insulinoma tumor cells and human pancreatic beta-cells, presumably due to binding of LAMP1-SPIONs to endogenous LAMP1. Further activation of torques by the LAMP1-SPIONs bound to lysosomes resulted in rapid decrease in size and number of lysosomes. Without wishing to be bound by any particular theory, it is contemplated that such rapid decrease are attributable to tearing of the lysosomal membrane by the shear force of the rotationally activated LAMP1-SPIONs. Regardless of mechanism, the present exemplification demonstrates that such remote activation resulted in an increased expression of early and late apoptotic markers and impaired cell growth. Findings described herein suggest, among other things, that DMF treatment of lysosome-targeted nanoparticles offers a non-invasive tool to induce apoptosis remotely.

The present disclosure demonstrates, among other things, that use of DMF treatment with appropriate magnetic particles (e.g., with superparamagnetic nanoparticles), and particularly with specifically-targeted such particles, can apply mechanical force in a controlled and effective manner, for use in a wide range of applications, specifically including biomedical applications. In certain embodiments, provided technologies are utilized to induce apoptosis or otherwise to achieve cell death or destruction, including of tumor cells, malignant cells, or otherwise aberrantly proliferating cells.

One particular advantage of technologies described herein is that mechanical force is applied, and appropriate results achieved, without significant generation of heat. Thus, for example, in certain embodiments, the present disclosure provides compositions and methods that achieve selective cell destruction without significant generation of heat. In particular, provided technologies apply mechanical force, and in certain embodiments, achieve selective cell destruction, without generating heat sufficient to result in off-target cell damage.

In one aspect, the invention is directed to an alternating current superconductor (ACSC) system for external control of the movement of magnetic particles within the body of a subject, the system comprising: an alternating current (AC) power source for powering the system; a controller for controlling a dynamic magnetic field produced by the system; a cooling unit for cooling the system; and an actuator comprising superconducting windings, wherein the actuator has a geometry operable to apply the dynamic magnetic field to a working volume of known geometry within the body of a subject, and wherein the dynamic magnetic field is from about 0.1 T to about 3 T to induce movement of particles located within the working volume in the body of the subject.

In certain embodiments, the controller comprises an inverter. In certain embodiments, the cooling unit comprises a cryogenic cooling unit. In certain embodiments, the windings comprise a high temperature superconductor material coated conductor. In certain embodiments, the high temperature superconductor material comprises $YBa_2Cu_3O_x$ (YBCO). In certain embodiments, the induced movement includes rotation.

In certain embodiments, the particles comprise superparamagnetic nanoparticles.

In certain embodiments, the working volume extends to a maximum depth in a range selected from the group consisting of greater than 1 cm, greater than 2 cm, greater than 3 cm, between 5 to 10 cm, between 10 to 20 cm, and between 20 to 30 cm from an accessible surface of the subject.

In certain embodiments, the surface of the subject comprises skin of the subject or the interior surface of an accessible cavity of the subject.

In certain embodiments, the system comprises particles for binding to a target structure. In certain embodiments, a mechanical force within the range of about 1 fN to about 1 nN is applied to the target structure of the subject, but the particles are not significantly heated. In certain embodiments, a mechanical force within the range of about 1 pN to about 1 fN is applied to the target structure of the subject, but the particles are not significantly heated.

In another aspect, the invention is directed to a method of operating an alternating current superconductor (ACSC) system for external control of the movement of magnetic particles within the body of a subject, the system comprising: an alternating current (AC) power source for powering the system; a controller for controlling a dynamic magnetic field produced by the system; a cooling unit for cooling the system; and an actuator comprising superconducting windings, wherein the actuator has a geometry operable to apply the dynamic magnetic field to a working volume of known geometry within the body of a subject, and wherein the dynamic magnetic field is from about 0.1 T to about 3 T to induce movement of particles located within the working volume in the body of the subject, the method comprising: remotely controlling application of the dynamic field produced by the system to induce movement of particles located within the working volume in the body of the subject.

In certain embodiments, controlling is performed by Internet, by WLAN, or otherwise. In certain embodiments, the induced movement comprises rotation.

In certain embodiments, the particles comprise superparamagnetic nanoparticles.

In certain embodiments, the working volume extends to a maximum depth selected from the range consisting of greater than 1 cm from an accessible surface of the subject, greater than 2 cm from an accessible surface of the subject, greater than 3 cm from an accessible surface of the subject, between 5 to 10 cm from an accessible surface of the subject, between 10 to 20 cm from an accessible surface of the subject, and between 20 to 30 cm from an accessible surface of the subject.

In certain embodiments, the surface of the subject comprises skin of the subject or the interior surface of an accessible cavity of the subject.

In certain embodiments, the ACSC system is operated under 50 Hz. In certain embodiments, the ACSC system is operated under 30 Hz. In certain embodiments, the ACSC system is operated from about 10 Hz to 30 Hz. In certain embodiments, the ACSC system is operated at about 20 Hz.

In certain embodiments, a mechanical force within the range of about 1 fN to about 1 nN is applied to a target structure of the subject. In certain embodiments, a mechanical force within the range of about 1 pN to 1 fN is applied to a target structure of the subject.

In certain embodiments, the particles are or comprise nanoparticles. In certain embodiments, the particles are or comprise superparamagnetic nanoparticles. In certain embodiments, the particles are or comprise iron oxide nanoparticles ("SPIONs"). In certain embodiments, the particles are or comprise superparamagnetic nanoparticles characterized by an iron oxide core. In certain embodiments, the particles lose their magnetism when not exposed to an external magnetic field. In certain embodiments, the particles are superparamagnetic nanoparticles associated with a targeting agent that specifically binds to the target structure. In certain embodiments, the particles are bound to a target structure in the body of the subject. In certain embodiments, the particles are bound to a target structure in the body of the subject, and a lysosomal membrane and the superparamagnetic nanoparticles are associated with a targeting agent that specifically binds to the target structure. In certain embodiments, the particles are not significantly heated such that no tissue damage is caused by generated heat.

In certain embodiments, the targeting agent is covalently linked to the magnetic nanoparticles. In certain embodiments, the targeting agent is or comprises a member selected from the group consisting of an antibody agent, a polypeptide, a small molecule, a glycan, a lipid, and a nucleic acid that specifically binds to a target moiety in or on the target structure. In certain embodiments, the target structure is or comprises a member selected from the group consisting of a cell membrane, a tumor-associated entity, a tumor-associated marker, an ion channel, an intracellular membrane, a lysosomal membrane, an intracellular entity such as an organelle such as the endoplasmic reticulum (ER), the golgi apparatus, the mitochondria, a component of transcription machinery, a splicosome, a ribosome, and combinations thereof. In certain embodiments, the targeting agent is covalently linked to the magnetic nanoparticles. In certain embodiments, the targeting agent specifically binds to a target moiety on the surface of the lysosomal membrane. In certain embodiments, the target moiety is or comprises LAMP-1 (CD107a), LAMP-2 (CD107b), or LAMP-3 (CD63).

In certain embodiments, the method comprises exposing a target structure to the magnetic nanoparticles so that the nanoparticles bind to the target structure with a density sufficient to apply a desired force across a relevant area. In certain embodiments, the exposed target structure is coincident with the working volume or is within the working volume.

In certain embodiments, the method comprises exposing the target structure to the magnetic nanoparticles so that, on average, from about 1 to about 60 magnetic nanoparticles become bound to each lysosome. In certain embodiments, the step of exposing comprises exposing the target structure to the magnetic nanoparticles so that, on average, from about 10 to about 50 magnetic nanoparticles become bound to each lysosome. In certain embodiments, the step of exposing comprises exposing the target structure to the magnetic nanoparticles so that, on average, about 30 magnetic nanoparticles become bound to each lysosome.

In certain embodiments, the method comprises applying a DMF field with a strength within the range of about 1 mT to 1 T.

In another aspect, the invention is directed to a method of applying mechanical force to a target structure, the method comprising: exposing a target structure to magnetic particles so that the particles bind to the target structure; and applying a dynamic magnetic field (DMF) to the nanoparticles sufficient to induce movement of the particles.

In certain embodiments, the induced movement comprises rotation.

In certain embodiments, a mechanical force within a range of from about 1 fN to about 1 nN is applied to the target structure without the particles being significantly heated.

In certain embodiments, the particles are or comprise nanoparticles. In certain embodiments, the particles are or comprise magnetic nanoparticles. In certain embodiments, the particles are or comprise iron oxide nanoparticles ("SPIONs"). In certain embodiments, the magnetic nanoparticles are characterized by an iron oxide core. In certain embodiments, the particles are characterized in losing their magnetism when not exposed to an external magnetic field. In certain embodiments, the particles are characterized in maintaining their magnetism when not exposed to an external magnetic field. In certain embodiments, the magnetic nanoparticles are associated with a targeting agent that specifically binds to the target structure.

In certain embodiments, the targeting agent is covalently linked to the magnetic nanoparticles. In certain embodiments, the targeting agent is or comprises an antibody agent. In certain embodiments, the targeting agent is or comprises a member selected from the group consisting of a polypeptide, a small molecule, a glycan, a lipid, a nucleic acid that specifically binds to a target moiety in or on the target structure, and combinations thereof. In certain embodiments, the target moiety is or comprises a polypeptide. In certain embodiments, the target moiety is or comprises a glycan. In certain embodiments, the target moiety is or comprises a nucleic acid.

In certain embodiments, the target structure is or comprises a cell membrane. In certain embodiments, the target structure is or comprises a tumor-associated marker. In certain embodiments, the target structure is or comprises an ion channel. In certain embodiments, the target structure is or comprises an intracellular membrane. In certain embodiments, the target structure is or comprises a lysosomal membrane. In certain embodiments, the target structure is or comprises an intracellular entity.

In certain embodiments, the intracellular entity is or comprises an organelle. In certain embodiments, the organelle is selected from the group consisting of the endoplasmic reticulum (ER), the golgi apparatus, the mitochondria, and combinations thereof. In certain embodiments, the intracellular entity is or comprises a component of transcription machinery, a splicosome, or a ribosome.

In certain embodiments, the target structure is or comprises a lysosomal membrane and the magnetic nanoparticles are associated with a targeting agent that specifically binds to the target structure.

In certain embodiments, the targeting agent is covalently linked to the magnetic nanoparticles. In certain embodiments, the targeting agent specifically binds to a target moiety on the surface of the lysosomal membrane. In certain embodiments, the target moiety is or comprises LAMP-1 (CD107a), LAMP-2 (CD107b), or LAMP-3 (CD63).

In certain embodiments, the step of exposing comprises exposing the target structure to the magnetic nanoparticles so that the nanoparticles bind to the target structure with a density sufficient to apply a desired force across a relevant area. In certain embodiments, the step of exposing comprises exposing the target structure to the magnetic nanoparticles so that, on average, about 1 to about 60 magnetic nanoparticles become bound to each lysosome. In certain embodiments, the step of exposing comprises exposing the target structure to the magnetic nanoparticles so that, on average, about 10 to about 50 magnetic nanoparticles become bound to each lysosome. In certain embodiments, the step of exposing comprises exposing the target structure to the magnetic nanoparticles so that, on average, about 30 magnetic nanoparticles become bound to each lysosome.

In certain embodiments, the step of applying DMF treatment comprises applying a DMF field with a strength within the range of about 1 mT to 5 T. In certain embodiments, the step of applying DMF treatment comprises applying a DMF field with a reach within the range of about mm to about cm. In certain embodiments, the step of applying DMF treatment comprises applying a DMF field with a reach of at least 1 cm. In certain embodiments, the step of applying DMF treatment comprises applying a DMF field with a reach of at least 2 cm to 5 cm. In certain embodiments, the step of applying DMF treatment comprises applying a DMF field with a reach of at least 10 cm (e.g., at least 15 cm, at least 18 cm, at least 20 cm, at least 23 cm, at least 25 cm, at least 28 cm, or at least 30 cm). In certain embodiments, the step of applying DMF treatment comprises applying a DMF field with a reach of at least 50 cm.

In certain embodiments, the target structure is or comprises a tumor-associated entity. In certain embodiments, the tumor-associated entity is or comprises a cell-surface entity. In certain embodiments, the tumor-associated entity is or comprises and intracellular entity.

In another aspect, the invention is directed to a dynamic magnetic field (DMF) system for external control of the movement of magnetic particles within the body of a subject, the system comprising: a DMF generator comprising an array of multiphase coils; a controller for regulating frequency and magnetic flux; and the magnetic particles (e.g., SPIONs).

In another aspect, the invention is directed to a composition for use with an alternating current superconductor (ACSC) system for external control of the movement of magnetic particles within the body of a subject, the composition comprising superparamagnetic nanoparticles.

In certain embodiments, the composition is or comprises iron oxide nanoparticles ("SPIONs"). In certain embodiments, the nanoparticles are or comprise superparamagnetic nanoparticles characterized by an iron oxide core. In certain embodiments, the composition further comprises superparamagnetic nanoparticles associated with a targeting agent that specifically binds to a target structure in the body of the subject.

In certain embodiments, the nanoparticles are bound to a target structure in the body of the subject, and a lysosomal membrane and the superparamagnetic nanoparticles are associated with a targeting agent that specifically binds to the target structure. In certain embodiments, the nanoparticles comprise a targeting agent covalently linked to the superparamagnetic nanoparticles.

In certain embodiments, the targeting agent is or comprises a member selected from the group consisting of an antibody agent, a polypeptide, a small molecule, a glycan, a lipid, and a nucleic acid that specifically binds to a target moiety in or on the target structure.

In another aspect, the invention is directed to a composition for use with a dynamic magnetic field (DMF) system for external control of the movement of magnetic particles within the body of a subject, the composition comprising superparamagnetic nanoparticles.

Elements of embodiments involving one aspect of the invention (e.g., methods) can be applied in embodiments involving other aspects of the invention, and vice versa.

DESCRIPTION OF THE DRAWINGS

FIG. 2A shows schematic representation of a DMF generator utilized in the present Examples. The device controls rotation and movement of magnetic nanoparticles (e.g., SPIONs) with a low frequency (10-40 Hz) field. In contrast to reported alternating magnetic field generators, the DMF generator causes the nanoparticles to rotate around their own axis.

FIG. 2B illustrates principle of use of the DMF generator and remote induction of apoptosis. As depicted in FIG. 2B, when targeted nanoparticles (LAMP1-SPIONs) first come into contact with cell membranes, their internalization can be enhanced by activation of slow nanoparticle rotation. This causes rotational motion (rolling) of the nanoparticles across the cell membrane and eventually internalization. Once internalized, the LAMP1-SPIONs enter lysosomes and bind to the lysosomal membrane. When the DMF is activated at this point, the nanoparticles start to rotate and the resulting shear forces cause injury to the lysosomal membrane. This in turn causes leakage of the lysosomal contents into the cytoplasm, leading to a decrease in its pH and subsequently apoptosis.

FIG. 4A shows confocal imaging of SPIONs location in INS-1 cells. The SPIONs conjugated with the fluorescent dye TRITC (upper left image) were incubated with living cells in a static magnetic field for 5 minutes. Thereafter the cells were treated by DMF with 20 Hz, for 20 min. and then confocal microscopy images obtained (upper middle image). Plasma membrane and early endosomes were stained with CellMask (upper right image); nuclei and lysosomes were stained with Hoechst 32580 (lower left image) and LysoTracker Green (green, lower middle image), respectively. The squares in the merge stack (lower right image) indicate SPIONs located in the lysosomes. Scale bars=2 μm.

FIG. 4B shows statistical analysis of SPION co-localization with LysoTracker Green and CellMask under same conditions as in FIG. 4A.

FIG. 4C shows co-localization analysis of lysosomes with SPION and CellMask under same conditions as FIG. 4A.

FIG. 4D demonstrates loading efficiency of LAMP1 antibody conjugated SPIONs (LAMP1-SPION) increased under condition with the DMF treatment. The loading efficiency is calculated by the ratio of TRITC fluorescence intensity (lighter greyscale values shown in the merged image) over nuclear intensity. The data was collected from three independent experiments. The "*" symbol indicates $p<0.05$, and "***" symbol indicates $p<0.001$.

FIG. 5A, shows cells (in the lower images) treated by DMF (20 Hz, 20 min.), and lysosomes (in all four images) stained with LysoTracker Green. Scale bars=5 μm.

FIG. 5B shows the mean intensity of fluorescence measured under the various different conditions shown in FIG. 5A.

FIG. 5C shows representative confocal images indicating the intracellular pH value using an acidotropic probe, LysoSensor Green DND 189 in INS-1 cells. Scale bars=5 µm.

FIG. 5D shows the mean intensity of fluorescence measured under the various different conditions shown in FIG. 5C. The data were collected from five experiments with at least 6 cells under each condition. The "" symbol indicates $p<0.01$, and "*" symbol indicates $p<0.001$.

FIG. 7A shows immunostaining of human islet beta cells with or without DMF treatment. Lysosomes were stained with the anti-LAMP1 antibody (two left images), SPIONs with TRITC (two left-center images) and islet beta-cells with an anti-insulin antibody (two right-center images), respectively. Scale bars=2 µm.

FIG. 7B shows the SPIONs located in the membrane of a lysosome in which an intensity profile (right plot) was derived along the horizontal line shown in the stained image (left image).

FIG. 7C shows the SPIONs located in the membrane of a lysosome, after treatment with DMF. An intensity profile (right plot) was also derived based on the horizontal line shown in the corresponding stained image (left).

FIG. 7D illustrates differences in size distribution of lysosomes before (grey bars) and after (black bars) DMF treatment.

FIG. 7E illustrates average sizes of lysosomes without and with DMF treatment. The "***" symbol indicates $p<0.001$.

FIG. 7F shows transmission electron microscopy (TEM) images of the intracellular distribution of SPIONs in INS-1 cells. Images on the bottom are magnified versions of the areas indicated with white boxes (shown in the top images). While without DMF treatment the LAMP1-SPIONs are clustered in vesicular structures, their distribution is scattered throughout the cytosol after DMF treatment.

FIG. 8A shows INS-1 cells treated with DMF for 20 min. at 20 Hz and stained with the nuclear marker Hoechst (shown as grey values in the left image and center-left image), the apoptosis marker annexin V (lighter grey values in the right image) and 7-AAD (lighter grey values in the right image and center-right image). Scale bars=5 µm.

FIGS. 8B and 8C show that after 6 hours of incubation (5% $CO_2$, 37° C.), early (FIG. 8B) and late (FIG. 8C) stage apoptosis were detected by percentage of $$\frac{F_{Annexin\ V(7\_AAD)}}{F_{Hoechst\ 34580}} \times 100$$

number of annexin V and 7-AAD positive cells to the number of Hoechst stained cells. As demonstrated, DMF caused significant increase in apoptosis in LAMP1-SPION-loaded cells compared to when loading was done using conventional SPIONs. Each treatment was conducted with 28 cells. The "*" symbol indicates $p<0.05$.

Figure 8A:
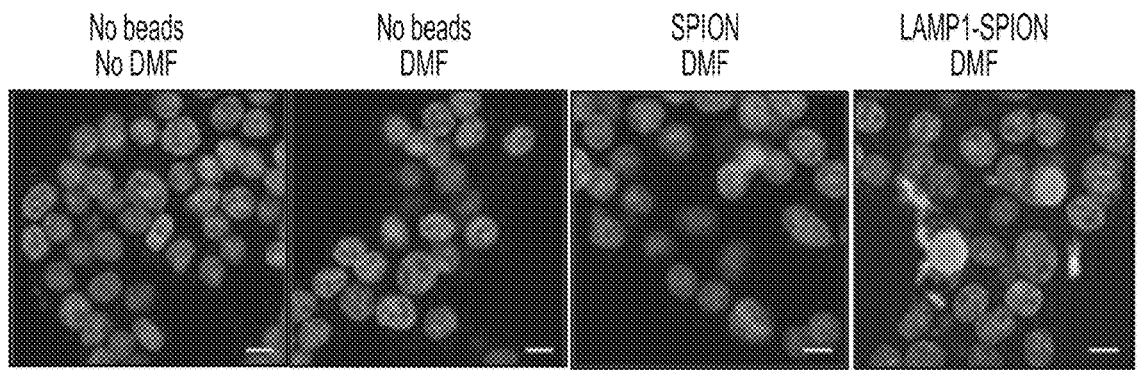
FIGS. 8A-8D demonstrate DMF treatment-induced apoptosis in LAMP1-SPION loaded cells.
Figure 8B:
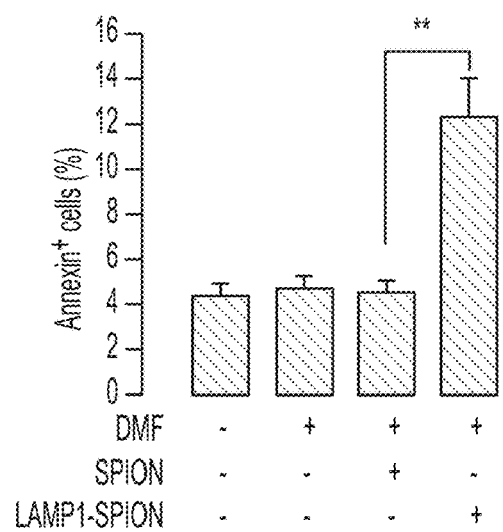
Figure 8C:
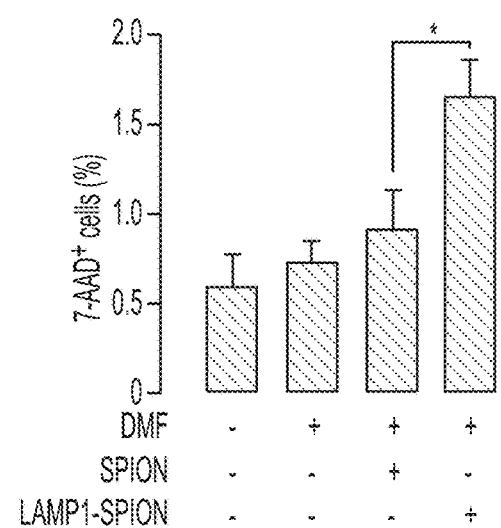
Figure 8D:
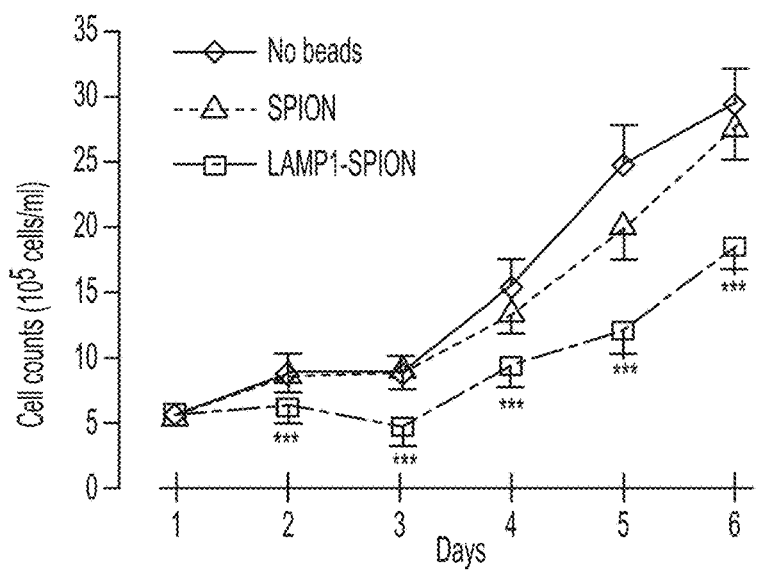

FIG. 8D shows decrease of the rate of cell growth in LAMP1-SPION loaded INS-1 cells. Cells were treated with DMF (20 Hz, 20 minutes) once/day. Data are from 3 independent experiments and represent mean values±S.E.M. The "***" symbol indicates $p<0.001$.

Figure 9:
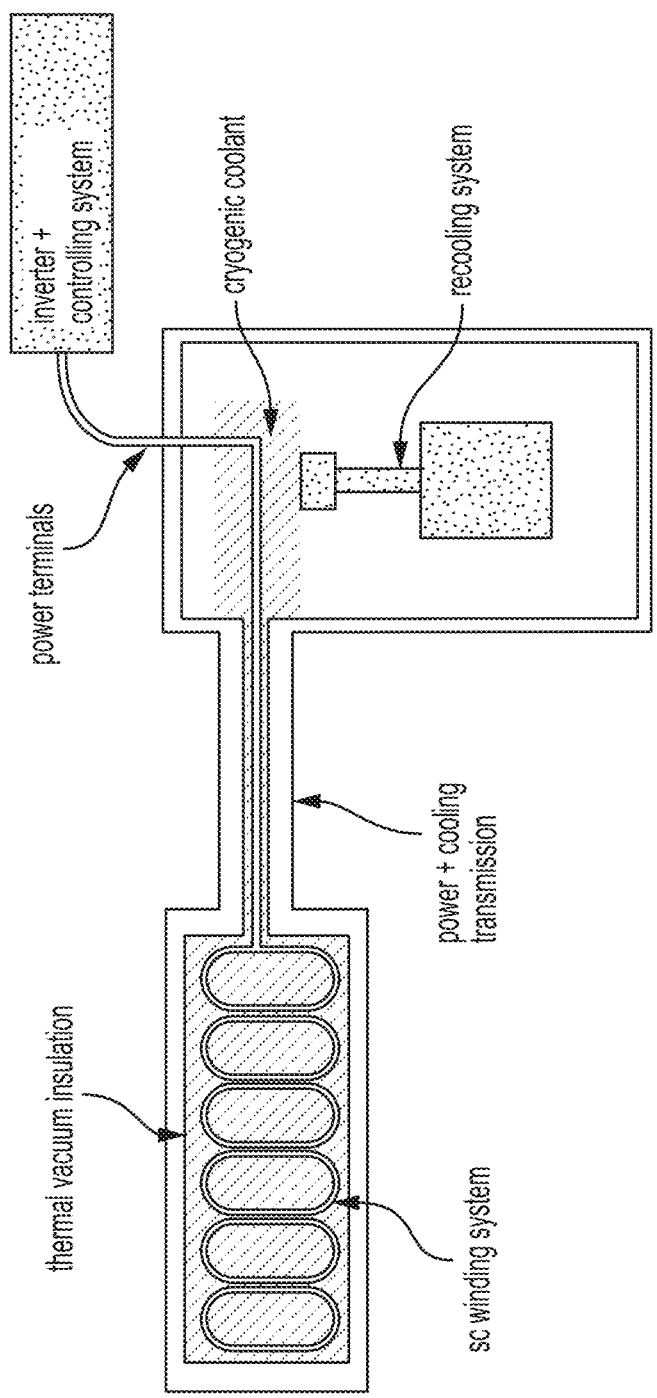

FIG. 9 shows an illustrative ACSC system as described herein.

Figure 10:
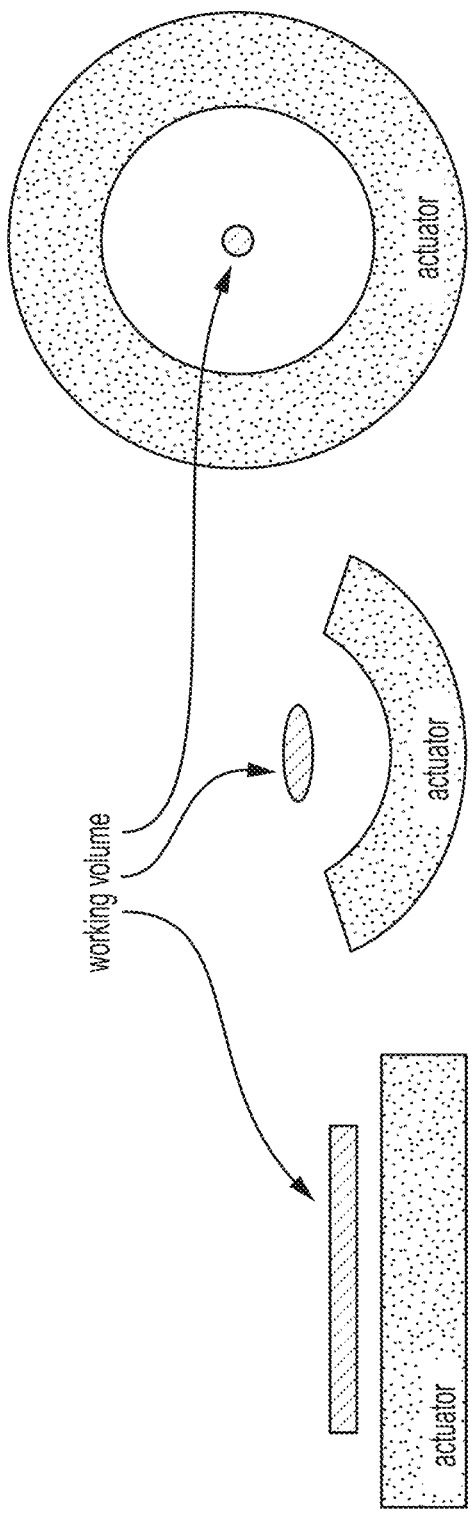

FIG. 10 shows illustrative actuator geometries as described herein.

Figure 11:
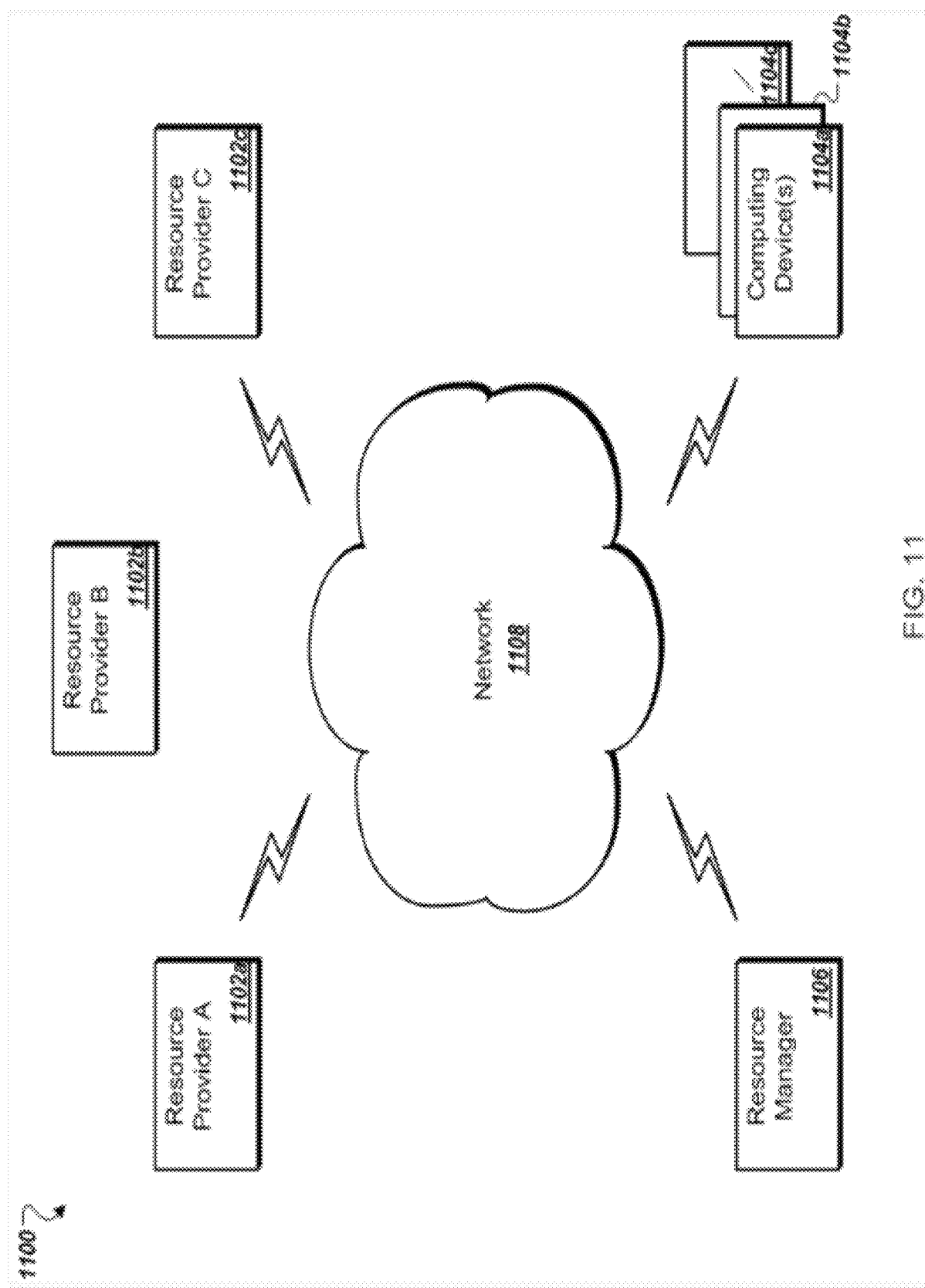

FIG. 11 shows a block diagram of an example network environment for use in the methods and systems described herein, according to an illustrative embodiment of the present disclosure.

Figure 12:
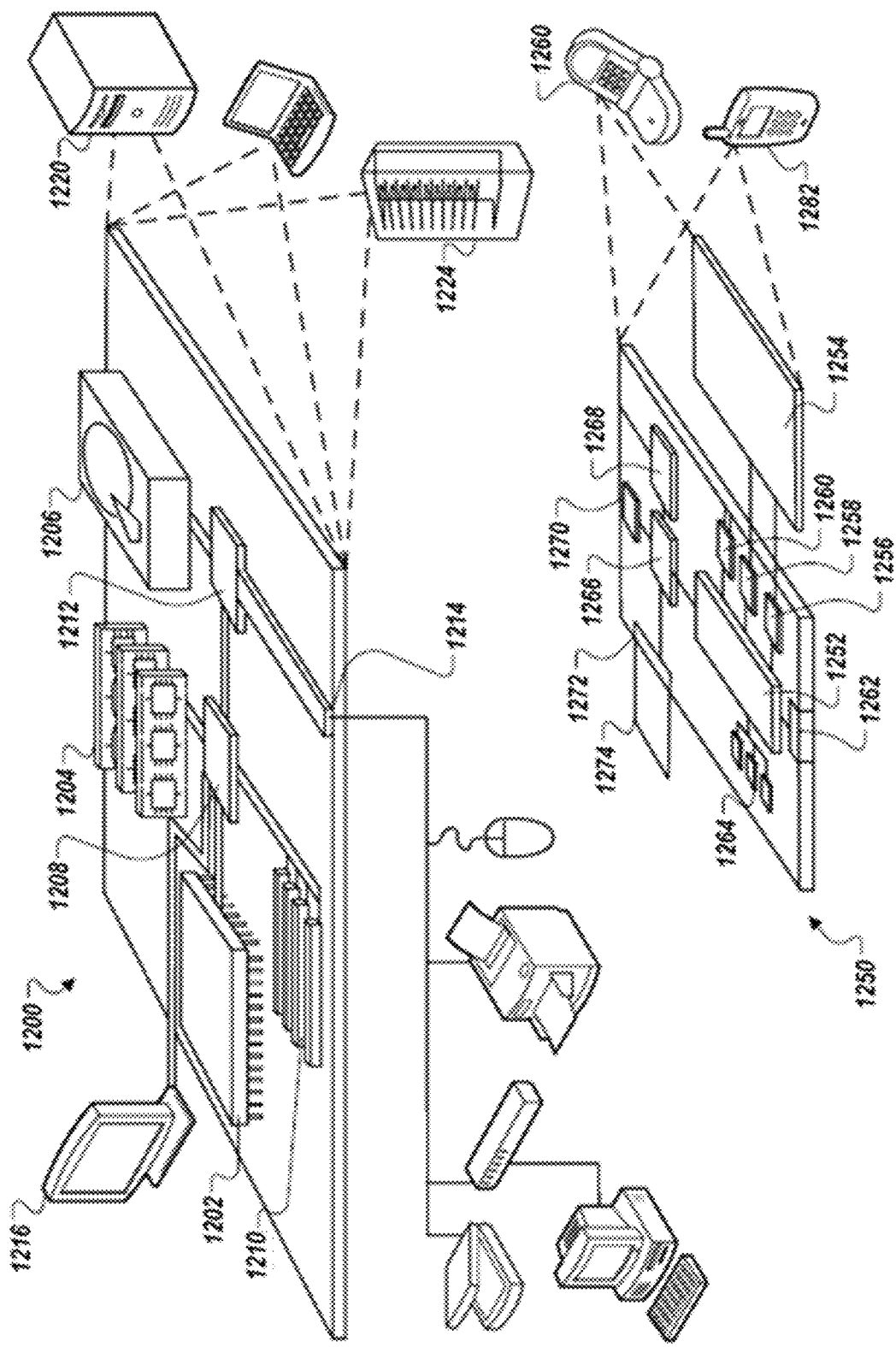

FIG. 12 shows a block diagram of an example computing device and an example mobile computing device, for use in illustrative embodiments of the present disclosure.

Figure 13:
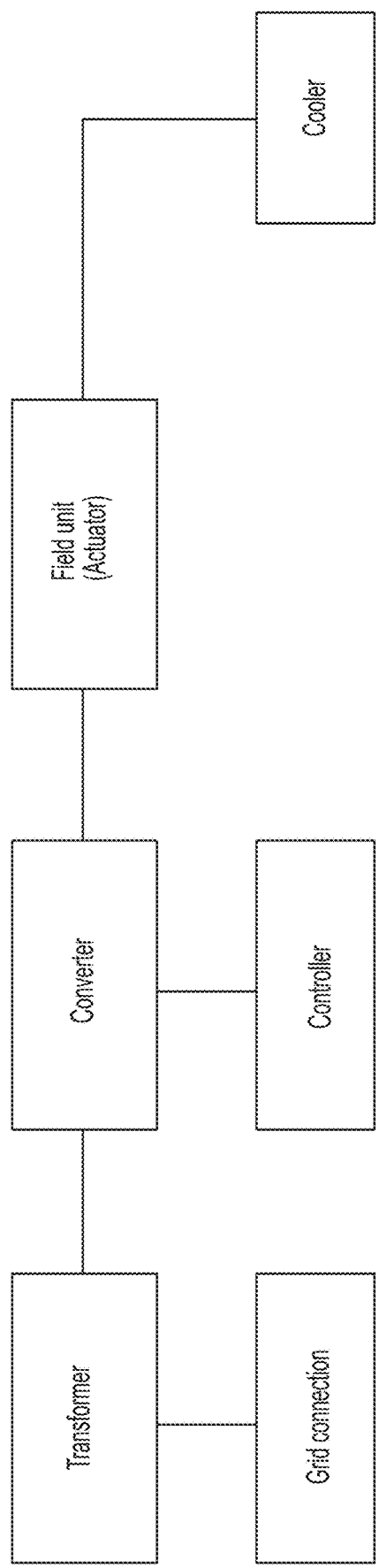

FIG. 13 is a schematic depicting components that can be included in an ACSC system, according to an illustrative embodiment of the present disclosure. Components can include, for example, a transformer, a grid connection, a converter, a controller, a field unit (e.g., actuator), and cooler.

Figure 14:
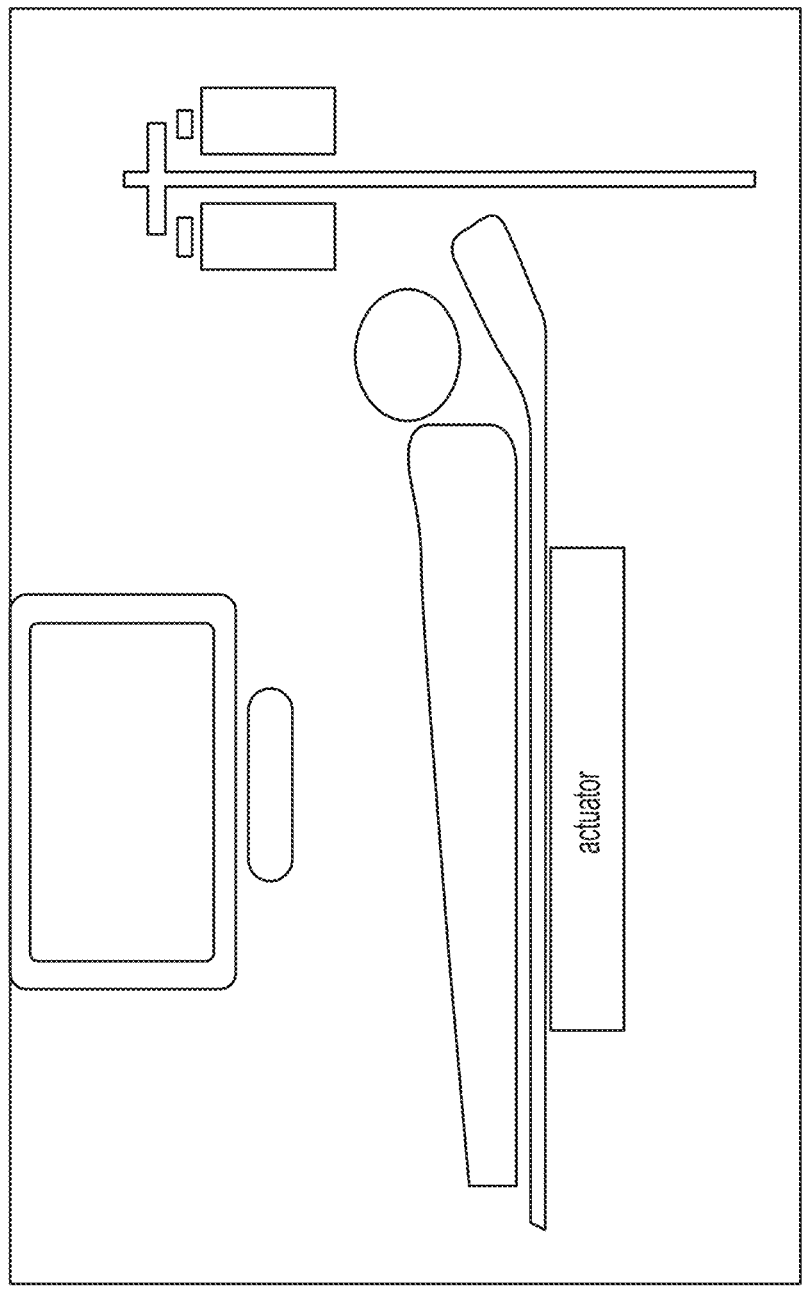

FIG. 14 is a schematic depicting an exemplary system in which an actuator component of an ACSC system is located in proximity to (e.g., underneath) a subject, according to an illustrative embodiment of the present disclosure.

Figure 15:
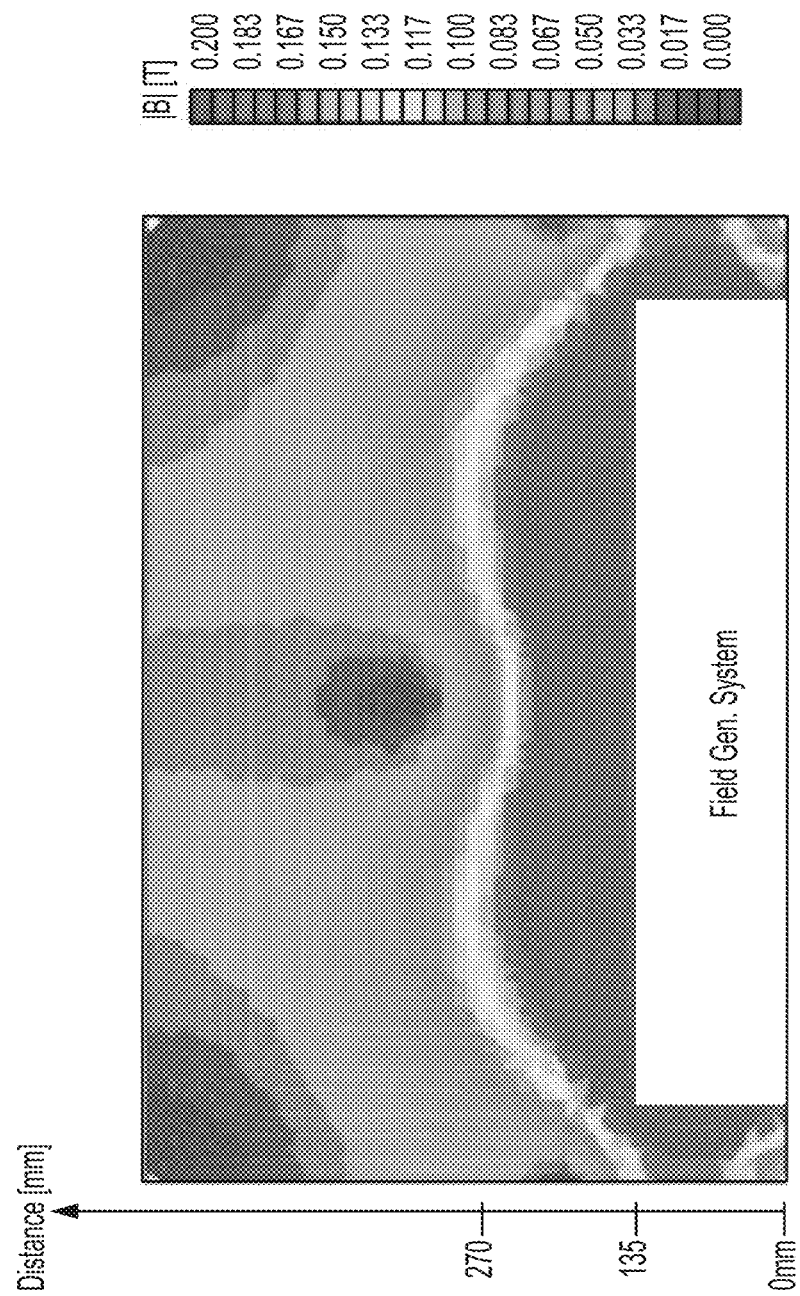

FIG. 15 shows a map profile of the magnetic field (B) as a function of distance (mm) produced by a field generator system as described herein, according to an illustrative embodiment of the present disclosure.

DEFINITIONS

Administration: As used herein, the term "administration" refers to the administration of a composition to a subject or system. Administration to an animal subject (e.g., to a human) may be by any appropriate route. For example, in certain embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

Affinity: As is known in the art, "affinity" is a measure of the tightness with a particular ligand binds to its partner. Affinities can be measured in different ways. In certain embodiments, affinity is measured by a quantitative assay. In some such embodiments, binding partner concentration may be fixed to be in excess of ligand concentration so as to mimic physiological conditions. Alternatively or additionally, in certain embodiments, binding partner concentration and/or ligand concentration may be varied. In some such embodiments, affinity may be compared to a reference under comparable conditions (e.g., concentrations).

Agent: The term "agent" as used herein may refer to a compound or entity of any chemical class including, for example, polypeptides, nucleic acids, saccharides, lipids, small molecules, metals, or combinations thereof. In certain embodiments, an agent is or comprises a natural product in that it is found in and/or is obtained from nature. In certain embodiments, an agent is or comprises one or more entities that is man-made in that it is designed, engineered, and/or produced through action of the hand of man and/or is not found in nature. In certain embodiments, an agent may be utilized in isolated or pure form; in certain embodiments, an agent may be utilized in crude form. In certain embodiments, potential agents are provided as collections or libraries, for example that may be screened to identify or characterize active agents within them. Some particular embodiments of agents that may be utilized in accordance with the present disclosure include small molecules, antibodies, antibody fragments, aptamers, nucleic acids (e.g., siRNAs, shRNAs, DNA/RNA hybrids, antisense oligonucleotides, ribozymes), peptides, peptide mimetics, etc. In certain embodiments, an agent is or comprises a polymer. In certain embodiments, an agent is not a polymer and/or is substantially free of any polymer. In certain embodiments, an agent contains at least one polymeric moiety. In certain embodiments, an agent lacks or is substantially free of any polymeric moiety.

Animal: As used herein, the term "animal" refers to any member of the animal kingdom. In certain embodiments, "animal" refers to humans, at any stage of development. In certain embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In certain embodiments, animals include, but are not limited to, mammals, birds, reptiles, amphibians, fish, and/or worms. In certain embodiments, an animal may be a transgenic animal, genetically-engineered animal, and/or a clone.

Antibody agent: As used herein, the term "antibody agent" refers to an agent that specifically binds to a particular antigen. In certain embodiments, the term encompasses any polypeptide with immunoglobulin structural elements sufficient to confer specific binding. Suitable antibody agents include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibody agent" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. In certain embodiments, the term encompasses stapled peptides. In certain embodiments, the term encompasses one or more antibody-like binding peptidomimetics. In certain embodiments, the term encompasses one or more antibody-like binding scaffold proteins. In come embodiments, the term encompasses monobodies or adnectins. In many embodiments, an antibody agent is or comprises a polypeptide whose amino acid sequence includes one or more structural elements recognized by those skilled in the art as a complementarity determining region (CDR); in certain embodiments an antibody agent is or comprises a polypeptide whose amino acid sequence includes at least one CDR (e.g., at least one heavy chain CDR and/or at least one light chain CDR) that is substantially identical to one found in a reference antibody. In certain embodiments an included CDR is substantially identical to a reference CDR in that it is either identical in sequence or contains between 1-5 amino acid substitutions as compared with the reference CDR. In certain embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In certain embodiments an included CDR is substantially identical to a reference CDR in that it shows at least 96%, 96%, 97%, 98%, 99%, or 100% sequence identity with the reference CDR. In certain embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In certain embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In certain embodiments an included CDR is substantially identical to a reference CDR in that at least one amino acid within the included CDR is substituted as compared with the reference CDR but the included CDR has an amino acid sequence that is otherwise identical with that of the reference CDR. In certain embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In certain embodiments, an antibody agent is or comprises a polypeptide whose amino acid sequence includes structural elements recognized by those skilled in the art as an immunoglobulin variable domain. In certain embodiments, an antibody agent is a polypeptide protein having a binding domain which is homologous or largely homologous to an immunoglobulin-binding domain.

Antibody: As is known in the art, an "antibody" is an immunoglobulin that binds specifically to a particular antigen. The term encompasses immunoglobulins that are naturally produced in that they are generated by an organism reacting to the antigen, and also those that are synthetically produced or engineered. An antibody may be monoclonal or polyclonal. An antibody may be a member of any immunoglobulin class, including any of the human classes: IgG, IgM, IgA, and IgD. A typical immunoglobulin (antibody) structural unit as understood in the art, is known to comprise a tetramer. Each tetramer is composed of two identical pairs of polypeptide chains, each pair having one "light" (approximately 25 kD) and one "heavy" chain (approximately 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains respectively. Each variable region is further subdivided into hypervariable (HV) and framework (FR) regions. The hypervariable regions comprise three areas of hypervariability sequence called complementarity determining regions (CDR 1, CDR 2 and CDR 3), separated by four framework regions (FR1, FR2, FR2, and FR4) which form a beta-sheet structure and serve as a scaffold to hold the HV regions in position. The C-terminus of each heavy and light chain defines a constant region consisting of one domain for the light chain (CL) and three for the heavy chain (CH1, CH2 and CH3). In certain embodiments, the term "full length" is used in reference to an antibody to mean that it contains two heavy chains and two light chains, optionally associated by disulfide bonds as occurs with naturally-produced antibodies. In certain embodiments, an antibody is produced by a cell. In certain embodiments, an antibody is produced by chemical synthesis. In certain embodiments, an antibody is derived from a mammal. In certain embodiments, an antibody is derived from an animal such as, but not limited to, mouse, rat, horse, pig, or goat. In certain embodiments, an antibody is produced using a recombinant cell culture system. In certain embodiments, an antibody may be a purified antibody (for example, by immune-affinity chromatography). In certain embodiments, an antibody may be a human antibody. In certain embodiments, an antibody may be a humanized antibody (antibody from non-human species whose protein sequences have been modified to increase their similarity to antibody variants produced naturally in humans). In certain embodiments, an antibody may be a chimeric antibody (antibody made by combining genetic material from a non-human source, e.g., mouse, rat, horse, or pig, with genetic material from humans).

Antibody fragment: As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in certain embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, and an isolated complementarity determining region (CDR) region. An antigen binding fragment of an antibody may be produced by any means. For example, an antigen binding fragment of an antibody may be enzymatically or chemically produced by fragmentation of an intact antibody and/or it may be recombinantly produced from a gene encoding the partial antibody sequence. Alternatively or additionally, antigen binding fragment of an antibody may be wholly or partially synthetically produced. An antigen binding fragment of an antibody may optionally comprise a single chain antibody fragment. Alternatively or additionally, an antigen binding fragment of an antibody may comprise multiple chains which are linked together, for example, by disulfide linkages. An antigen binding fragment of an antibody may optionally comprise a multimolecular complex. A functional antibody fragment typically comprises at least about 50 amino acids and more typically comprises at least about 200 amino acids.

Antigen: An "antigen" is a molecule or entity that i) elicits an immune response; and/or (ii) is specifically bound by a T cell receptor (e.g., when presented by an MHC molecule) or an antibody (e.g., produced by a B cell), for example when exposed or administered to an organism. In certain embodiments, an antigen elicits a humoral response (e.g., including production of antigen-specific antibodies) in an organism; alternatively or additionally, in certain embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In certain embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In certain embodiments, an antigen binds to an antibody and/or T cell receptor, and may or may not induce a particular physiological response in an organism. In certain embodiments, for example, an antigen may bind to an antibody and/or to a T cell receptor in vitro, whether or not such an interaction occurs in vivo. In general, an antigen may be or include any chemical entity such as, for example, a small molecule, a nucleic acid, a polypeptide, a carbohydrate, a lipid, a polymer [in certain embodiments other than a biologic polymer (e.g., other than a nucleic acid or amino acid polymer)] etc. In certain embodiments, an antigen is or comprises a polypeptide. In certain embodiments, an antigen is or comprises a glycan. Those of ordinary skill in the art will appreciate that, in general, an antigen may be provided or utilized in isolated or pure form, or alternatively may be provided in crude form (e.g., together with other materials, for example in an extract such as a cellular extract or other relatively crude preparation of an antigen-containing source). In certain embodiments. In certain embodiments, an antigen is or comprises a recombinant antigen. In certain embodiments, an antigen is or comprises a polypeptide or portion thereof. In certain embodiments, an antigen is associated with (e.g., expressed by) an infectious agent. In certain embodiments, an antigen is associated with cancer (e.g., with tumor cells and/or metastases).

Approximately: As used herein, the terms "approximately" and "about" are each intended to encompass normal statistical variation as would be understood by those of ordinary skill in the art as appropriate to the relevant context. In certain embodiments, the terms "approximately" or "about" each refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

Aptamer: As used herein, the term "aptamer" refers to a macromolecule composed of nucleic acid (e.g., RNA, DNA) that binds tightly to a specific molecular target (e.g., an umbrella topology glycan). A particular aptamer may be described by a linear nucleotide sequence and is typically about 15-60 nucleotides in length. Without wishing to be bound by any theory, it is contemplated that the chain of nucleotides in an aptamer form intramolecular interactions that fold the molecule into a complex three-dimensional shape, and this three-dimensional shape allows the aptamer to bind tightly to the surface of its target molecule. Given the extraordinary diversity of molecular shapes that exist within the universe of all possible nucleotide sequences, aptamers may be obtained for a wide array of molecular targets, including proteins and small molecules. In addition to high specificity, aptamers typically have very high affinities for their targets (e.g., affinities in the picomolar to low nanomolar range for proteins). In many embodiments, aptamers are chemically stable and can be boiled or frozen without loss of activity. Because they are synthetic molecules, aptamers are amenable to a variety of modifications, which can optimize their function for particular applications. For example, aptamers can be modified to dramatically reduce their sensitivity to degradation by enzymes in the blood for use in in vivo applications. In addition, aptamers can be modified to alter their biodistribution or plasma residence time.

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In certain embodiments, two or more entities are physically "associated" with one another if they interact, directly or indirectly, so that they are and remain in physical proximity with one another. In certain embodiments, two or more entities that are physically associated with one another are covalently linked to one another; in certain embodiments, two or more entities that are physically associated with one another are not covalently linked to one another but are non-covalently associated, for example by means of hydrogen bonds, van der Waals interaction, hydrophobic interactions, magnetism, and combinations thereof.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Binding agent: In general, the term "binding agent" is used herein to refer to any entity that binds to a target of interest as described herein. In many embodiments, a binding agent of interest is one that binds specifically with its target in that it discriminates its target from other potential binding partners in a particular interaction contact. In general, a binding agent may be or comprise an entity of any chemical class (e.g., polymer, non-polymer, small molecule, polypeptide, carbohydrate, lipid, nucleic acid, etc.). In certain embodiments, a binding agent is a single chemical entity. In certain embodiments, a binding agent is a complex of two or more discrete chemical entities associated with one another under relevant conditions by non-covalent interactions. For example, those skilled in the art will appreciate that in certain embodiments, a binding agent may comprise a "generic" binding moiety (e.g., one of biotin/avidin/streptaviding and/or a class-specific antibody) and a "specific" binding moiety (e.g., an antibody or aptamers with a particular molecular target) that is linked to the partner of the generic biding moiety. In certain embodiments, such an approach can permit modular assembly of multiple binding agents through linkage of different specific binding moieties with the same generic binding poiety partner. In certain embodiments, binding agents are or comprise polypeptides (including, e.g., antibodies or antibody fragments). In certain embodiments, binding agents are or comprise small molecules. In certain embodiments, binding agents are or comprise nucleic acids. In certain embodiments, binding agents are aptamers. In certain embodiments, binding agents are polymers; in certain embodiments, binding agents are not polymers. In certain embodiments, binding agents are non-polymeric in that they lack polymeric moieties. In certain embodiments, binding agents are or comprise carbohydrates. In certain embodiments, binding agents are or comprise lectins. In certain embodiments, binding agents are or comprise peptidomimetics. In certain embodiments, binding agents are or comprise scaffold proteins. In certain embodiments, binding agents are or comprise mimotopes. In certain embodiments, binding agents are or comprise stapled peptides. In certain embodiments, binding agents are or comprise nucleic acids, such as DNA or RNA.

Characteristic portion: As used herein, the term "characteristic portion" is used, in the broadest sense, to refer to a portion of a substance whose presence (or absence) correlates with presence (or absence) of a particular feature, attribute, or activity of the substance. In certain embodiments, a characteristic portion of a substance is a portion that is found in the substance and in related substances that share the particular feature, attribute or activity, but not in those that do not share the particular feature, attribute or activity. In certain embodiments, a characteristic portion shares at least one functional characteristic with the intact substance. For example, in certain embodiments, a "characteristic portion" of a protein or polypeptide is one that contains a continuous stretch of amino acids, or a collection of continuous stretches of amino acids, that together are characteristic of a protein or polypeptide. In certain embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In certain embodiments, a characteristic portion may be biologically active.

Combination therapy: As used herein, the term "combination therapy" refers to those situations in which a subject is simultaneously exposed to two or more therapeutic regimens (e.g., two or more therapeutic agents). In certain embodiments, two or more agents may be administered simultaneously; in certain embodiments, such agents may be administered sequentially; in certain embodiments, such agents are administered in overlapping dosing regimens.

Comparable: The term "comparable", as used herein, refers to two or more agents, entities, situations, sets of conditions, etc. that may not be identical to one another but that are sufficiently similar to permit comparison therebetween so that conclusions may reasonably be drawn based on differences or similarities observed. In certain embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Corresponding to: As used herein, the term "corresponding to" is often used to designate a structural element or moiety in an agent of interest that shares a position (e.g., in three-dimensional space or relative to another element or moiety) with one present in an appropriate reference agent. For example, in certain embodiments, the term is used to refer to position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the $190^{th}$ residue in the first polymer but rather corresponds to the residue found at the $190^{th}$ position in the reference polymer; those of ordinary skill in the art readily appreciate how to identify "corresponding" amino acids, including through use of one or more commercially-available algorithms specifically designed for polymer sequence comparisons.

Designed: As used herein, the term "designed" refers to an agent (i) whose structure is or was selected by the hand of man; (ii) that is produced by a process requiring the hand of man; and/or (iii) that is distinct from natural substances and other known agents.

Detection entity: The term "detection entity" as used herein refers to any element, molecule, functional group, compound, fragment or moiety that is detectable. In certain embodiments, a detection entity is provided or utilized alone. In certain embodiments, a detection entity is provided and/or utilized in association with (e.g., joined to) another agent. Examples of detection entities include, but are not limited to: various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{64}Cu$, $^{187}Re$, $^{111}In$, $^{90}Y$, $^{99m}Tc$, $^{177}Lu$, $^{89}Zr$, etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In certain embodiments, determining involves manipulation of a physical sample. In certain embodiments, determining involves consideration and/or manipulation of data or information, for example utilizing a computer or other processing unit adapted to perform a relevant analysis. In certain embodiments, determining involves receiving relevant information and/or materials from a source. In certain embodiments, determining involves comparing one or more features of a sample or entity to a comparable reference.

Diagnostic information: As used herein, "diagnostic information" or "information for use in diagnosis" is information that is useful in determining whether a patient has a disease, disorder or condition and/or in classifying a disease, disorder or condition into a phenotypic category or any category having significance with regard to prognosis of a disease, disorder or condition, or likely response to treatment (either treatment in general or any particular treatment) of a disease, disorder or condition. Similarly, "diagnosis" refers to providing any type of diagnostic information, including, but not limited to, whether a subject is likely to have or develop a disease, disorder or condition (such as cancer), state, staging or characteristic of a disease, disorder or condition as manifested in the subject, information related to the nature or classification of a tumor, information related to prognosis and/or information useful in selecting an appropriate treatment. Selection of treatment may include the choice of a particular therapeutic (e.g., chemotherapeutic) agent or other treatment modality such as surgery, radiation, etc., a choice about whether to withhold or deliver therapy, a choice relating to dosing regimen (e.g., frequency or level of one or more doses of a particular therapeutic agent or combination of therapeutic agents), etc.

Dosage form: As used herein, the term "dosage form" refers to a physically discrete unit of an active agent (e.g., a therapeutic or diagnostic agent) for administration to a subject. Each unit contains a predetermined quantity of active agent. In certain embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: As used herein, the term "dosing regimen" refers to a set of unit doses (typically more than one) that are administered individually to a subject, typically separated by periods of time. In certain embodiments, a given therapeutic agent has a recommended dosing regimen, which may involve one or more doses. In certain embodiments, a dosing regimen comprises a plurality of doses each of which are separated from one another by a time period of the same length; in certain embodiments, a dosing regimen comprises a plurality of doses and at least two different time periods separating individual doses. In certain embodiments, all doses within a dosing regimen are of the same unit dose amount. In certain embodiments, different doses within a dosing regimen are of different amounts. In certain embodiments, a dosing regimen comprises a first dose in a first dose amount, followed by one or more additional doses in a second dose amount different from the first dose amount. In certain embodiments, a dosing regimen comprises a first dose in a first dose amount, followed by one or more additional doses in a second dose amount same as the first dose amount. In certain embodiments, a dosing regimen is correlated with a desired or beneficial outcome when administered across a relevant population (i.e., is a therapeutic dosing regimen).

Engineered: In general, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in certain embodiments, an engineered polynucleotide comprises a regulatory sequence that is found in nature in operative association with a first coding sequence but not in operative association with a second coding sequence, is linked by the hand of man so that it is operatively associated with the second coding sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

High affinity binding: The term "high affinity binding", as used herein refers to a high degree of tightness with which a particular ligand binds to its partner. Affinities can be measured by any available method, including those known in the art. Those skilled in the art will be aware of affinities that are appropriately considered to be "high" in a particular context. In certain embodiments, high affinity binding may be characterized by preferentially binding to a particular target when in the presence of alternative potential (e.g., competitive) targets, particularly when such competitive targets are present in excess relative to the target of interest. In certain embodiments, high affinity binding may be characterized by relatively rapid on-rate and/or slow off-rate.

Isolated: As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In certain embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In certain embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. In certain embodiments, isolation involves or requires disruption of covalent bonds (e.g., to isolate a polypeptide domain from a longer polypeptide and/or to isolate a nucleotide sequence element from a longer oligonucleotide or nucleic acid).

Low affinity binding: The term "low affinity binding", as used herein refers to a low degree of tightness with which a particular ligand binds to its partner. As described herein, affinities can be measured by any available method, including methods known in the art. Those skilled in the art will be aware of affinities that are appropriately considered to be "low" in a particular context. In certain embodiments, low affinity binding may be characterized by failure to discriminate among potential (e.g., competitive) targets, particularly when they are present at comparable levels. In certain embodiments, low affinity binding may be characterized by relatively slow on-rate and/or rapid off-rate.

Marker: A marker, as used herein, refers to an entity or moiety whose presence or level is a characteristic of a particular state or event. In certain embodiments, presence or level of a particular marker may be characteristic of presence or stage of a disease, disorder, or condition. To give but one example, in certain embodiments, the term refers to a gene expression product that is characteristic of a particular tumor, tumor subclass, stage of tumor, etc. Alternatively or additionally, in certain embodiments, a presence or level of a particular marker correlates with activity (or activity level) of a particular signaling pathway, for example that may be characteristic of a particular class of tumors. The statistical significance of the presence or absence of a marker may vary depending upon the particular marker. In certain embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present disclosure, a useful marker need not distinguish tumors of a particular subclass with 100% accuracy.

Nucleic acid: As used herein, the term "nucleic acid," in its broadest sense, refers to any compound and/or substance that is or can be incorporated into an oligonucleotide chain. In certain embodiments, a nucleic acid is a compound and/or substance that is or can be incorporated into an oligonucleotide chain via a phosphodiester linkage. As will be clear from context, in certain embodiments, "nucleic acid" refers to individual nucleic acid residues (e.g., nucleotides and/or nucleosides); in certain embodiments, "nucleic acid" refers to an oligonucleotide chain comprising individual nucleic acid residues. In certain embodiments, a "nucleic acid" is or comprises RNA; in certain embodiments, a "nucleic acid" is or comprises DNA. In certain embodiments, a nucleic acid is, comprises, or consists of one or more natural nucleic acid residues. In certain embodiments, a nucleic acid is, comprises, or consists of one or more nucleic acid analogs. In certain embodiments, a nucleic acid analog differs from a nucleic acid in that it does not utilize a phosphodiester backbone. For example, in certain embodiments, a nucleic acid is, comprises, or consists of one or more "peptide nucleic acids", which are known in the art and have peptide bonds instead of phosphodiester bonds in the backbone, are considered within the scope of the present disclosure. Alternatively or additionally, in certain embodiments, a nucleic acid has one or more phosphorothioate and/or 5'-N-phosphoramidite linkages rather than phosphodiester bonds. In certain embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In certain embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In certain embodiments, a nucleic acid comprises one or more modified sugars (e.g., 2'-fluororibose, ribose, 2'-deoxyribose, arabinose, and hexose) as compared with those in natural nucleic acids. In certain embodiments, a nucleic acid has a nucleotide sequence that encodes a functional gene product such as an RNA or protein. In certain embodiments, a nucleic acid includes one or more introns. In certain embodiments, nucleic acids are prepared by one or more of isolation from a natural source, enzymatic synthesis by polymerization based on a complementary template (in vivo or in vitro), reproduction in a recombinant cell or system, and chemical synthesis. In certain embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long.

Pharmaceutical composition: As used herein, the term "pharmaceutical composition" refers to an active agent, formulated together with one or more pharmaceutically acceptable carriers. In certain embodiments, active agent is present in unit dose amount appropriate for administration in a therapeutic regimen that shows a statistically significant probability of achieving a predetermined therapeutic effect when administered to a relevant population. In certain embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: The term "pharmaceutically acceptable" as used herein, refers to agents that, within the scope of sound medical judgment, are suitable for use in contact with tissues of human beings and/or animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Polypeptide: The term "polypeptide", as used herein, generally has its art-recognized meaning of a polymer of at least three amino acids, linked to one another by peptide bonds. In certain embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain. Those of ordinary skill in the art understand that protein sequences generally tolerate some substitution without destroying activity. Thus, in certain embodiments, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide (e.g., a reference polypeptide) is considered to be of the same class as that other polypeptide. In certain embodiments, polypeptides of a particular class all show significant sequence homology or identity with a relevant reference polypeptide. In many embodiments, such member also shares significant activity with the reference polypeptide. For example, in certain embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (i.e., a conserved region, often including a characteristic sequence element) that shows very high sequence identity, often greater than 90% or even 95%, 96%, 97%, 98%, or 99%. Such a conserved region usually encompasses at least 3-4 and often up to 20 or more amino acids; in certain embodiments, a conserved region encompasses at least one stretch of at least 2, 3, 4, 5, 6, 7, 8, 9, 10, 11, 12, 13, 14, 15 or more contiguous amino acids. In certain embodiments, a polypeptide may contain L-amino acids, D-amino acids, or both. In certain embodiments, a polypeptide may contain any of a variety of amino acid modifications or analogs known in the art. For example, in certain embodiments, a polypeptide may include one more modifications such as, e.g., terminal acetylation, amidation, methylation, etc. In certain embodiments, a polypeptide may comprise natural amino acids, non-natural amino acids, synthetic amino acids, and/or combinations thereof. The term "peptide" is generally used to refer to a polypeptide having a length of less than about 100 amino acids, less than about 50 amino acids, less than 20 amino acids, or less than 10 amino acids. In certain embodiments, proteins are antibodies, antibody fragments, biologically active portions thereof, and/or characteristic portions thereof.

Prevention: The term "prevention", as used herein, refers to a delay of onset, and/or reduction in frequency and/or severity of one or more symptoms of a particular disease, disorder or condition. In certain embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition Prognostic and predictive information: As used herein, the terms "prognostic information" and "predictive information" are used to refer to any information that may be used to indicate any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In certain embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In certain embodiments, proteins are antibodies, antibody fragments, biologically active portions thereof, and/or characteristic portions thereof.

Reference: The term "reference" is often used herein to describe a standard or control agent, individual, population, sample, sequence or value against which an agent, individual, population, sample, sequence or value of interest is compared. In certain embodiments, a reference agent, individual, population, sample, sequence or value is tested and/or determined substantially simultaneously with the testing or determination of the agent, individual, population, sample, sequence or value of interest. In certain embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Tumor or subject response may be measured according to a wide variety of criteria, including clinical criteria and objective criteria. Techniques for assessing response include, but are not limited to, clinical examination, positron emission tomatography, chest X-ray CT scan, MRI, ultrasound, endoscopy, laparoscopy, presence or level of tumor markers in a sample obtained from a subject, cytology, and/or histology. Many of these techniques attempt to determine the size of a tumor or otherwise determine the total tumor burden. Methods and guidelines for assessing response to treatment are discussed in Therasse et. al., "New guidelines to evaluate the response to treatment in solid tumors", European Organization for Research and Treatment of Cancer, National Cancer Institute of the United States, National Cancer Institute of Canada, *J. Natl. Cancer Inst.*, 2000, 92(3):205-216. The exact response criteria can be selected in any appropriate manner, provided that when comparing groups of tumors and/or patients, the groups to be compared are assessed based on the same or comparable criteria for determining response rate. One of ordinary skill in the art will be able to select appropriate criteria.

Risk: As will be understood from context, a "risk" of a disease, disorder or condition is a degree of likelihood that a particular individual will develop the disease, disorder, or condition. In certain embodiments, risk is expressed as a percentage. In certain embodiments, risk is from 0, 1, 2, 3, 4, 5, 6, 7, 8, 9, 10 up to 100%. In certain embodiments risk is expressed as a risk relative to a risk associated with a reference sample or group of reference samples. In certain embodiments, a reference sample or group of reference samples have a known risk of a disease, disorder, or condition. In certain embodiments a reference sample or group of reference samples are from individuals comparable to a particular individual. In certain embodiments, relative risk is 0, 1, 2, 3, 4, 5, 6, 7, 8, 9, 10 or more.

Sample: As used herein, the term "sample" typically refers to a biological sample obtained or derived from a source of interest, as described herein. In certain embodiments, a source of interest comprises an organism, such as an animal or human. In certain embodiments, a biological sample is or comprises biological tissue or fluid. In certain embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In certain embodiments, a biological sample is or comprises cells obtained from an individual. In certain embodiments, obtained cells are or include cells from an individual from whom the sample is obtained. In certain embodiments, a sample is a "primary sample" obtained directly from a source of interest by any appropriate means. For example, in certain embodiments, a primary biological sample is obtained by methods selected from the group consisting of biopsy (e.g., fine needle aspiration or tissue biopsy), surgery, collection of body fluid (e.g., blood, lymph, feces etc.), etc. In certain embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Small molecule: As used herein, the term "small molecule" means a low molecular weight organic and/or inorganic compound. In general, a "small molecule" is a molecule that is less than about 5 kilodaltons (kD) in size. In certain embodiments, a small molecule is less than about 4 kD, 3 kD, about 2 kD, or about 1 kD. In certain embodiments, the small molecule is less than about 800 daltons (D), about 600 D, about 500 D, about 400 D, about 300 D, about 200 D, or about 100 D. In certain embodiments, a small molecule is less than about 2000 g/mol, less than about 1500 g/mol, less than about 1000 g/mol, less than about 800 g/mol, or less than about 500 g/mol. In certain embodiments, a small molecule is not a polymer. In certain embodiments, a small molecule does not include a polymeric moiety. In certain embodiments, a small molecule is not a protein or polypeptide (e.g., is not an oligopeptide or peptide). In certain embodiments, a small molecule is not a polynucleotide (e.g., is not an oligonucleotide). In certain embodiments, a small molecule is not a polysaccharide. In certain embodiments, a small molecule does not comprise a polysaccharide (e.g., is not a glycoprotein, proteoglycan, glycolipid, etc.). In certain embodiments, a small molecule is not a lipid. In certain embodiments, a small molecule is a modulating agent. In certain embodiments, a small molecule is biologically active. In certain embodiments, a small molecule is detectable (e.g., comprises at least one detectable moiety). In certain embodiments, a small molecule is a therapeutic.

Specific binding: As used herein, the terms "specific binding" or "specific for" or "specific to" refer to an interaction (typically non-covalent) between a target entity (e.g., a target protein or polypeptide) and a binding agent (e.g., an antibody, such as a provided antibody). As will be understood by those of ordinary skill, an interaction is considered to be "specific" if it is favored in the presence of alternative interactions. In many embodiments, an interaction is typically dependent upon the presence of a particular structural feature of the target molecule such as an antigenic determinant or epitope recognized by the binding molecule. For example, if an antibody is specific for epitope A, the presence of a polypeptide containing epitope A or the presence of free unlabeled A in a reaction containing both free labeled A and the antibody thereto, will reduce the amount of labeled A that binds to the antibody. It is to be understood that specificity need not be absolute. For example, it is well known in the art that numerous antibodies cross-react with other epitopes in addition to those present in the target molecule. Such cross-reactivity may be acceptable depending upon the application for which the antibody is to be used. In particular embodiments, an antibody specific for receptor tyrosine kinases has less than 10% cross-reactivity with receptor tyrosine kinase bound to protease inhibitors (e.g., ACT). One of ordinary skill in the art will be able to select antibodies having a sufficient degree of specificity to perform appropriately in any given application (e.g., for detection of a target molecule, for therapeutic purposes, etc.). Specificity may be evaluated in the context of additional factors such as the affinity of the binding molecule for the target molecule versus the affinity of the binding molecule for other targets (e.g., competitors). If a binding molecule exhibits a high affinity for a target molecule that it is desired to detect and low affinity for non-target molecules, the antibody will likely be an acceptable reagent for immunodiagnostic purposes. Once the specificity of a binding molecule is established in one or more contexts, it may be employed in other, preferably similar, contexts without necessarily re-evaluating its specificity.

Specific: The term "specific", when used herein with reference to an agent or entity having an activity, is understood by those skilled in the art to mean that the agent or entity discriminates between potential targets or states. For example, an agent is said to bind "specifically" to its target if it binds preferentially with that target in the presence of competing alternative targets. In certain embodiments, the agent or entity does not detectably bind to the competing alternative target under conditions of binding to its target. In certain embodiments, the agent or entity binds with higher on-rate, lower off-rate, increased affinity, decreased dissociation, and/or increased stability to its target as compared with the competing alternative target(s).

Stage of cancer: As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

Subject: By "subject" is meant a mammal (e.g., a human, in certain embodiments including prenatal human forms). In certain embodiments, a subject is suffering from a relevant disease, disorder or condition. In certain embodiments, a subject is susceptible to a disease, disorder, or condition. In certain embodiments, a subject displays one or more symptoms or characteristics of a disease, disorder or condition. In certain embodiments, a subject does not display any symptom or characteristic of a disease, disorder, or condition. In certain embodiments, a subject is someone with one or more features characteristic of susceptibility to or risk of a disease, disorder, or condition. A subject can be a patient, which refers to a human presenting to a medical provider for diagnosis or treatment of a disease. In certain embodiments, a subject is an individual to whom therapy is administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition has been diagnosed with and/or exhibits or has exhibited one or more symptoms or characteristics of the disease, disorder, or condition.

Susceptible to: An individual who is "susceptible to" a disease, disorder, or condition (e.g., influenza) is at risk for developing the disease, disorder, or condition. In certain embodiments, an individual who is susceptible to a disease, disorder, or condition does not display any symptoms of the disease, disorder, or condition. In certain embodiments, an individual who is susceptible to a disease, disorder, or condition has not been diagnosed with the disease, disorder, and/or condition. In certain embodiments, an individual who is susceptible to a disease, disorder, or condition is an individual who has been exposed to conditions associated with development of the disease, disorder, or condition. In certain embodiments, a risk of developing a disease, disorder, and/or condition is a population-based risk (e.g., family members of individuals suffering from the disease, disorder, or condition).

Symptoms are reduced: According to the present disclosure, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom.

Therapeutic agent: As used herein, the phrase "therapeutic agent" refers to any agent that elicits a desired pharmacological effect when administered to an organism. In certain embodiments, an agent is considered to be a therapeutic agent if it demonstrates a statistically significant effect across an appropriate population. In certain embodiments, the appropriate population may be a population of model organisms. In certain embodiments, an appropriate population may be defined by various criteria, such as a certain age group, gender, genetic background, preexisting clinical conditions, etc. In certain embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutic regimen: A "therapeutic regimen", as that term is used herein, refers to a dosing regimen whose administration across a relevant population is correlated with a desired or beneficial therapeutic outcome.

Therapeutically effective amount: As used herein, the term "therapeutically effective amount" refers to an amount of a therapeutic protein (e.g., receptor tyrosine kinases antibody) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition (e.g., influenza). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In certain embodiments, treatment may be of a subject who has been diagnosed as suffering from the relevant disease, disorder, and/or condition. In certain embodiments, treatment may be of a subject known to have one or more susceptibility factors that are statistically correlated with increased risk of development of the relevant disease, disorder, and/or condition.

Unit dose: The expression "unit dose" as used herein refers to an amount administered as a single dose and/or in a physically discrete unit of a pharmaceutical composition. In many embodiments, a unit dose contains a predetermined quantity of an active agent. In certain embodiments, a unit dose contains an entire single dose of the agent. In certain embodiments, more than one unit dose is administered to achieve a total single dose. In certain embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In certain embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

DETAILED DESCRIPTION

As described herein, the present disclosure provides technologies that utilize certain magnetic particles, and particularly utilize targeted such particles, to apply mechanical force to a target structure, through application of dynamic magnetic field (DMF) treatment. In particular embodiments, the present disclosure provides technologies for applying mechanical force to cellular membranes and/or to intracellular membranes. In certain embodiments, the present disclosure provides technologies for disrupting or otherwise damaging or injuring (e.g., permeabilizing) cellular membranes and/or intracellular membranes. In certain embodiments, the present disclosure provides technologies for inducing or promoting apoptosis and/or cell death or destruction. In certain embodiments, the present d provides technologies for inducing and/or stimulating apoptosis and/or cell death or destruction in malignant (e.g., cancer, tumor, and/or metastatic) cells.

Among other advantages, provided technologies can achieve application of mechanical force, and particularly can achieve specific application of mechanical force (i.e., to a particular, e.g., preselected, site of interest) without generation of heat. Provided technologies show a variety of advantages as compared with other strategies for inducing and/or stimulating apoptosis and/or cell death or destruction, including those that utilize magnetic particles, many of which generate heat, with undesirable effect(s).

Dynamic Magnetic Field Treatment

Provided technologies utilize magnetic particles (e.g., superparamagnetic, ferromagnetic, or ferrimagnetic particles, particularly nanoparticles) that respond to application of dynamic magnetic field (DMF) treatment.

Certain such particles, superparamagnetic iron oxide nanoparticles ("SPIONs"), have found wide-spread applications in the biomedical field spanning in vitro diagnostic tests such as nanosensors, in vivo imaging and therapies such as magnetic fluid hyperthermia or drug delivery. Recent investigations have also explored the capability of controlling the position or temperature of magnetic nanoparticles (e.g., SPIONs) within cells and tissues by remote application of magnetic fields. So far, this possibility has been investigated using permanent magnets that set nanoparticles in a longitudinal motion, using alternating magnetic fields, or through rotating permanent magnets outside of the tissues of interest. In the latter scenario, the nanoparticles describe circular motions, but do not individually rotate around their own axis. The combination of alternating magnetic fields and magnetic nanoparticles allows one to transform energy into forces or heat. Hyperthermia is used as an adjunctive treatment in cancer therapy; here, high-frequency alternating (but not moving) magnetic fields in the KHz/MHz range have been used to kill cancer cells loaded with magnetic nanoparticles through thermal induction. However, such treatment is not without risks particularly near thermally sensitive structures such as the gut or gallbladder if nanoparticles are injected systemically, as the heat induction cannot be controlled spatially with high precision and could cause tissue necrosis. Therefore, in contrast to thermal ablation systems, ambient temperature increases greater than 46° C. are not desirable for purposes of remote controlling apoptosis with magnetic fields.

Fundamentally different from prior studies using high frequency alternating magnetic fields that cause apoptosis via heat induction, the present disclosure describes a principle of controlling particle rotation and inducing apoptosis via mechanical forces exerted on membranes by targeted particles. Specifically, the present disclosure utilizes dynamic magnetic field (DMF) treatment to induce and precisely control the rotation of magnetic nanoparticles around their own axis. DMF treatment creates a dynamic force field, which is converted inside the particle into a magnetic flux field B, which operates on a particle with a magnetic Moment M and a moment of inertia I. The field generates a torque $\vec{\tau}$ equal to $\vec{\tau} = \mu(\vec{B}) \times \vec{B}$. This approach enables for the first time the ability to induce rotation of individual magnetic particles around their own axis, and furthermore allows precise control of the rotation speed. The present disclosure therefore provides technologies that permit specific application of mechanical force via remote triggering of individual magnetic particle rotation about its own axis. Among other advantages, the present disclosure achieves such rotation, and therefore such application of mechanical force, without generating heat (e.g., without heating the particle).

The present disclosure specifically exemplifies induction of this kind of rotation in certain magnetic particles (e.g., superparamagnetic nanoparticles) bound to a target structure, and demonstrates that it can be used to remotely apply mechanical force to a target structure. The present disclosure particularly demonstrates that such magnetic particles can be targeted to an intracellular site, internalized into cells, and bound to the targeted site. Furthermore, the present disclosure demonstrates that subsequent remote activation of a dynamic magnetic field causes the bound particles to exert mechanical force on the target structure. The particular context exemplified here represents a specific biological application; those skilled in the art will appreciate that the same principle should enable many other new applications in the fields of nanotechnology and nanomedicine.

In certain embodiments, provided technologies do not utilize high-frequency (e.g., above the Hz range, for example in the kHz [sometimes considered to be medium-frequency], MHz, or GHz range) magnetic field oscillations. In many embodiments, provided technologies utilize low-frequency (e.g., within the Hz range) oscillations.

In many embodiments, the present disclosure applies a DMF treatment (e.g., utilizes a DMF device, for example such as that described in German patent no. DE 10 2005 030 986) that does not heat the particles. In certain embodiments, the present disclosure applies a DMF treatment that does not aggregate the particles. One feature of the present disclosure is that, in many embodiments, it applies a DMF treatment that rotates individual particles about their axes, without also necessarily moving the particles in a direction (e.g., in a circulatory motion) or moving them in bulk. Such individual rotation about a particle's own axis, as provided herein, is particularly and surprisingly useful in the application of mechanical force, especially to structures such as cell membranes or intracellular membranes, for example as exemplified herein.

Particles

Particles for use in accordance with the present disclosure include any particles responsive to DMF as described herein so that their movement, and particularly their rotation about their axis, can be specifically controlled.

In certain embodiments, the present disclosure utilizes magnetic particles with a high, positive magnetic susceptibility, including for example, superparamagnetic, paramagnetic, ferromagnetic, or ferrimagnetic particles.

In certain embodiments, the present disclosure utilizes nanoparticles (i.e., particles whose longest dimension is below 1 um). In certain embodiments, the present disclosure utilizes nanoparticles whose longest dimension is less than about 300 nm; on some embodiments such nanoparticles are particularly useful for delivery into or onto cells. In certain embodiments, the present disclosure utilizes nanoparticles whose longest dimension is less than about 200 nm. In certain embodiments, the present disclosure utilizes nanoparticles whose longest dimension is less than about 100 nm. In certain embodiments, the present disclosure utilizes nanoparticles whose size is within a range of about 10-about 500 nm, or within a range of about 10, about 20, about 30, about 40 or about 50 nm to about 100 nm, about 200 nm, or about 300 nm.

Those of ordinary skill in the art, reading the present specification, would immediately be aware of a variety of appropriate particles, many of which are commercially available, for use in accordance with the present disclosure. Exemplified herein are superparamagnetic iron oxide nanoparticles (SPIONs); those of ordinary skill in the art will readily appreciate the extent to which exemplified results can be expected to be generalizable to other particular nanoparticle formats. Relevant considerations include, for example, that larger magnetic moments can be generated with larger particles, but such can also generate unwanted heat. Additionally, some particles (e.g., certain ferromagnetic particles) may tend to aggregate, which could be undesirable particularly in certain biological contexts. Those skilled in the art will appreciate that certain available coating or other technologies may be utilized in certain embodiments to adjust particle characteristics (e.g., to reduce accumulation) if desired.

In many embodiments, useful magnetic particles have a metal or metal oxide core (e.g., iron oxide), and particularly a ferromagnetic metal oxide core, optionally associated or coated with one or more inorganic (e.g., silica, gold) or organic (e.g., polypeptides, small molecule, glycan, lipid and/or nucleic acid) components.

In certain embodiments, the nanoparticles are crystalline. In certain embodiments, the nanoparticles (e.g., crystalline iron oxide) amplify incoming magnetic fields.

In certain embodiments, useful magnetic particles are characterized in that they lose their magnetism when not exposed to an external magnetic field.

As noted above, the present specification specifically exemplifies use of superparamagnetic nanoparticles, and particularly superparamegnetic iron oxide nanoparticles (e.g., SPIONs; see Hofmann-Amtenbrink et al "Superparamagnetic Nanoparticles for Biomedical Applications" in *Nanostructured Materials for Biomedical Applications*, 2009). In certain embodiments, utilized SPIONs comprise a single ferrimagnetic unit (elementary cell). In certain embodiments one elementary cell includes $8Fe^{2+}$ ions. Use of such particles permits precise computation of parameters such as magnetic energy, torque, and/or mechanical forces, as may not be readily feasible with certain larger particles, for example with changing internal structures (e.g., Bloch walls).

Among other things, the present disclosure establishes that use of specifically targeted DMF-responsive magnetic particles (i.e., magnetic particles associated with a targeting agent that specifically binds to a target structure—e.g., to a target entity or moiety in or on a target structure of interest) shows surprising advantages, even as compared with use of otherwise identical magnetic particles not associated with the targeting agent. Those skilled in the art will be aware of a wide variety of appropriate targeting agents for use in accordance with the present disclosure, as appropriate for particular target entities or moieties of interest.

In certain embodiments, a targeting agent is or comprises a polypeptide, a small molecule, a glycan, a lipid, and/or a nucleic acid. In some particular embodiments, a targeting agent is or comprises an antibody agent. In certain embodiments, a targeting agent is or comprises an antibody or antigen-binding portion thereof.

Target Structures

Those skilled in the art, reading the present disclosure, will immediately appreciate that provided technologies are useful to direct appropriate magnetic particles to any of a variety of target structures, for application of mechanical force thereto. For many biomedical applications, target structures of particular interest are cells or cell structures. In some particular embodiments, target structures are cell membranes or intracellular membranes. In certain embodiments, target structures are organelles, for example selected from the group consisting of lysosomes, the endoplasmic reticulum (ER), the golgi apparatus, the mitochondria.

In certain embodiments, a target structure, entity, or moiety is or comprises a surface marker. In certain embodiments, a surface marker is or comprises a receptor, an enzyme, a channel, etc.

In certain embodiments, a target structure, entity or moiety is or comprises an intracellular target. In certain embodiments, a target structure, entity or moiety is or comprises a marker specifically associated with a disease, disorder, or condition (e.g., with an infectious disease, with cancer, etc.). In certain embodiments, a target structure, entity, or moiety is or comprises a surface marker is or comprises component of transcription machinery, a splicosome, or a ribosome.

The present disclosure particularly exemplifies targeting of superparamagnetic nanoparticles to lysosomal membranes, and application of DMF treatment so that individual superparamagnetic particles rotate about their axes and exert mechanical force on the lysosomal membrane. In certain embodiments, superparamagnetic nanoparticles are targeted to one or more lysosomal membrane components such as, for example, LAMP-1 (CD107a), LAMP-2 (CD107b), or LAMP-3 (CD63).

Applied Forces

In certain embodiments, application of DMF to magnetic particles as described herein exerts a force on the target structure that is within the range of about $10^{-9}$ (i.e., nN range) to about $10^{-12}$ (i.e., pN range); in certain embodiments within the range of about $10^{-10}$ to $10^{-12}$ Newtons.

In certain embodiments, application of DMF to magnetic particles as described herein exerts torque on the target structure within the range of about $10^{-18}$ Nm-$10^{-20}$ Nm. In certain embodiments, the torque is about $10^{-18}$ Nm.

In certain embodiments, magnetic particles are delivered to a target structure in accordance with the present disclosure so that they interact with the target structure at a density sufficient to apply a desired force across an appropriate area.

As described herein, application of DMF treatment to appropriate magnetic particles bound to lysosomes at a density within the range of about 1-60 nanoparticles, on average, per lysosome, is sufficient to achieve lysosomal disruption and/or permeabilization. In certain embodiments, magnetic particles are bound to lysosomes at an average density of about 30 nanoparticles/lysosome.

Applications

In certain embodiments, application of DMF to magnetic particles as described herein is utilized to disrupt or otherwise damage or injure (e.g., permeabilize) the target structure (e.g., a biological membrane). In some particular embodiments, the technology described herein is utilized to induce apoptosis in cells. Advantageously, such disruption (e.g., permeabilization) and/or induction can be achieved without heating.

In particular embodiments, the inventive technology is utilized to kill cancer cells. The cytosol of normal human cells has a neutral pH value (pH about 7). The surrounding of normal human cells in the body has a pH about 7.1, also approximately neutral. Lysosomes, by contrast, have an acidic pH (pH about 5); lysosomal enzymes are typically only active at such low pH. The cytosol of cancerous cells, like that of normal human cells, has a neutral pH value, but their surroundings have an acidic pH. In certain embodiments, the present disclosure provides technologies to apply mechanical force to lysosomal membranes within cancerous cells, so that lysosomal enzymes are released into the cytosol, from which they are pumped out of the cells. In accordance with certain embodiments of the present disclosure, such released lysosomal enzymes actively become activated in the low-pH extracellular milieu that surrounds cancerous cells. They therefore digest materials, including cancer cells, within that surrounding milieu. Without wishing to be bound by any particular theory, it is contemplated that such released lysosomal enzymes will become inactivated once cancerous tissue is destroyed, as normal tissues have a neutral pH milieu.

Alternating Current Superconductor (ACSC) Systems

In certain embodiments, the system used for DMF treatment includes classical aperture, e.g., copper windings, an iron chore with or without integrated cooling. Such systems may have limited penetration depth—e.g., they may be able to produce a magnetic field for control of nanoparticles (internal to the subject's body) no greater than about 1 cm away from the field generator, located external to the subject's body. This limitation may be due to the maximum current density in classical copper windings, e.g., about 2.5 $A/mm^2$, above which the wire can burn. Thus, field amplitude is limited.

It is found that use of a superconducting wire, e.g., with maximum current density at least about 150 $A/mm^2$ allows stronger magnetic fields (greater flux density) and deeper penetration depth for control of nanoparticles that are greater than 1 cm from the field generator at the surface of the subject's body, e.g., from 5 to 10 cm, or from 10 to 20 cm, or from 20 to 30 cm.

In vitro tests with INS-1 cells and a standard device showed that an incoming magnetic field density of 35 mT was strong enough to control the particles at a 2 cm distance from the device. For a standard device with an optimized cooling system, flux-densities of 200 mT can be achieved at this distance. In contrast, a superconducting system (such as the systems described herein) produces larger flux-densities due to, for instance, higher current densities. For example, using the systems provided herein, Tesla values in the low Tesla range (e.g., less than 3 T, e.g., less than 2 T, e.g., less than 1 T, e.g., about 200 mT) can be achieved at larger (e.g., up to 20 cm) distances compared to the Tesla values and penetration depths of standard lab-devices.

FIG. 13 depicts components that can be included in an ACSC system. Components can include, not are not limited to, a transformer, a grid connection, a converter, a controller, a field unit (e.g., actuator), and cooler. In certain embodiments, a field unit activates magnetic particles (e.g., activates movement of the particles) due to its magnetic field. In certain embodiments, the system includes an actuator featuring a superconducting wire (e.g., made of high temperature superconductor material, HTS, e.g., a $YBa_2Cu_3O_x$ (YBCO) coated conductor). In certain embodiments, superconducting systems establish field-density values in the low Tesla range. With HTS materials, the magnetic field strength achievable in an alternating current (AC) system is from about 1 to 3 T for low frequencies, which is sufficient for deep penetration depths and applicable for a variety of working volumes. FIG. 15 shows a map profile of the magnetic field (B, T) as a function of distance (mm) produced by a field generator system as described herein. Improvements in cooling technologies and materials permit higher flux densities.

The system also includes an alternating current (AC) power source, a controller (e.g., inverter and controlling system), and a cooling apparatus (e.g., cryogenic cooling system), as illustrated in the schematic below.

The geometry of the actuator can be adapted for a given working volume needed for a particular patient and/or for a particular kind of treatment (e.g., particular type and/or location of tissue being treated). Various geometries of the actuator—e.g., flat, arc, and toroid/cylinder/sphere/hemisphere are shown in the schematic below, together with the working volume applicable for the particular geometry. The working volume is the volume in which rotatable nanoparticles, as described herein, are located in vivo in a subject and whose movement (e.g., rotation) can be controlled by the externally-applied magnetic field for the desired treatment. For example, FIG. 14 depicts a schematic where an actuator component of an ACSC system is located near (e.g., underneath) a patient for a particular kind of treatment. In certain embodiments, the externally-applied magnetic field causes rotation of the nanoparticles located in the subject at a distance of up to 30 cm from the surface of the field generator (which is located outside the subject). For example, the magnetic field is effective to rotate nanoparticles located in the subject at a distance of 0 to 30 cm from the surface of the field generator, or at a distance of 0 to 25 cm, or 0 to 20 cm, or 0 to 15 cm, e.g., effective at a distance no less than 10 cm, no less than 15, no less than 20 cm, no less than 25 cm, or no less than 30 cm from the surface of the nearest field generator. In certain embodiments, multiple field generators can be used, e.g., to provide for increased effective working volume of rotation of nanoparticles. One or more field generators can be shaped (e.g., as described above, including flat beds, tubes, half-tubes, etc.) and/or arranged to provide an effective working volume of nanoparticle rotation over a desired region of the subject, e.g., during treatment. In certain embodiments, one or more components are hand-held, e.g., such that the magnetic field can be moved over the subject during treatment.

With a flat actuator, there is a large working volume but a smaller penetration depth. The more circular (rounder) the actuator, the smaller the working volume gets, but the greater the penetration that is possible. The geometry of the actuator can be adapted for a desired penetration depth and location of in vivo tissue to be treated. Moreover, in certain embodiments, the actuator moves in relation to the subject (or the subject is moved in relation to the actuator) so that the working volume is adjusted over time, e.g., to treat a larger volume of tissue at the necessary depth.

Furthermore, in addition to adjusting actuator geometry, the magnetic flux distribution can be optimized for a desired working volume by adapting the winding system for the applied field, e.g. by varying the number of turns, the number of phases, or the distribution of the windings within the actuator, for example. The actuator is generally non-homogeneous, with ferromagnetic parts (iron teeth and yoke), paramagnetic parts (air, isolation) and diamagnetic parts (copper, superconductor). This may lead to ripples in the flux distribution and saturation effects. The voltage and/or current of the inverter can be controlled according to the geometry of the actuator to minimize the influence of these effects. Furthermore, the efficiency of the superconducting windings can be increased by deformation of the standard sinusoidal current.

In certain embodiments, the system is operated remotely, e.g., the magnetic field generator may be controlled remotely. Operation of the system may be performed by a practitioner (e.g., nurse, or doctor) from a location remote from the subject. In certain embodiments, components of the system (e.g., the field generator) are portable and/or wearable. Therapy by controlled movement of nanoparticles in in vivo tissue may require treatment over multiple sessions, or over one or more sessions that are lengthy (e.g., more than an hour, two hours, or longer). The size, remote operability, and/or portability of the system may allow more convenient treatment (e.g., cancer treatment), e.g., treatment in a clinical as opposed to an operating room, or even home treatment.

In certain embodiments, the magnetic field and consequently the magnetic field density depends on the field-producing current (e.g., where field ranges can be calculated via the "Maxwell Equations"). Values of field amplification inside nanoparticles (e.g., crystalline iron nanoparticles) and field-particle interactions (e.g., forces, e.g., moments) can be computed for anisotropic material (e.g., magnetic particles) to design systems and methods for various treatment applications.

Illustrative Network Environment

FIG. 11 shows an illustrative network environment 1100 for use in the methods and systems described herein. In brief overview, referring now to FIG. 11, a block diagram of an exemplary cloud computing environment 1100 is shown and described. The cloud computing environment 1100 may include one or more resource providers 1102a, 1102b, 1102c (collectively, 1102). Each resource provider 1102 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1102 may be connected to any other resource provider 1102 in the cloud computing environment 1100. In some implementations, the resource providers 1102 may be connected over a computer network 1108. Each resource provider 1102 may be connected to one or more computing device 1104a, 1104b, 1104c (collectively, 1104), over the computer network 1108.

The cloud computing environment 1100 may include a resource manager 1106. The resource manager 1106 may be connected to the resource providers 1102 and the computing devices 1104 over the computer network 1108. In some implementations, the resource manager 1106 may facilitate the provision of computing resources by one or more resource providers 1102 to one or more computing devices 1104. The resource manager 1106 may receive a request for a computing resource from a particular computing device 1104. The resource manager 1106 may identify one or more resource providers 1102 capable of providing the computing resource requested by the computing device 1104. The resource manager 1106 may select a resource provider 1102 to provide the computing resource. The resource manager 1106 may facilitate a connection between the resource provider 1102 and a particular computing device 1104. In some implementations, the resource manager 1106 may establish a connection between a particular resource provider 1102 and a particular computing device 1104. In some implementations, the resource manager 1106 may redirect a particular computing device 1104 to a particular resource provider 1102 with the requested computing resource.

FIG. 12 shows an example of a computing device 1200 and a mobile computing device 1250 that can be used in the methods and systems described in this disclosure. The computing device 1200 is intended to represent various forms of digital computers, such as laptops, desktops, workstations, personal digital assistants, servers, blade servers, mainframes, and other appropriate computers. The mobile computing device 1250 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1200 includes a processor 1202, a memory 1204, a storage device 1206, a high-speed interface 1208 connecting to the memory 1204 and multiple high-speed expansion ports 1210, and a low-speed interface 1212 connecting to a low-speed expansion port 1214 and the storage device 1206. Each of the processor 1202, the memory 1204, the storage device 1206, the high-speed interface 1208, the high-speed expansion ports 1210, and the low-speed interface 1212, are interconnected using various busses, and may be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as a display 1216 coupled to the high-speed interface 1208. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1204 stores information within the computing device 1200. In some implementations, the memory 1204 is a volatile memory unit or units. In some implementations, the memory 1204 is a non-volatile memory unit or units. The memory 1204 may also be another form of computer-readable medium, such as a magnetic or optical disk.

The storage device 1206 is capable of providing mass storage for the computing device 1200. In some implementations, the storage device 1206 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1202), perform one or more methods, such as those described above. The instructions can also be stored by one or more storage devices such as computer- or machine-readable mediums (for example, the memory 1204, the storage device 1206, or memory on the processor 1202).

The high-speed interface 1208 manages bandwidth-intensive operations for the computing device 1200, while the low-speed interface 1212 manages lower bandwidth-intensive operations. Such allocation of functions is an example only. In some implementations, the high-speed interface 1208 is coupled to the memory 1204, the display 1216 (e.g., through a graphics processor or accelerator), and to the high-speed expansion ports 1210, which may accept various expansion cards (not shown). In the implementation, the low-speed interface 1212 is coupled to the storage device 1206 and the low-speed expansion port 1214. The low-speed expansion port 1214, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1200 may be implemented in a number of different forms, as shown in the figure. For example, it may be implemented as a standard server 1220, or multiple times in a group of such servers. In addition, it may be implemented in a personal computer such as a laptop computer 1222. It may also be implemented as part of a rack server system 1224. Alternatively, components from the computing device 1200 may be combined with other components in a mobile device (not shown), such as a mobile computing device 1250. Each of such devices may contain one or more of the computing device 1200 and the mobile computing device 1250, and an entire system may be made up of multiple computing devices communicating with each other.

The mobile computing device 1250 includes a processor 1252, a memory 1264, an input/output device such as a display 1254, a communication interface 1266, and a transceiver 1268, among other components. The mobile computing device 1250 may also be provided with a storage device, such as a micro-drive or other device, to provide additional storage. Each of the processor 1252, the memory 1264, the display 1254, the communication interface 1266, and the transceiver 1268, are interconnected using various buses, and several of the components may be mounted on a common motherboard or in other manners as appropriate.

The processor 1252 can execute instructions within the mobile computing device 1250, including instructions stored in the memory 1264. The processor 1252 may be implemented as a chipset of chips that include separate and multiple analog and digital processors. The processor 1252 may provide, for example, for coordination of the other components of the mobile computing device 1250, such as control of user interfaces, applications run by the mobile computing device 1250, and wireless communication by the mobile computing device 1250.

The processor 1252 may communicate with a user through a control interface 1258 and a display interface 1256 coupled to the display 1254. The display 1254 may be, for example, a TFT (Thin-Film-Transistor Liquid Crystal Display) display or an OLED (Organic Light Emitting Diode) display, or other appropriate display technology. The display interface 1256 may comprise appropriate circuitry for driving the display 1254 to present graphical and other information to a user. The control interface 1258 may receive commands from a user and convert them for submission to the processor 1252. In addition, an external interface 1262 may provide communication with the processor 1252, so as to enable near area communication of the mobile computing device 1250 with other devices. The external interface 1262 may provide, for example, for wired communication in some implementations, or for wireless communication in other implementations, and multiple interfaces may also be used.

The memory 1264 stores information within the mobile computing device 1250. The memory 1264 can be implemented as one or more of a computer-readable medium or media, a volatile memory unit or units, or a non-volatile memory unit or units. An expansion memory 1274 may also be provided and connected to the mobile computing device 1250 through an expansion interface 1272, which may include, for example, a SIMM (Single In Line Memory Module) card interface. The expansion memory 1274 may provide extra storage space for the mobile computing device 1250, or may also store applications or other information for the mobile computing device 1250. Specifically, the expansion memory 1274 may include instructions to carry out or supplement the processes described above, and may include secure information also. Thus, for example, the expansion memory 1274 may be provided as a security module for the mobile computing device 1250, and may be programmed with instructions that permit secure use of the mobile computing device 1250. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 1252), perform one or more methods, such as those described above. The instructions can also be stored by one or more storage devices, such as one or more computer- or machine-readable mediums (for example, the memory 1264, the expansion memory 1274, or memory on the processor 1252). In some implementations, the instructions can be received in a propagated signal, for example, over the transceiver 1268 or the external interface 1262.

The mobile computing device 1250 may communicate wirelessly through the communication interface 1266, which may include digital signal processing circuitry where necessary. The communication interface 1266 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1268 using a radio-frequency. In addition, short-range communication may occur, such as using a Bluetooth®, Wi-Fi™, or other such transceiver (not shown). In addition, a GPS (Global Positioning System) receiver module 1270 may provide additional navigation- and location-related wireless data to the mobile computing device 1250, which may be used as appropriate by applications running on the mobile computing device 1250.

The mobile computing device 1250 may also communicate audibly using an audio codec 1260, which may receive spoken information from a user and convert it to usable digital information. The audio codec 1260 may likewise generate audible sound for a user, such as through a speaker, e.g., in a handset of the mobile computing device 1250. Such sound may include sound from voice telephone calls, may include recorded sound (e.g., voice messages, music files, etc.) and may also include sound generated by applications operating on the mobile computing device 1250.

The mobile computing device 1250 may be implemented in a number of different forms, as shown in the figure. For example, it may be implemented as a cellular telephone 1280. It may also be implemented as part of a smart-phone 1282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet. In certain embodiments, the operating unit is connected to a magnetic field system (such as those described herein) via WLAN.

The computing system can include clients and servers. A client and server are generally remote from each other and typically interact through a communication network. The relationship of client and server arises by virtue of computer programs running on the respective computers and having a client-server relationship to each other.

In certain embodiments, the system (e.g., control unit) includes a webserver program that enables operation of the system. In certain embodiments, the webserver is managed with a standard web browser (e.g., tablet, smartphone, computer, personal computer) that is connected via a standard computer network.

EXAMPLES

Example 1

The present Example demonstrates that use of DMF to induce rotation as described herein in targeted superparamagnetic iron oxide nanoparticles (SPIONs) can be used to remotely activate apoptosis. Specifically, the present Example demonstrates that SPIONs conjugated with LAMP1 (Lysosomal-associated membrane protein 1) antibodies (LAMP1-SPION) internalize into cells and bind to lysosomal membranes. This Example further demonstrates that subsequent remote activation of the dynamic magnetic field causes mechanical disruption and/or permeabilization of lysosomes, which leads to apoptosis via extravasation of lysosomal contents into the cytoplasm and a decrease of intracellular pH. As those skilled in the art will appreciate, certain examples of SPIONs conjugated with LAMP1 antibodies are described in Gruttner et al, "Synthesis and Antibody Conjugation of Magnetic Nanoparticles with Improved Specific Power Absorption Rates for Alternating Magnetic Field Cancer Therapy," *Journal Magnetism and Magnetic Materials* 2007.

Results

Figure 1:
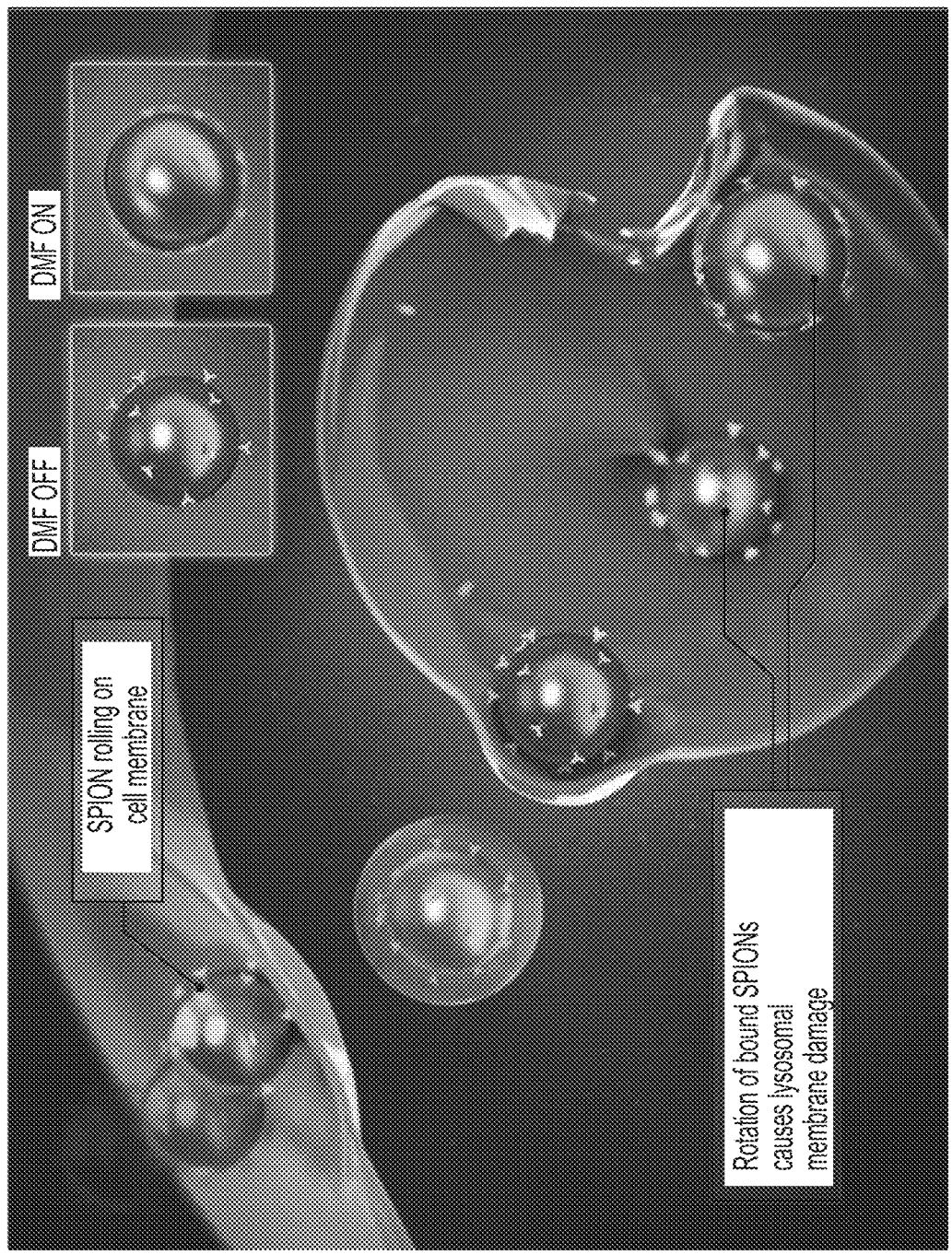
FIG. 1 presents a schematic depiction of exemplified use of LAMP1-SPIONs with DMF to disrupt lysosomal membranes and induce apoptosis. Additional supporting information, including Movie 1: Illustrating the rotational control of magnetic microparticles achieved with a DMF device; Movie 2: Illustrating the rotational control of magnetic nanoparticles (300 nm diameter) achieved with a DMF device; and Movie 3: Dynamic confocal microscopy study illustrating the real-time destruction of lysosomes via DMF and LAMP1-SPIONs, is available free of charge via the Internet at http://pubs.acs.org.
Figure 2A:
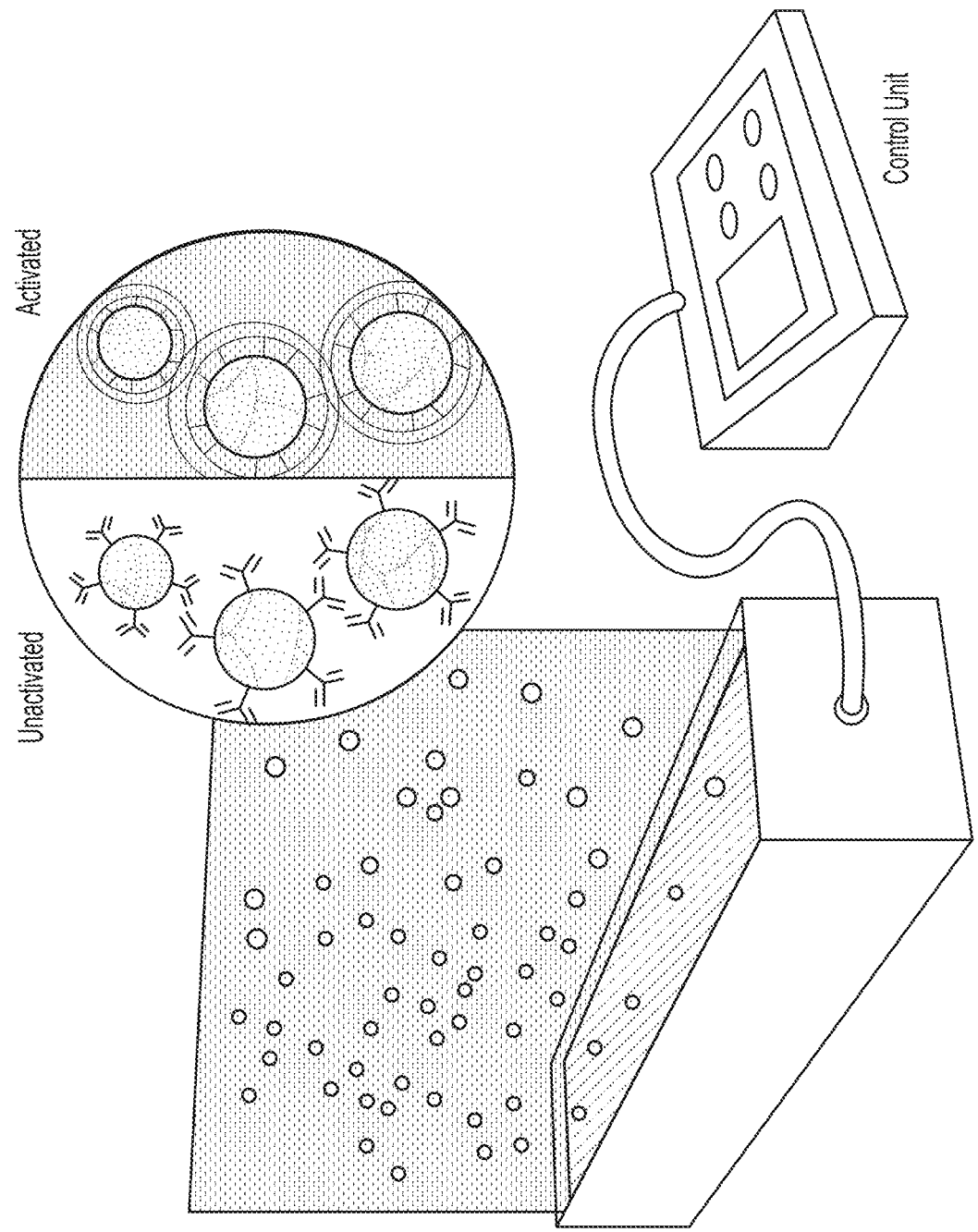
FIGS. 2A-2B illustrate DMF controlled rotation of magnetic nanoparticles.

Dynamic Magnetic Field Stimulation Results in Rotation of Individual Nanoparticles A DMF generator as described in German Patent No: DE 10 2005 030 986 was utilized to control directional movement and self-centered rolling. FIG. 2A shows a schematic representation of a DMF generator utilized in the present Exemplification. The device controls rotation and movement of magnetic nanoparticles (e.g., SPIONs) with a low frequency (10-40 Hz) field. The DMF generator causes the nanoparticles to rotate around their own axis. To demonstrate the pattern of the particle movement, the rotation of larger magnetic beads of different sizes (5.8, 1, 0.5 and 0.3 µm diameter) was first monitored by filming them in a cell culture dish under a microscope. Once the DMF is switched on, the beads start to rotate around their own axis, which also causes a slow directional movement of the beads across the floor of the dish, as shown in FIGS. 3A-3D. The present study clearly demonstrated that the applied DMF treatment enables a self-turning of magnetic particles. The speed of rotation can be controlled by varying the frequency setting on the DMF device. This observation suggested that the DMF could be used to contrive a virus-like interaction between the SPIONs and the cell surface, which in turn could enhance internalization of the SPIONs into the cytosol. Once the SPIONs have internalized into the intracellular compartments, e.g. endosomes or lysosomes, the loaded SPIONs can be operated non-invasively by DMF to regulate the cellular compartmental activities and further cell functions, as for example, shown in FIG. 2B.

Figure 4A:
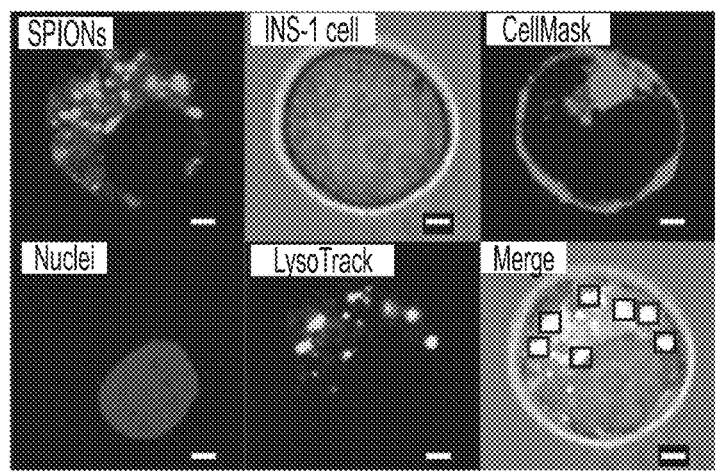
FIGS. 4A-4D demonstrates the loading of magnetic nanoparticle into lysosomes in INS-1 cells.
Figures 4B, 4C:
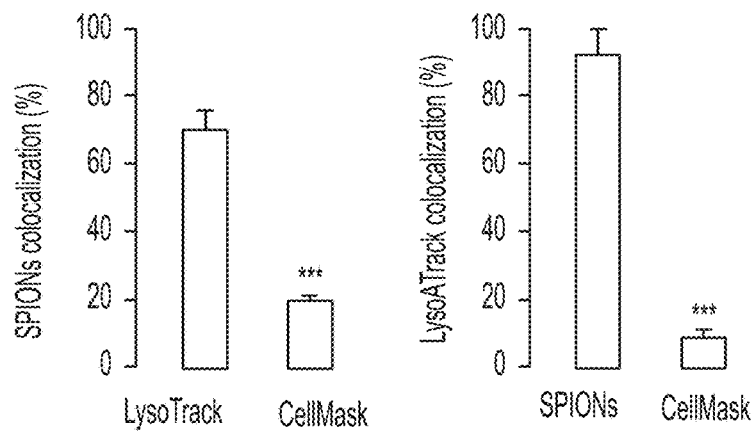

Dynamic Magnetic Field Stimulation Enhances Uptake of Superparamagnetic Nanoparticles Internalization of SPIONs into living cells was reported previously. In the present study, the internalization efficiency in the absence or presence of DMF stimulation is first evaluated. To monitor the process of SPION internalization, the present study used fluorescently labeled (TRITC) 100-nm SPIONs and incubated them with rat insulinoma cells (INS-1). 300-nm SPIONs were also tested, but they exhibited markedly lower loading efficiency. The present study then applied a DMF field for 20 min. at a frequency of 20 Hz, before staining the cells using the plasma membrane marker CellMask, the lysosomal marker LysoTracker Green and the nuclear marker Hoechst 34580. The cells were then imaged by live confocal microscopy, which demonstrated that the majority of the SPIONs were loaded into the lysosomes after 20 min. of DMF treatment, as shown in FIG. 4A. FIG. 4B shows 71.2±3.8% of SPIONs colocalized with the lysosomal marker LysoTracker Green, while only 18.2±2.2% of SPIONs colocalized with the plasma membrane and early endosome probe CellMask. Conversely, FIG. 4C shows 91±8.7% of the LysoTracker Green fluorescence appeared in conjunction with SPIONs, which means that nearly all lysosomes contained several loaded SPIONs.

Figure 4D:
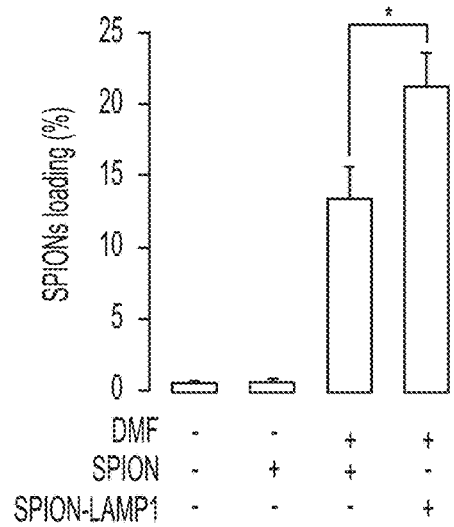

Next the present study conjugated SPIONs with an antibody against the lysosomal membrane protein, LAMP1 (LAMP1-SPION). The loading efficiencies between SPION and LAMP1-SPION were compared in order to evaluate if the conjugation of the LAMP1 antibody enhanced internalization and loading into the lysosomes. LAMP1-SPION nanoparticles were more efficiently loaded into the lysosomes than the unconjugated SPIONs, and the loading efficiency after 20 min. FIG. 4D shows the loading efficiencies of DMF treatment averaged 13.3±2.3% and 21.2±2.4% for SPIONs and LAMP1-SPIONs, respectively.

Dynamic Magnetic Field Stimulation can Injure Lysosomes Via Antibody-Conjugated Superparamagnetic Nanoparticles To evaluate whether DMF treatment has the potential to injure lysosomes in LAMP1-SPION-loaded cells, the present study visualized the lysosome compartment with the marker LysoTracker Green. After DMF-facilitated loading of the LAMP1-SPION nanoparticles, the cells were cultured at 37° C. for 40 min to allow binding of the antibody paratope on the nanoparticles to LAMP1 in the lysosomal membrane. After that culture period, any remaining LAMP1-SPION nanoparticles outside the cells were removed by washing, before subjecting the cells to DMF treatment (20 Hz) for 20 minutes.

Figure 5A:
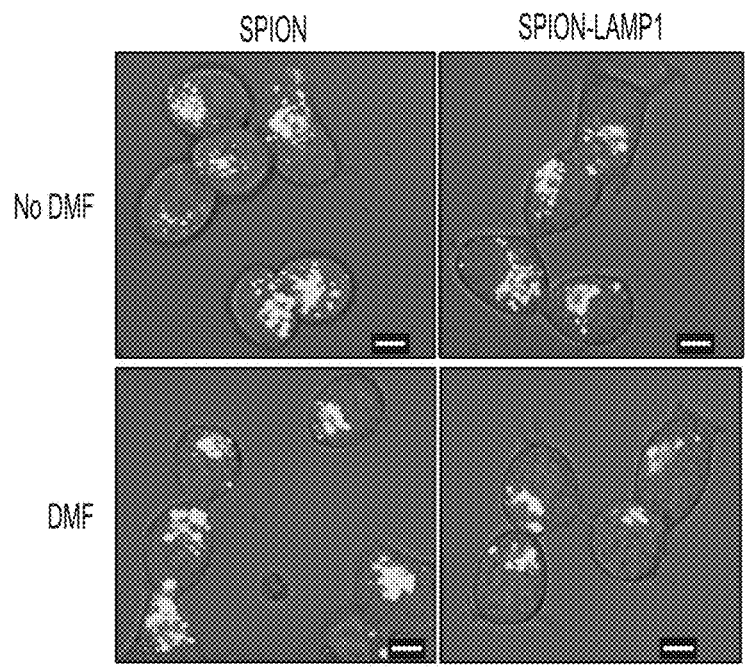
FIGS. 5A-5D demonstrates that DMF treatment decreases intracellular lysosomes and the pH in LAMP1-SPION loaded INS-1 cells.
Figure 5B:
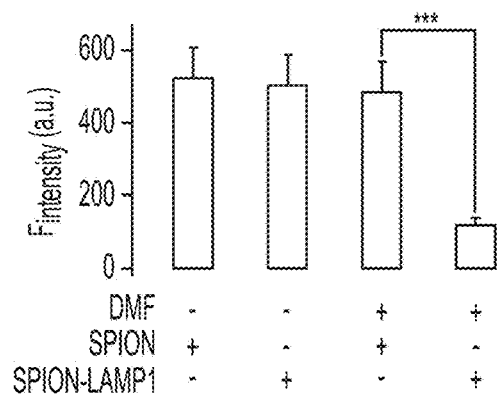
Figure 5C:
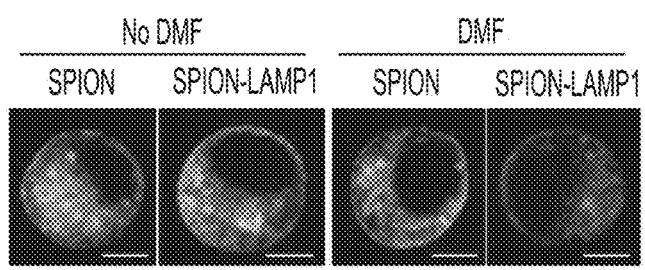
Figure 5D:
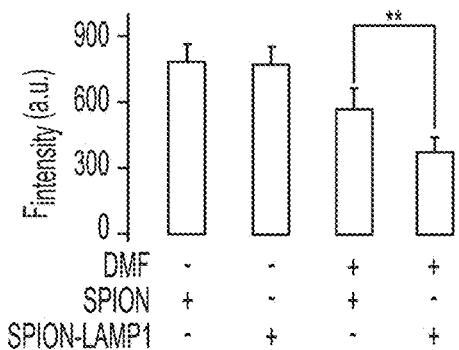

The capability of the DMF treatment to disrupt and/or permeabilize the compartments of the lysosomes was evaluated by assessing changes in LysoTracker Green fluorescence intensity. Indeed, in LAMP1-SPION-loaded cells, the DMF treatment significantly decreased LysoTracker Green fluorescence by 75% as compared to cells loaded with conventional SPIONs without the LAMP1 antibody (483.6±84.2 A.U. vs. 120.3±20.9 A.U. for SPION- and LAMP1-SPION-treated cells, respectively, as shown in FIGS. 5A and 5B. To confirm these findings, the present study next used the acidotropic probe (pKa=5.2) LysoSensor Green DND 189 as described in Eto et al., "Glucose Metabolism and Glutamate Analog Acutely Alkalinize Ph of Insulin Secretory Vesicles of Pancreatic Beta-Cells," *American Journal of Physiology Endocrinology and Metabolism* 2003. The rationale for this experiment was that disruption of lysosomes would reduce the volume of the very acidic compartments in the cell and lead to a decrease in LysoSensor Green fluorescence. The results are shown in FIGS. 5C and 5D.

Figure 6:
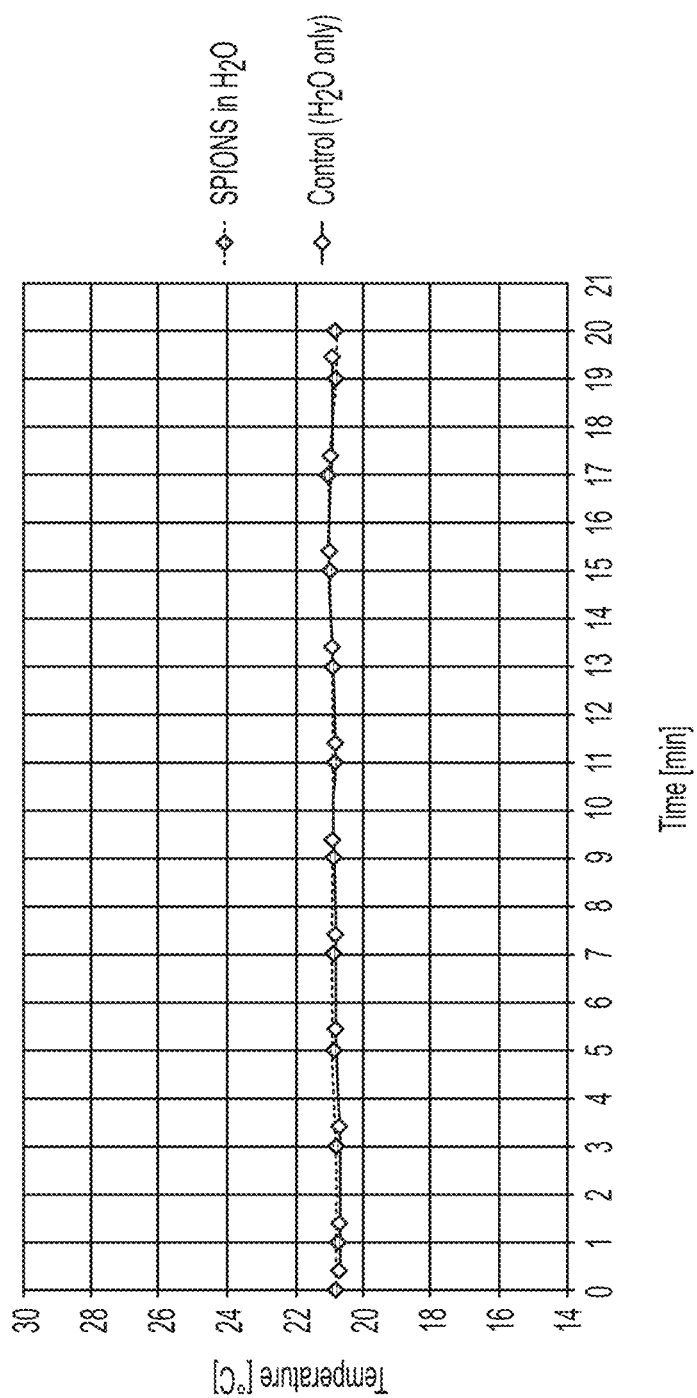
FIG. 6 is a temperature plot demonstrating that DMF-field induced SPION rotation does not increase temperature. A dish with 100 nm SPIONs (10 mg/ml) in water and a control dish containing water only, each containing a temperature probe, were placed simultaneously on the DMF device. The dishes were then subjected to the DMF field for 20 min. at 20 Hz. No significant change in temperature was observed in either the dish with the SPIONs (thicker, darker curve) or the control dish (thinner, lighter curve).

Prior to DMF treatment, the present study found no difference in fluorescence intensity between SPION- and LAMP1-SPION-loaded cells. DMF treatment had no effect in SPION-loaded cells. In contrast, in LAMP1-SPION-treated cells fluorescence intensity dropped (769.5±82.5 A.U./cell vs. 368.4±69.6 A.U./cell in SPION-vs. LAMP1-SPION treated cells, respectively; P<0.001). In light of the low frequency of the alternating magnetic fields utilized herein, heat induction, which is common if not ubiquitous when high frequency alternating magnetic fields are utilized, was not expected to occur. The present study confirmed the absence of heat induction by monitoring temperature runs in phantoms. These experiments showed that no significant change in temperature was caused by the DMF induced magnetic field, as shown in the temperature plot of FIG. 6. Taken together, these results suggest that the remote application of the DMF treatment causes permeabilization of lysosomal compartments, induced via the torque of the membrane-bound LAMP1-SPIONs.

Effects of Dynamic Magnetic Field Stimulation of Superparamagnetic Nanoparticles in Human Primary Cells To monitor the LAMP1-SPION loaded lysosomes, SPIONs are covalently attached to both LAMP1 antibodies and the fluorescence marker TRITC (TRITC-LAMP1-SPION). To further validate the possibility to translate the present findings to clinical settings, the present study used isolated primary cells from human pancreatic islets and seeded on glass bottom petri dishes. Then TRITC-LAMP1-SPIONs were added to cell culture medium, followed by DMF treatment or no treatment, and finally the cells were fixed for confocal microscopy.

Figure 7A:
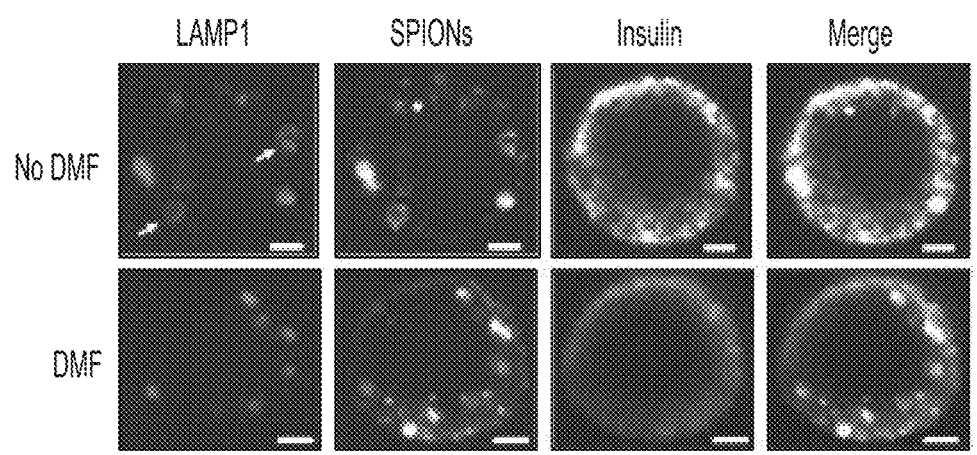
FIGS. 7A-7F demonstrates that DMF treatment disrupts lysosomes in human pancreatic beta cells after loading with LAMP1-SPIONs.
Figures 7B, 7C:
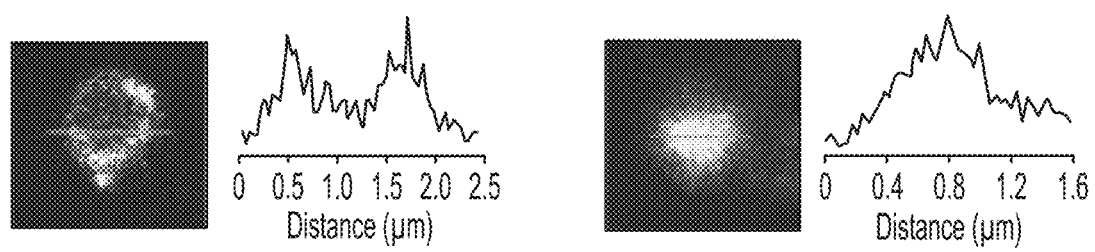

Human primary islet cells contained larger lysosomes than INS-1 cells as assessed by TRITC fluorescence (as shown in FIG. 7A, upper images). To assess co-localization of LAMP1 and TRITC-LAMP1-SPION, LAMP1 was detected by indirect immunocytochemistry using a Cy2-tagged secondary antibody. In cells not exposed to DMF treatment, LAMP1 and TRITC-LAMP1-SPION co-localized by 49.9±9.2%, which was not significantly affected by DMF treatment (54.8±9.5%) (Data not shown). These results indicate that the bonds between LAMP1 and TRITC remain stable during DMF treatment. Interestingly, the TRITC-LAMP1-SPIONs loaded into the cells mainly appeared around the boundaries of structures, which are likely to represent a location in the lysosomal membrane, as for example shown in FIG. 7B. However, after a second round of DMF treatment, most of the LAMP1 was apparently separated from the TRITC-LAMP1-SPIONs (as shown in FIG. 7A, bottom images) and the SPIONs aggregated tightly (as shown in FIG. 7C).

Figure 7D:
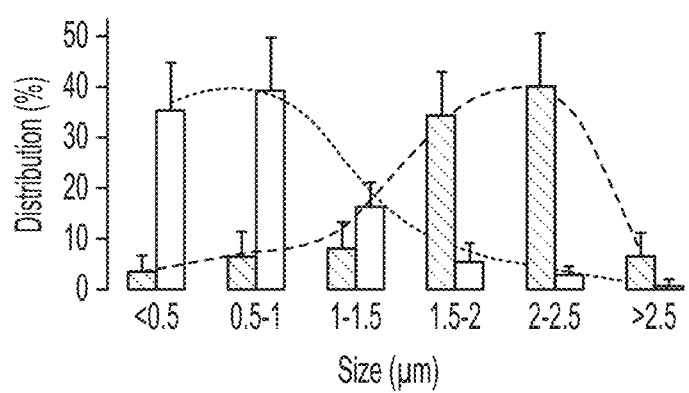
Figure 7E:
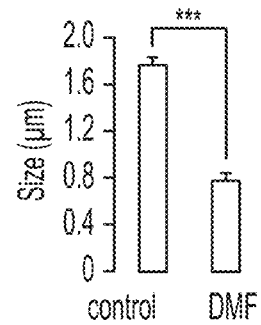

DMF treatment also led to a marked downward shift in the distribution of lysosomal sizes, as for example shown in FIG. 7D, and accordingly the average size of lysosomes decreased from 1.77±0.06 μm (n=141) to 0.79±0.05 μm (n=105) after DMF treatment, as shown in FIG. 7E. These results suggest that the second round of DMF treatment in cells loaded with TRITC-LAMP1-SPIONs results in a certain degree of damage to the lysosome membrane. However, a potential alternative explanation could be that the detachment of TRITC-LAMP1-SPIONs occurs from the lysosome membrane without disruption which can lead to the particles aggregating in the center of the still intact lysosomes.

Figure 7F:
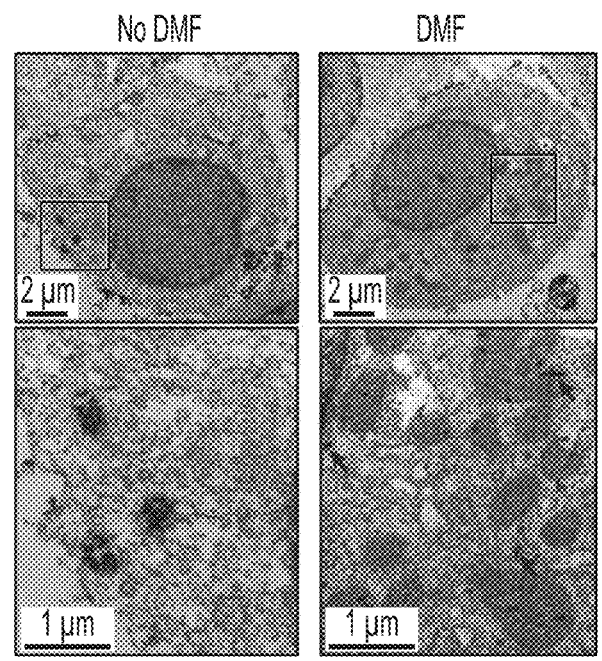

To address this possibility, the subcellular locations of the LAMP1-SPIONs were further identified by transmission electrical microscopy (TEM). The TEM images clearly showed that LAMP1-SPION particles had accumulated within intracellular compartments after loading into cells (as shown in FIG. 7F, left). In contrast, after the second round of DMF treatment, the LAMP1-SPIONs were scattered throughout the cells (as shown in FIG. 7F, right). These results demonstrate that DMF-induced rotational movement of LAMP1-SPIONs are also capable of disrupting lysosomal membranes in human primary cells.

Consequences of DMF-Mediated Disruption of Lysosomes

Disruption of lysosomes has previously been reported to activate apoptotic reactions. To determine whether DMF treatment can elicit apoptosis in LAMP1-SPION-loaded cells, the present study measured the extent of apoptosis in INS-1 cells with and without DMF. Annexin V and 7-AAD were used to indicate early and late stage apoptosis, respectively (as shown in FIG. 8A). After DMF treatment, early and late apoptosis in LAMP1-SPION loaded INS-1 cells significantly increased from 4.56±0.55% to 12.45±1.6% and from 0.73±0.17% to 1.31±0.16%, as evidenced by positive staining for Annexin V or 7-AAD, respectively (shown in FIGS. 8B and 8C). Furthermore, the elevated rates of apoptosis also had consequences on cell proliferation during culture. A single 20-minute DMF treatment (20 Hz) in SPION-loaded cells had no significant effect on cell number during a 6-days culture period when compared to control cells. In contrast, the number of LAMP1-SPION loaded cells after DMF treatment was significantly (p<0.001) lower from day 2 and onwards (as shown in FIG. 8D). These results indicate that the attack on lysosomes via DMF-activated lysosomal membrane-targeted SPIONs prompts apoptotic cell death and affects the growth of the cell population.

DISCUSSION

The present Example describes a novel biomedical platform based on a unique dynamic magnetic field generator, which in combination with superparamagnetic nanoparticles can be utilized for various new applications.

Several prior studies have investigated the effect of 'alternating magnetic fields' on magnetic nanoparticles. These studies generally used high-frequency (typically MHz range), or at least medium-frequency (e.g., kHz range), alternations in the magnetic field polarity, and observed that targeted iron oxide nanoparticles caused damage to cellular membranes leading to permeabilization. In most such studies, energy dissipated locally as heat by the iron oxide nanoparticles was thought to lead to (and therefore presumably to be required for) disruption of lipid bilayers. Huang et al., "Remote Control of Ion Channels and Neurons through Magnetic-Field Heating of Nanoparticles," *Nature Nanotechnology* 2010 demonstrated a temperature-induced change in fluorescence when a fluorochrome was attached to a magnetic nanoparticle and exposed to an alternating magnetic field, whereas no change was observed in free fluorochromes.

Figure 2B:
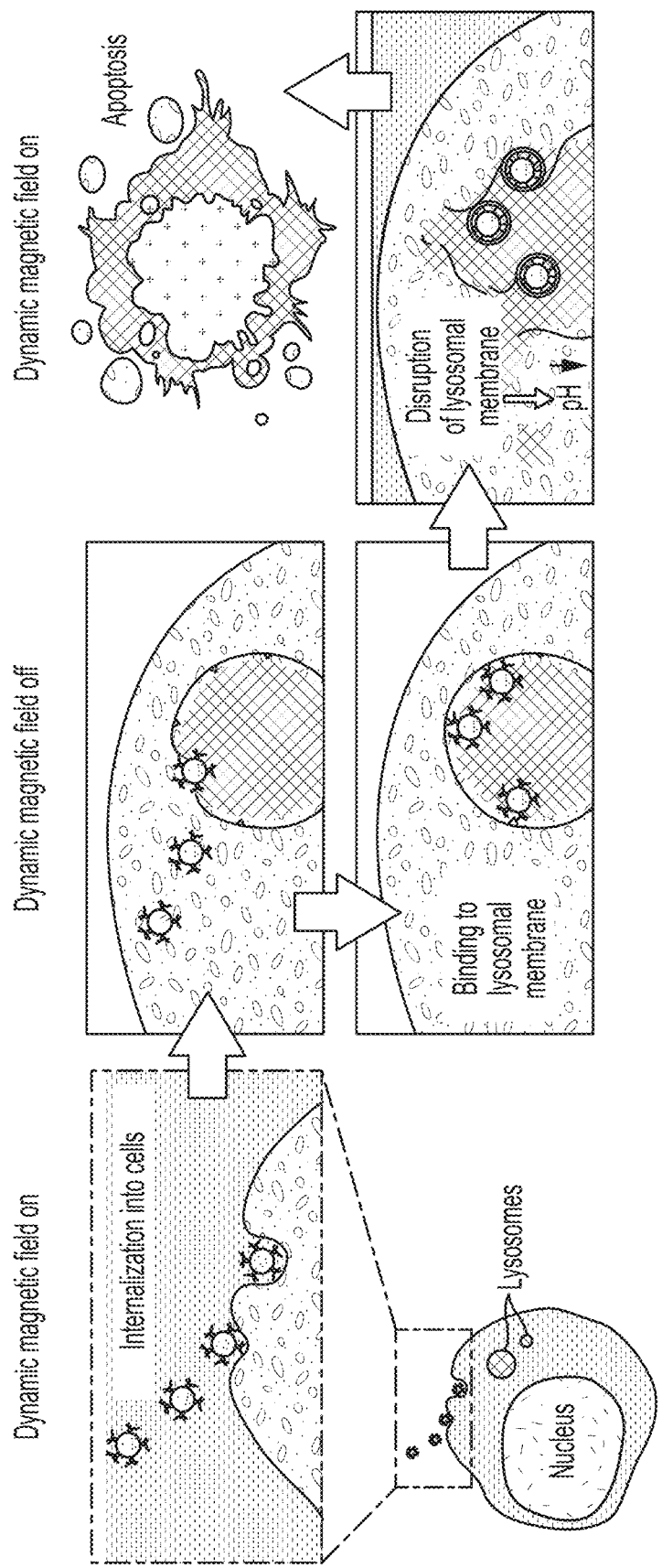
Figure 3A:
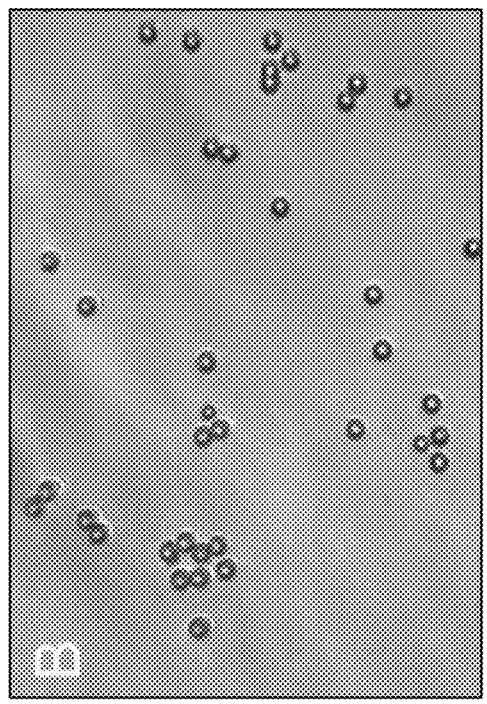
FIGS. 3A-3D demonstrates DMF-induced rotation of magnetic particles. In order to enable better visualization of the effect of the DMF on magnetic particles under the microscope, larger micrometer sized magnetic beads (diameter 5.8 μm) were used. A dish containing beads in a physiologic salt solution (Krebs buffer) was placed in the vicinity of the DMF device. Once the DMF was switched on, the beads started to rotate around their own axis, which also caused a slow directional movement of the beads across the floor of the dish. The beads completed a rotation of 360° in seconds (time depends on the viscosity of the liquid) between the FIG. 3A and FIG. 3D. The speed of rotation can be controlled by varying the frequency setting on the DMF device and in this experiment was varied between 5-15 Hz. Movie 1, noted above, depicts this rolling.
Figure 3B:
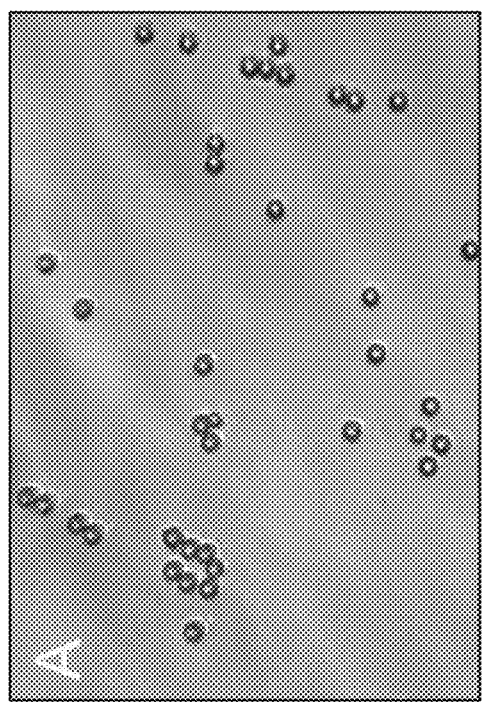
Figure 3C:
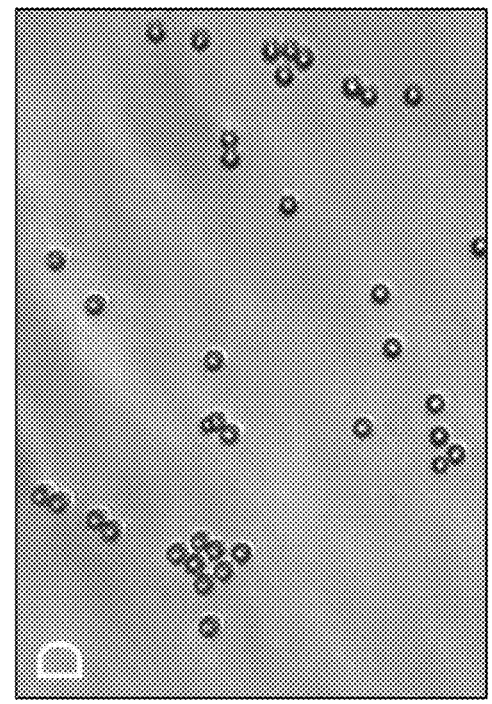
Figure 3D:
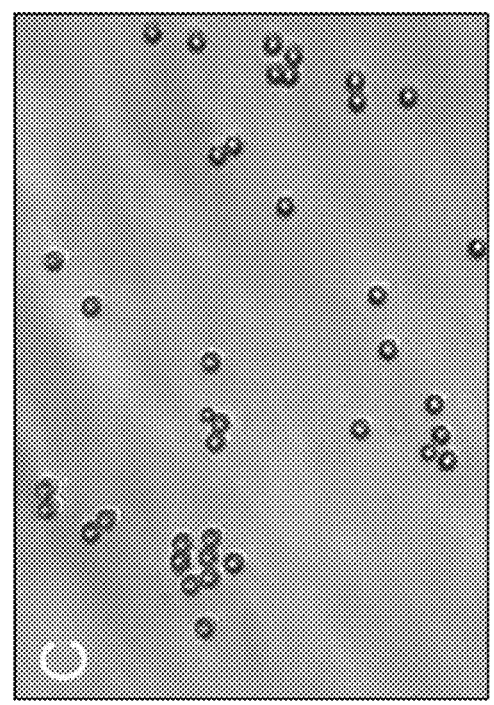

In contrast to these reports using high-frequency alternating (but not dynamic) magnetic fields, the present DMF approach uses low-frequency (~10-20 Hz), dynamic (i.e. moving) magnetic fields of ~30 mT that uniquely induce rotation of every individual particle in the field around their own axis (as illustrated in FIG. 2B). The speed of this rotation (and its direction) can be controlled by varying the frequency setting on the device. For example, at lower frequencies nanoparticles can be prompted to roll over cell membranes, which may mimic the movement of viruses along cell membrane surfaces, as for example, described in Burckhardt et al., "Virus Movements on the Plasma Membrane Support Infection and Transmission between Cells,". *PLoS Pathogen* 2009, and increase the efficiency with which nanoparticles internalize into cells. Higher rotational speeds can be used in order to destroy particular targets via rotational shear forces without inducing unwanted thermal effects. Molecular simulations of lipid bilayers have shown that both incremental shear and tension can destabilize cell membranes, and that the energy that is required to cause such membrane damage can be achieved with rotating magnetic nanoparticles.

The present study has applied the DMF on LAMP1 antibody-conjugated superparamagnetic iron oxide nanoparticles to facilitate nanoparticle uptake into cells and to disrupt the lysosomal membrane as a means to induce cell apoptosis. The DMF approach described herein has at least two major advantages: 1) Nanoparticles can be rotated around their own axis, and 2) No significant heat is created.

Heat creation is the presumed mechanism of how high-frequency alternating magnetic fields cause damage to cell membranes as suggested in Ivkov, "Application of High Amplitude Alternating Magnetic Fields for Heat Induction of Nanoparticles Localized in Cancer," *Clinical Cancer Research* 2005. This however can potentially cause extensive and unspecific cellular necrosis. By contrast, the DMF technology described herein does not induce heating; when applied in cellular systems or organisms, therefore, temperature at the site can be maintained within the physiological temperature range (e.g., typically considered to be within a range of about 37° C. to about 42° C.). Technologies described herein achieve induction of apoptosis specifically in nanoparticle-loaded cells only. Apoptotic cells are removed in vivo by endogenous scavenger systems e.g. the innate immune system and macrophages. Tissue damage is thus limited to only the targeted cells, in contrast to procedures leading to supraphysiological temperatures and resultant necrosis, potentially sparing wide-spread acute inflammatory reactions.

In certain embodiments, provided methodologies achieve a particularly high degree of specificity of nanoparticle-mediated intervention, by targeting of nanoparticles to a particular cell type and/or into a desired subcellular compartment is important. Among other things, in certain embodiments, the provided technology platform represents an example of unique utilization of DMFS to target magnetic nanoparticles to specific intracellular compartments.

Previous reports have demonstrated the usefulness of magnetic nanoparticles for controlling activity of plasma membrane receptors or ion channels. Upon protracted stimulation of receptors or ion channels there is solid evidence for down-regulation of their activities. One important mechanism of such desensitization is internalization of receptors or ion channels to intracellular sites where they reside in an inactive standby pool. In the context of nanoparticle-mediated activation of receptors or ion channels this means that after activation, the number of the receptors/ion channels in plasma membrane decreases and the desired cellular signals and responses are blunted. Moreover, the magnetic nanoparticles themselves are internalized already after short incubation with live cells via the endocytotic pathway, as for example described in Gupta et al., "Cytotoxicity Suppression and Cellular Uptake Enhancement of Surface Modified Magnetic Nanoparticles," *Biomaterials* 2005 and Bogart et al., "Photothermal Microscopy of the Core of Dextran-Coated Iron Oxide Nanoparticles During Cell Uptake," *ACS Nano* 2012.

In certain embodiments, the present disclosure makes use of this property of internalization and facilitates the process by DMF treatment to accelerate delivery of nanoparticles (e.g., as exemplified, of LAMP1 antibody-attached nanoparticles) to intracellular compartments, and specifically to the lysosome. Following down the endocytotic pathway, the targeted nanoparticles enter the early- and late-endosomes and afterwards they should enter other compartments, e.g. ER, via recycling endosomes, or being removed from the lysosomes. In the lysosomes, the targeting agent associated with its nanoparticle recognizes and binds to its target moiety (e.g., LAMP1, which is highly expressed in the lysosomal membrane). In response to a low frequency DMF, as employed in the disclosure herein, the now bound nanoparticle generates dynamic forces strong enough to tear the lysosomal membrane, leading to destruction of the lysosome integrity, leakage of lysosomal enzymes and finally induction of apoptosis.

In INS-1 cells, the present study observed that the SPIONs mostly loaded into lysosomes after 20 minutes DMF treatment (FIG. 4A). This preferential lysosomal localization was also observed when SPIONs were located into primary human pancreatic islet cells (as shown in FIG. 7A). However, as the direction and extent of intracellular membrane trafficking may differ markedly between cell types, those of skill in the art will appreciate that adjustments to lysosome loading efficiency may be desirable when this technology is applied to other cell types. Those skilled in the art will appreciate that this technology can provide tools to regulate specific subcellular compartmental functions including not only the nuclei, but also compartments such as the ER, Golgi apparatus and different types of endosomes along the intracellular membrane trafficking system.

Those skilled in the art will also appreciate that adjustments (e.g., stronger fields etc.) may be desirable, when applying embodiments of provided technology to in vivo contexts. For example, the particular DMF field strength utilized in the present Example was about 30 mT, and may have a reach of up to about 1 cm, though such penetration was not required (reach of even 1 mm being sufficient in certain instances). Those skilled in the art will appreciate that stronger fields (e.g., potentially within the range of mT to T) may be required for certain in vivo applications, for example in order to reach deep organs, which may well involve penetration of 10 cm, 20 cm, 30 cm, 40 cm, or more. Regardless, ultimate clinical translation using presently disclosed low frequency DMF approach may be more straightforward than using high-frequency alternating fields, among other things because the DMF fields are not expected to cause nonspecific heating of tissues through induced eddy currents and should therefore have a better safety profile.

The achievement of rotational control on nanoparticles with the DMF method as described herein has many other potential applications beyond the model systems used here, in both biomedical and non-biological nanotechnology fields. To give but a few examples, magnetic actuation has been shown to control timing and drug release from vesicles containing iron oxide nanoparticles. An increase in permeability of lysosomal membranes not only can be used to promote apoptosis, such as through the release of proteolytic enzymes and increase in reactive oxygen species, but can also increase the efficacy of drugs trapped in lysosomes. Because sequestration of drugs in lysosomes is responsible for up to 40% of whole tissue drug uptake, lysosomal drug trapping plays an important role in the development of tumor drug resistance. Thus, is some embodiments, provided DMF-mediated lysosomal membrane permeabilization technologies could be used to treat cancer drug resistance.

CONCLUSIONS

In summary, using a unique dynamic magnetic field (DMF) generator the present exemplification can control rotational movements of superparamagnetic iron oxide nanoparticles (SPIONs) in solution. This rotational nanoparticle movement was applied for remote induction of cell death by injuring lysosomal membrane structures. SPIONs are covalently coated with antibodies targeting the lysosomal protein marker LAMP1 (LAMP1-SPION). Remote activation of slow rotation of LAMP1-SPIONs with 20 Hz for 20 minutes, significantly improved the efficacy of cellular internalization of the nanoparticles. It is observed that 71.2±3.8% of LAMP1-SPIONs accumulated along the membrane in lysosomes in rat insulinoma tumor cells due to binding of LAMP1-SPIONs to endogenous LAMP1. Further activation of torque by the LAMP1-SPIONs bound to lysosomes resulted in rapid decrease in size and number of lysosomes, attributable to tearing of the lysosomal membrane by the shear force of the rotationally activated LAMP1-SPIONs. This remote activation resulted in increased cell apoptosis and impaired cell growth. The findings of the present disclosure suggest that DMF treatment of lysosome-targeted nanoparticles offers a non-invasive tool to induce apoptosis remotely, providing an important platform technology for a wide range of biomedical applications.

Methods
Nanoparticle Assembly.

The protocol of conjugation of LAMP1 antibodies to magnetic nanoparticles was described previously, for example, in Gruttner, "Synthesis and Antibody Conjugation of Magnetic Nanoparticles with Improved Specific Power Absorption Rates for Alternating Magnetic Field Cancer Therapy," *Journal Magnetism and Magnetic Materials* 2007. Briefly, SPION nanoparticles (Micromod, Germany) were amino-functionalized and the density of amino groups per mg of particles was determined. After washing, the other parts of amino groups were reacted with sulfo-SMCC in PBS-EDTA buffer to introduce maleimide groups on the particle surface. The monoclonal LAMP1 antibody (Abcam, UK) was purified with a G-25 column containing PBS/EDTA buffer to remove the glycerin and sodium azide. After purification the LAMP1 antibody was treated with imnothiolane solution to introduce the SH groups. After washing the SH-modified antibody with PBS-EDTA buffer in a G-25 column, the maleimide-modified particles were added. The particles were shaken for 1 h at room temperature. Then cystein was added to quench the remaining reactive sites. Finally the particles were purified with PBS buffer in magnetic columns in a high gradient magnetic field.

DMF Device.

The dynamic fields to control SPION rotation used in this study were created with a DMF generator (DM-01, Feldkraft and Stetter Elektronik, Germany). The device consists of an array of multiphase coil systems, where the coils are displaced against each other. The field can be altered in a highly dynamic fashion. A device-integrated digital controller regulates the frequency as well as the magnetic flux. The dynamic flux produces an electromagnetic gradient force $\vec{F}=(\vec{m}\nabla)\cdot\vec{B}$, where m are the magnetic moments of the beads in total and B is the dynamic flux density field vector. This vector is established by the H field of the present device. The magnetic field strength generated by the DMF device used in this study is approximately as large as 30 mT (rms).

Live Cell Imaging.

Cells were seeded onto glass coverslips. After DMF treatment, live images were acquired using a Zeiss 510 Meta confocal system with a ×40 water immersion objective (NA=1.2). SPION-TRITC was visualized by excitation at 543 nm and emitted light collected using a long-pass 560 nm filter. The pinhole was ~1 airy unit and the scanning frame was 512×512 pixels. The cellular location of SPION was stained with the plasma membrane marker CellMask (Invitrogen, USA), lysosome marker LysoTracker Green (Invitrogen, USA) and a marker for cell nuclei, Hoechst 34580 (Invitrogen, USA). Image analysis was performed with ZEN 2009 software (Zeiss, Germany). Co-localization was analyzed by a Pearson's efficiency methods within ZEN 2009. The SPION-TRITC co-localization of lysosomes was calculated by coefficient $$c_{SPION} = \frac{Pixel_{colocalized}}{Pixel_{total}} \times 100.$$

Likewise, the LysoTracker-labeled lysosomes were counted by coefficient $$c_{lysosome} = \frac{Pixel_{colocalized}}{Pixel_{total}} \times 100.$$

The coefficient is reported as a percentage from 0-100, with 0 meaning no co-localization and 100 meaning all pixel-pairs are co-localized. Since TRITC labelled SPIONs were loaded into all the INS-1 cells after DMF treatment, the present study used the fluorescence intensity of TRITC to indicate the amount of SPIONs in a cell after 3 times washing. The total SPION loading efficiency was calculated by percentage of $$\frac{F_{Annexin\ V(7-AAD)}}{F_{Hoechst\ 34580}} \times 100$$

number of fluorescence intensity of TRITC to the intensity of Hoechst 34580 which reflects cell number in a field.

Transmission Electron Microscopy (TEM) Imaging.

The preparation of cells for TEM is now discussed. Briefly, INS-1 insulinoma tumor cells were treated with DMF, followed by fixation in 2.5% glutaraldehyde for 1 hour at 4° C. The cells were then treated with 1% osmium tetroxide, dehydrated, and embedded in AGAR100 (Oxford instruments Nordiska AB, Stockholm) before being sliced in ultra-thin sections (70-90 nm). After slicing, the samples were placed on Cu grids and contrasted with uranyl acetate and lead citrate. The TEM images were obtained using a JEM 1230 electron microscope (Jeol-USA, Peabody, Mass., USA).

Human Islet Cell Immunostaining.

Human islets were provided by the EXODIAB Human Tissue Lab and the Nordic Network of Clinical Islet Transplantation Programme (www.nordicislets.org). The islet cells were separated in a $Ca^{2+}$-free solution at 37° C. for 10 minutes and treated with DMF after 12 hour culture on the cover slips centered dish (MatTek, Germany). Then the cells were fixed with 3% PFA-PIPES and 3% PFA-Na2BO4 for 5 min. and 10 min., respectively, followed by permeabilization with 0.1% Triton-X 100 for 30 min. and blocked with 5% normal donkey serum in PBS for 15 minutes. Guinea pig sourced antibody against insulin (EuroProxima, Netherlands) was diluted in 5% block buffer and incubated overnight at 4° C. Immunoreactivity was done using fluorescently labeled secondary antibodies: cy2 anti-guinea pig (1:400) and cy5 anti-mouse (1:400). The images of SPION-TRITC (EX: 543 nm), cy2-labeled insulin (EX: 488 nm) and cy5-labeled LAMP1 (EX: 633 nm) were visualized through three or four channels by a confocal system (Zeiss, Germany). Lysosomal size (LAMP1 marked) was calculated using the profile function of the ZEN 2009 software based on the shapes of the fluorescence areas.

Intracellular pH Measurement.

INS-1 cells were seeded on the glass centered dish (MatTek, Germany), loaded with SPION or SPION-LAMP1 and treated by DMF. Then the cells were incubated with 1 µM acidic indicator, LysoSensor Green DND 189 (Invitrogen, USA) for 30 min. in 37° C. After incubation, the cells were washed out and the fluorescence images were acquired by confocal microscopy. The average fluorescence intensity per cell was measured using the ZEN 2009 software and further applied for quantitative analysis.

Cell Apoptosis Detection.

FITC-Annexin V (51-65874X, BD, USA) and 7-AAD (51-68981E, BD, USA) were used to assess early and late apoptosis of INS-1 cells. After DMF treatment, the INS-1 cells were incubated with the dyes at 37° C. for 30 minutes. Images were acquired under identical conditions (using the same settings for pinhole (1 airy unit), exposure time, gain and scanning speed). Fluorescence intensity was analyzed by the ZEN 2009 software and early/late stage apoptosis was quantified by percentage of $$\frac{F_{Annexin\ V(7-AAD)}}{F_{Hoechst\ 34580}} \times 100$$

number of Annexin V/7-AAD positive cells to the number of Hoechst 34580 stained cells.

Proliferation.

INS-1 cells were seeded on 24-well plates loaded with SPION or SPION-LAMP1 nanoparticles and treated by DMF once/day. Then the cell number was calculated by a plate cytometer after 6 hours of DMF treatment. Cells were counted once per day for 5 days.

Temperature Measurements.

A dish with 100 nm SPIONs (10 mg/ml) in water and a dish without the SPIONs in water as a control, each containing a temperature sensor (Radial leaded glass-encapsulated NTC thermistor, EPCOS Inc., Germany), were placed simultaneously on the DMF device. The dishes were then subjected to the DMF field for 20 minutes at 20 Hz and the temperature recorded in each dish.

Statistical Analysis.

The data was presented as average±standard error of the mean (S.E.M.). Statistical comparison of paired-factors experiments was performed by Student's T-test and one-way analysis of variance (ANOVA) and the Friedman tests were performed for multi-factor experiments which have more than two group treatments in one experiment.

Example 2

In this example, a cooler is used to remove emerging losses produced by superconductors in AC fields with AC current transport. Losses in ACSC systems depend on moving vortexes, which are classical field enclosures in the superconductor. Such vortexes may be due to the standard frequencies (e.g., 50 Hz, e.g., 60 Hz) that are used in existing systems; however, the present devices operate at frequencies that are considerably lower than standard frequencies, as described below. Vortex losses are high at standard frequencies; however, they are far lower in the lower frequency range presented herein (e.g., 30 Hz or less, e.g., 20 Hz). Such losses make it difficult to operate the superconductor at cryogenic temperatures. Efforts to reduce losses are not cost effective, and therefore, these efforts have not been pursued heretofore.

The present devices are operated at 20 Hz to establish a field with magnetic character (e.g., no material constants). As a result, vortex losses are significantly reduced compared to devices that are operated at standard frequencies (e.g., 50 Hz, e.g., 60 Hz), thereby minimizing heating inside the superconductor. Therefore, an inexpensive cooling medium, for example, liquid nitrogen can be used to maintain the conductors in the state of superconductivity. In contrast, devices that utilize standard frequencies and experience high losses demand expensive cooling media like hydrogen, neon, or helium.

In vitro tests with INS-1 cells showed that an incoming magnetic field density of 35 mT was strong enough to control the particles. A standard lab-device can establish this flux-density in a 2 cm distance. For a standard available device with an optimized cooling system, flux-densities of 200 mT can be achieved. However, a superconducting system (such as the systems described herein) produces larger flux-densities due to, for example, higher current densities. For example, using the systems provided herein, Tesla values (e.g., less than 3 T, e.g., less than 2 T, e.g., less than 1 T, e.g., about 200 mT) can be achieved at larger (e.g., up to 20 cm) distances compared to the Tesla values and penetration depths of standard lab-devices.

What is claimed is:

1. A method of applying mechanical force to a target structure, the method comprising:
exposing a target structure to magnetic particles so that the magnetic particles bind to the target structure; and
applying a dynamic magnetic field (DMF) with a strength of at least 30 mT to the magnetic particles to induce rotation of each of the magnetic particles about an axis of the magnetic particles, so that a mechanical force within the range of about 1 fN to about 1 nN is applied to the target structure, wherein the DMF is applied using a DMF generator, and the DMF generator comprises an actuator comprising an array of superconducting coil windings.

2. The method of claim 1, wherein the mechanical force is applied to the target structure without the magnetic particles being significantly heated.

3. The method of claim 1, wherein the magnetic particles are or comprise a member selected from the group consisting of nanoparticles, superparamagnetic nanoparticles, and superparamagnetic iron oxide nanoparticles ("SPIONs").

4. The method of claim 1, wherein the magnetic particles are characterized by an iron oxide core.

5. The method of claim 1, wherein the magnetic particles are characterized in losing their magnetism when not exposed to an external magnetic field.

6. The method of claim 1, wherein the magnetic particles are associated with a targeting agent that specifically binds to the target structure.

7. The method of claim 6, wherein the targeting agent is covalently linked to the magnetic particles.

8. The method of claim 6, wherein the targeting agent is or comprises a member selected from the group consisting of antibodies, polypeptides, small molecules, glycans, lipids, and nucleic acids that specifically bind to a target moiety in or on the target structure, and combinations thereof.

9. The method of claim 8, wherein the target moiety is or comprises a member selected from the group consisting of polypeptides, glycans, and nucleic acids.

10. The method of claim 1, wherein the target structure is or comprises a member selected from the group consisting of cell membranes, tumor-associated markers, ion channels, intracellular membranes, lysosomal membranes, intracellular entities, and tumor-associated entities.

11. The method of claim 10, wherein the intracellular entities are or comprise an organelle.

12. The method of claim 11, wherein the organelle is selected from the group consisting of endoplasmic reticulum (ER), golgi apparatus, mitochondria, and combinations thereof.

13. The method of claim 10, wherein the intracellular entities are or comprise a member selected from the group consisting of organelles, components of transcription machinery, splicosomes, and ribosomes.

14. The method of claim 10, wherein the target structure is or comprises lysosomal membranes, and the magnetic particles are associated with a targeting agent that specifically binds to the target structure.

15. The method of claim 14, wherein the targeting agent is covalently linked to the magnetic particles.

16. The method of claim 15, wherein the targeting agent specifically binds to a target moiety on the surface of the lysosomal membrane.

17. The method of claim 16, wherein the target moiety is or comprises LAMP-I (CD107a), LAMP-2 (CD107b), or LAMP-3 (CD63).

18. The method of claim 1, wherein the step of exposing comprises exposing the target structure to the magnetic particles so that the magnetic particles bind to the target structure with a density sufficient to apply the mechanical force across a relevant area of the target structure.

19. The method of claim 10, wherein the step of exposing comprises exposing the target structure to the magnetic particles so that, on average, about 1 to about 60 magnetic particles become bound to each lysosomal membrane.

20. The method of claim 19, wherein the step of exposing comprises exposing the target structure to the magnetic particles so that, on average, about 10 to about 50 magnetic particles become bound to each lysosomal membrane.

21. The method of claim 19, wherein the step of exposing comprises exposing the target structure to the magnetic particles so that, on average, about 30 magnetic particles become bound to each lysosomal membrane.

22. The method of claim 1, wherein the strength is within the range of 30 mT to 5 T.

23. The method of claim 1, wherein the applying step comprises applying the dynamic magnetic field with an in vivo reach selected from the group consisting of within the range of at least 1 cm, of at least 2 cm to 5 cm, of at least 10 cm, and of at least 50 cm.

24. The method of claim 10, wherein the tumor-associated markers are or comprise a member selected from the group consisting of cell-surface entities and intracellular entities.

25. The method of claim 1, wherein the applying step comprises controlling a rotation speed of each of the magnetic particles.

* * * * *